(12) United States Patent
Sirhan et al.

(10) Patent No.: US 12,076,504 B2
(45) Date of Patent: Sep. 3, 2024

(54) ASPIRATION CATHETERS WITH EXPANDABLE DISTAL TIP

(71) Applicant: Elixir Medical Corporation, Milpitas, CA (US)

(72) Inventors: Motasim Sirhan, Los Altos, CA (US); Benjamyn Serna, Gilroy, CA (US); Kim Nguyen, Union City, CA (US); John Yan, Los Gatos, CA (US); Matthew Tyler Surber, Woodside, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 18/482,711

(22) Filed: Oct. 6, 2023

(65) Prior Publication Data

US 2024/0033475 A1 Feb. 1, 2024

Related U.S. Application Data

(63) Continuation of application No. PCT/US2023/016449, filed on Mar. 27, 2023.

(Continued)

(51) Int. Cl.
*A61F 2/01* (2006.01)
*A61M 25/00* (2006.01)

(52) U.S. Cl.
CPC .... *A61M 25/0052* (2013.01); *A61M 25/0074* (2013.01); *A61M 2202/0014* (2013.01)

(58) Field of Classification Search
CPC ...... A61F 2/01; A61F 2/013; A61F 2002/011; A61M 25/00; A61M 25/0052; A61M 25/0074; A61M 2202/0014
See application file for complete search history.

(56) References Cited

U.S. PATENT DOCUMENTS 4,324,262 A 4/1982 Hall
5,254,107 A * 10/1993 Soltesz ............... A61M 25/005
604/525

(Continued)

FOREIGN PATENT DOCUMENTS

CN 103417261 B 3/2016
CN 105662534 B 1/2020

(Continued)

OTHER PUBLICATIONS

Dictionary.com. Definition and Meaning of "Separate". Accessed online Sep. 14, 2022.

(Continued)

*Primary Examiner* — Vi X Nguyen
(74) *Attorney, Agent, or Firm* — Wilson Sonsini Goodrich & Rosati

(57) ABSTRACT

An aspiration catheter includes a catheter body having a proximal end, a distal end, and an aspiration lumen therebetween. A distal segment comprising an expandable distal tip of the aspiration catheter comprises a membrane and an expandable supporting structure, such as a scaffold, configured to radially expand the expandable distal tip. The expandable supporting structure may include supporting elements and other features which increase resistance to collapse of the expandable membrane under vacuum or negative pressure applied to aspirate clot through the aspiration lumen in the expanded configuration.

35 Claims, 48 Drawing Sheets

Related U.S. Application Data

(60) Provisional application No. 63/487,773, filed on Mar. 1, 2023, provisional application No. 63/327,326, filed on Apr. 4, 2022, provisional application No. 63/324,540, filed on Mar. 28, 2022.

(56) References Cited

U.S. PATENT DOCUMENTS

| | | |
|---|---|---|
| 5,403,334 A | 4/1995 | Evans et al. |
| 6,206,911 B1 | 3/2001 | Milo |
| 7,144,386 B2 | 12/2006 | Korkor et al. |
| 7,220,269 B1 | 5/2007 | Ansel et al. |
| 7,247,166 B2 | 7/2007 | Pienknagura |
| 7,291,165 B2 | 11/2007 | Rosenthal et al. |
| 7,625,401 B2 | 12/2009 | Clifford et al. |
| 7,918,884 B2 | 4/2011 | Majercak et al. |
| 7,942,920 B2 | 5/2011 | Majercak |
| 8,075,510 B2 | 12/2011 | Aklog et al. |
| 8,206,428 B2 | 6/2012 | Pryor |
| 8,323,760 B2 | 12/2012 | Zheng et al. |
| 8,535,211 B2 | 9/2013 | Campbell et al. |
| 8,764,814 B2 | 7/2014 | Solem |
| 8,858,497 B2 | 10/2014 | Di et al. |
| 8,915,954 B2 | 12/2014 | Young et al. |
| 8,939,931 B2 | 1/2015 | Von |
| 9,078,682 B2 | 7/2015 | Lenker et al. |
| 9,402,938 B2 | 8/2016 | Aklog et al. |
| 9,445,829 B2 | 9/2016 | Brady et al. |
| 9,717,519 B2 | 8/2017 | Rosenbluth et al. |
| 9,987,028 B2 | 6/2018 | Lowinger et al. |
| 10,231,751 B2 | 3/2019 | Sos |
| 10,321,925 B2 | 6/2019 | Ulm, III |
| 10,342,557 B2 | 7/2019 | Youn et al. |
| 10,500,047 B2 | 12/2019 | Olson et al. |
| 10,722,631 B2 | 7/2020 | Salahieh et al. |
| 10,792,056 B2 | 10/2020 | Vale et al. |
| 10,959,865 B2 | 3/2021 | Thomas |
| 11,020,582 B2 | 6/2021 | Cambronne et al. |
| 11,045,215 B2 | 6/2021 | Epstein et al. |
| 2004/0243119 A1 | 12/2004 | Lane et al. |
| 2005/0085896 A1 | 4/2005 | Bonsignore et al. |
| 2006/0058838 A1 | 3/2006 | Bose et al. |
| 2006/0173529 A1 | 8/2006 | Blank |
| 2007/0005103 A1 | 1/2007 | Schaeffer |
| 2007/0073373 A1 | 3/2007 | Bonsignore |
| 2007/0093744 A1 | 4/2007 | Elmaleh |
| 2008/0086110 A1 | 4/2008 | Galdonik et al. |
| 2010/0174290 A1 | 7/2010 | Wuebbeling et al. |
| 2010/0204779 A1 | 8/2010 | Schuessler et al. |
| 2011/0034991 A1 | 2/2011 | Barthel et al. |
| 2011/0092892 A1 | 4/2011 | Nitsan et al. |
| 2011/0152920 A1 | 6/2011 | Eckhouse et al. |
| 2011/0160761 A1 | 6/2011 | Ferrera et al. |
| 2012/0041449 A1 | 2/2012 | Eckhouse et al. |
| 2012/0116440 A1 | 5/2012 | Leynov et al. |
| 2013/0123901 A1 | 5/2013 | Connor et al. |
| 2013/0131690 A1 | 5/2013 | Nagl et al. |
| 2014/0155981 A1 | 6/2014 | Ferrera et al. |
| 2014/0249569 A1 | 9/2014 | Kusleika |
| 2015/0305756 A1 | 10/2015 | Rosenbluth et al. |
| 2015/0359547 A1* | 12/2015 | Vale .................. A61M 25/0082 606/115 |
| 2016/0058458 A1 | 3/2016 | Hansen et al. |
| 2016/0220741 A1 | 8/2016 | Garrison et al. |
| 2016/0256180 A1 | 9/2016 | Vale et al. |
| 2016/0367285 A1 | 12/2016 | Sos |
| 2017/0086862 A1 | 3/2017 | Vale et al. |
| 2017/0105743 A1 | 4/2017 | Vale et al. |
| 2017/0265878 A1 | 9/2017 | Marchand et al. |
| 2017/0274180 A1 | 9/2017 | Garrison et al. |
| 2017/0290686 A1 | 10/2017 | Sirhan et al. |
| 2017/0333060 A1 | 11/2017 | Panian |
| 2018/0104041 A1 | 4/2018 | Hauser |
| 2018/0193043 A1 | 7/2018 | Marchand et al. |
| 2018/0235644 A1 | 8/2018 | Jaffe et al. |
| 2019/0328411 A1 | 10/2019 | Vale et al. |
| 2019/0381221 A1 | 12/2019 | Ogle |
| 2020/0121334 A1 | 4/2020 | Galdonik et al. |
| 2021/0046230 A1 | 2/2021 | Fitzgerald et al. |
| 2021/0128184 A1 | 5/2021 | Fulkerson et al. |
| 2021/0153883 A1 | 5/2021 | Casey et al. |
| 2022/0125450 A1 | 4/2022 | Sirhan et al. |
| 2022/0273323 A1 | 9/2022 | Baron et al. |
| 2023/0149035 A1 | 5/2023 | Sirhan et al. |
| 2024/0074770 A1 | 3/2024 | Baron et al. |

FOREIGN PATENT DOCUMENTS

| | | |
|---|---|---|
| CN | 111388056 A | 7/2020 |
| CN | 212015705 U | 11/2020 |
| CN | 112641487 A | 4/2021 |
| CN | 113081169 A | 7/2021 |
| CN | 113116462 A | 7/2021 |
| CN | 214342506 U | 10/2021 |
| EP | 3335647 A2 | 6/2018 |
| JP | 2015505250 A | 2/2015 |
| JP | 2017517338 A | 6/2017 |
| WO | WO-9207606 A1 | 5/1992 |
| WO | WO-9531149 A1 | 11/1995 |
| WO | WO-2007033052 A2 | 3/2007 |
| WO | WO-2013072777 A2 | 5/2013 |
| WO | WO-2015189354 A1 | 12/2015 |
| WO | WO-2015196156 A1 | 12/2015 |
| WO | WO-2016113047 A1 | 7/2016 |
| WO | WO-2017074721 A1 | 5/2017 |
| WO | WO-2017200956 A1 | 11/2017 |
| WO | WO-2018132387 A1 | 7/2018 |
| WO | WO-2019033121 A1 | 2/2019 |
| WO | WO-2019059949 A2 | 3/2019 |
| WO | WO-2019115809 A1 | 6/2019 |
| WO | WO-2019212984 A1 | 11/2019 |
| WO | WO-2020079082 A1 | 4/2020 |
| WO | WO-2020099386 A1 | 5/2020 |
| WO | WO-2021016213 A1 | 1/2021 |
| WO | WO-2022020366 A2 | 1/2022 |
| WO | WO-2023192201 A1 | 10/2023 |

OTHER PUBLICATIONS

PCT/US2020/042827 International Search Report dated Dec. 3, 2020.
PCT/US2021/042398 International Search Report and Written Opinion of the International Searching Authority dated Feb. 7, 2022.
PCT/US2023/016449 International Search Report and Written Opinion dated Aug. 14, 2023.
U.S. Appl. No. 17/568,559 Office Action dated Feb. 16, 2023.
U.S. Appl. No. 17/568,559 Office Action dated Mar. 24, 2022.
U.S. Appl. No. 17/568,559 Office Action dated Oct. 5, 2022.
Co-pending U.S. Appl. No. 18/636,086, inventors Sirhan; Motasim et al., filed on Apr. 15, 2024.
EP20843195.7 European Search Report and Opinion dated Jul. 24, 2023.

* cited by examiner

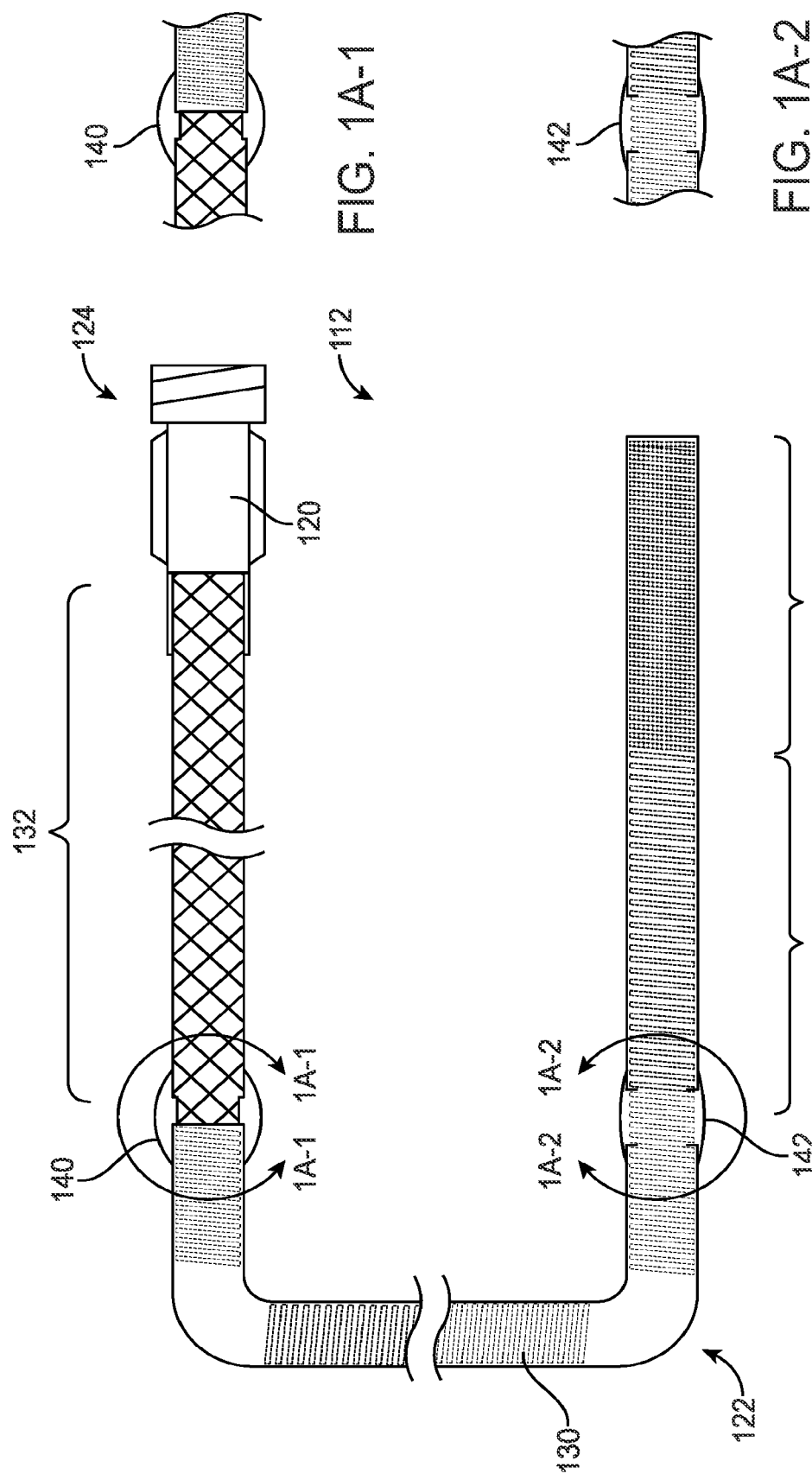

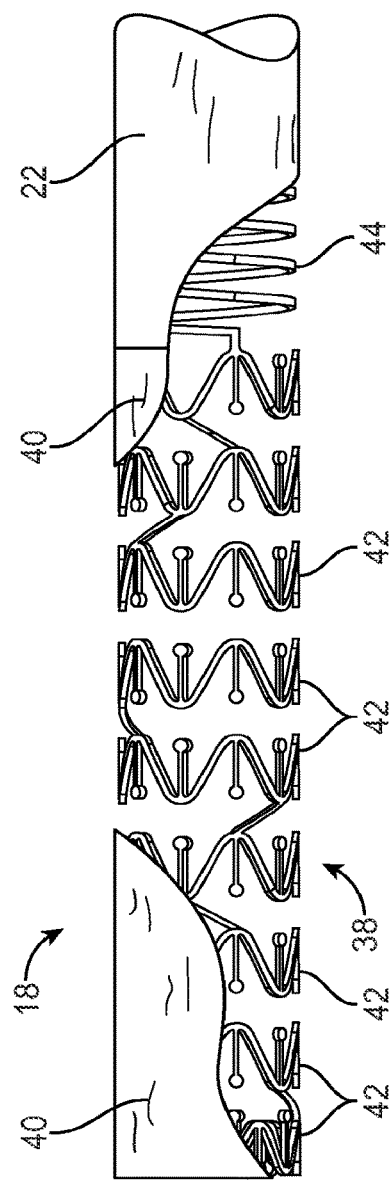
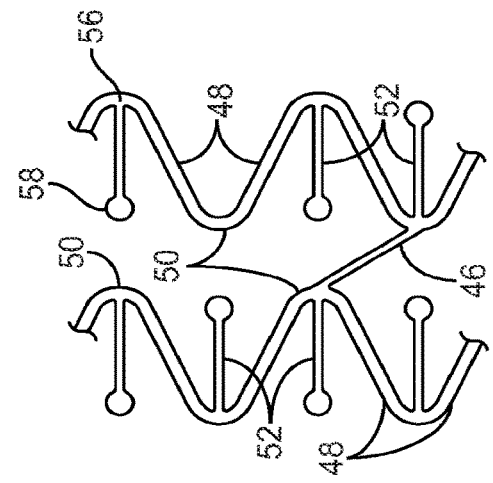
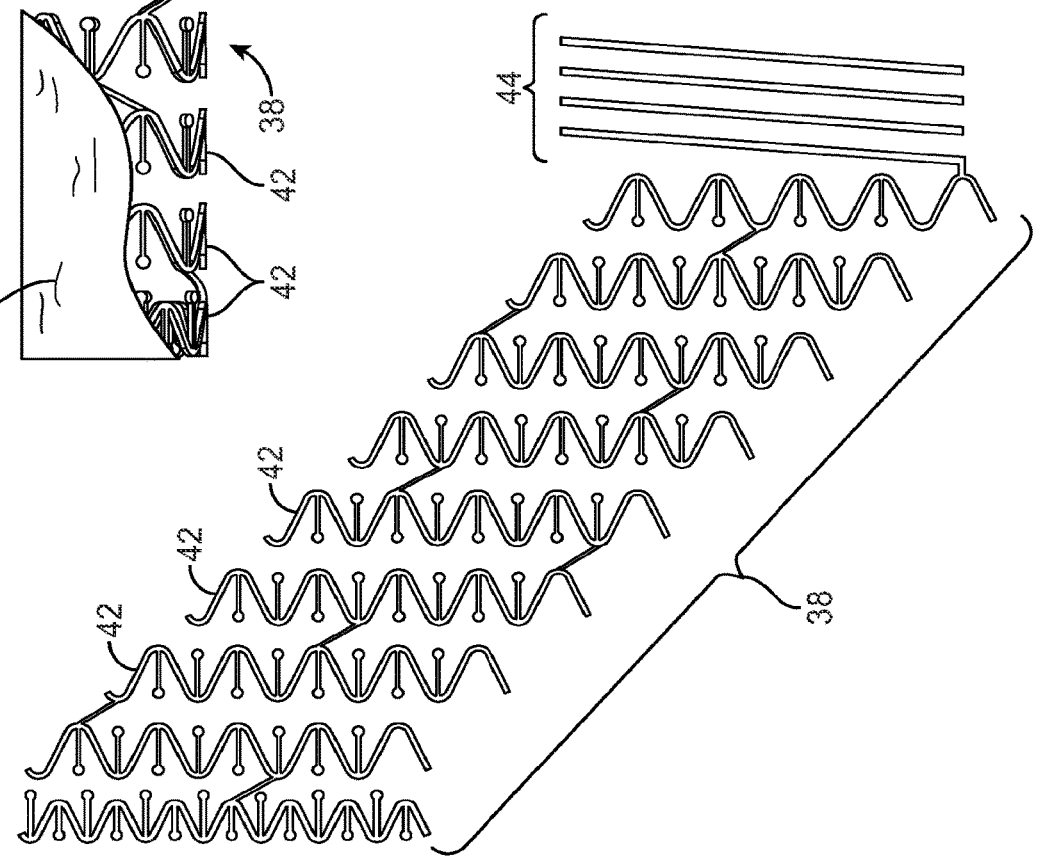
FIG. 2A
FIG. 2C
FIG. 2B

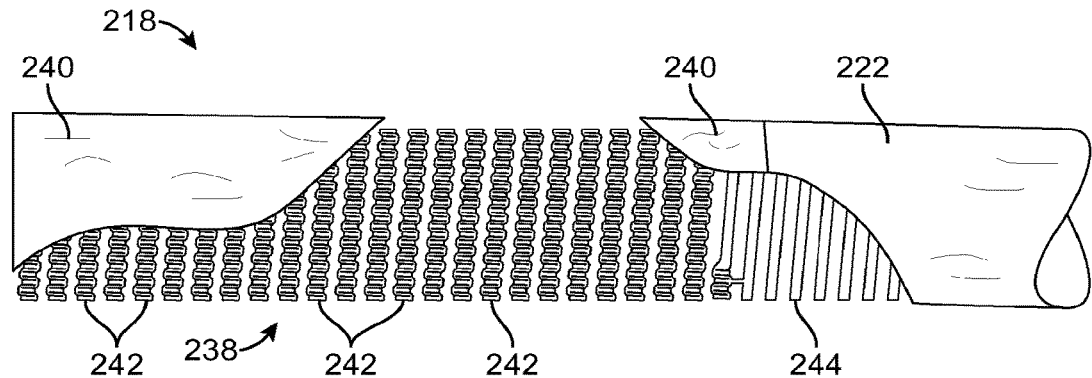
FIG. 11A
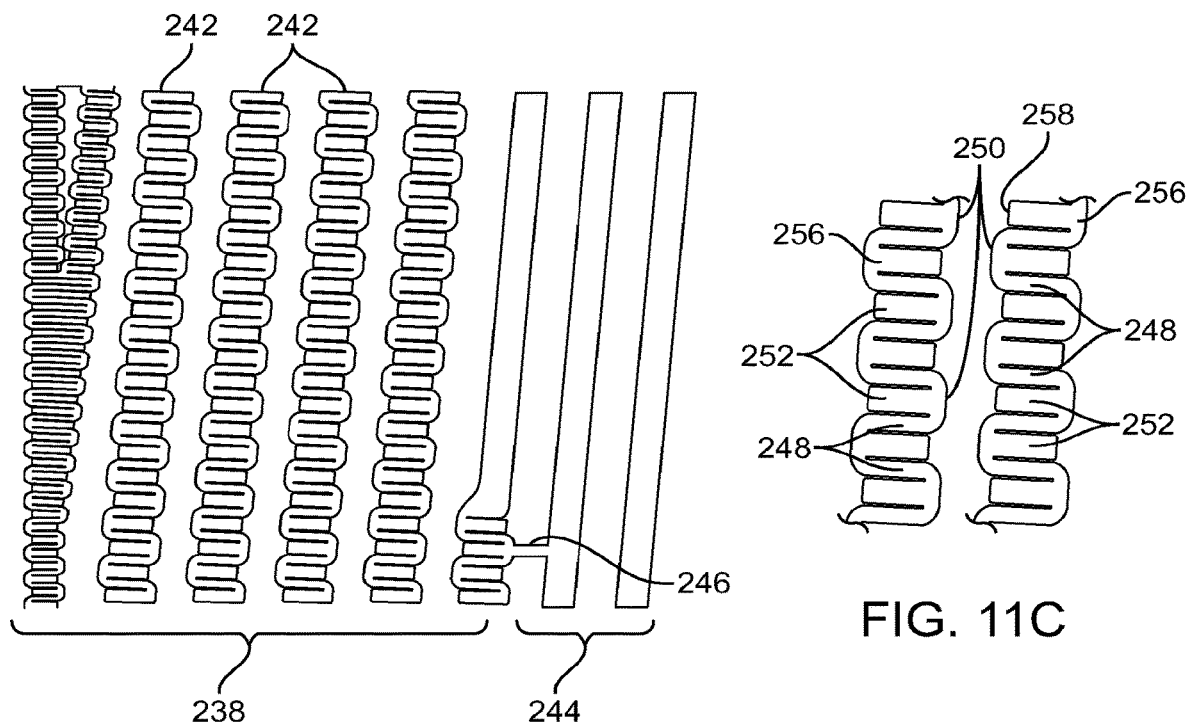
FIG. 11B
FIG. 11C

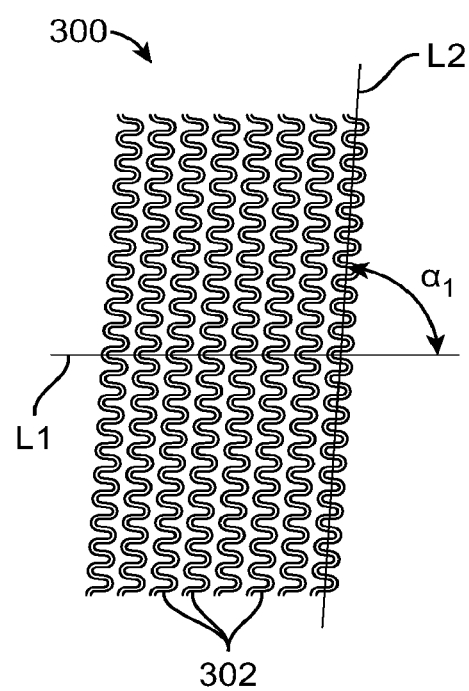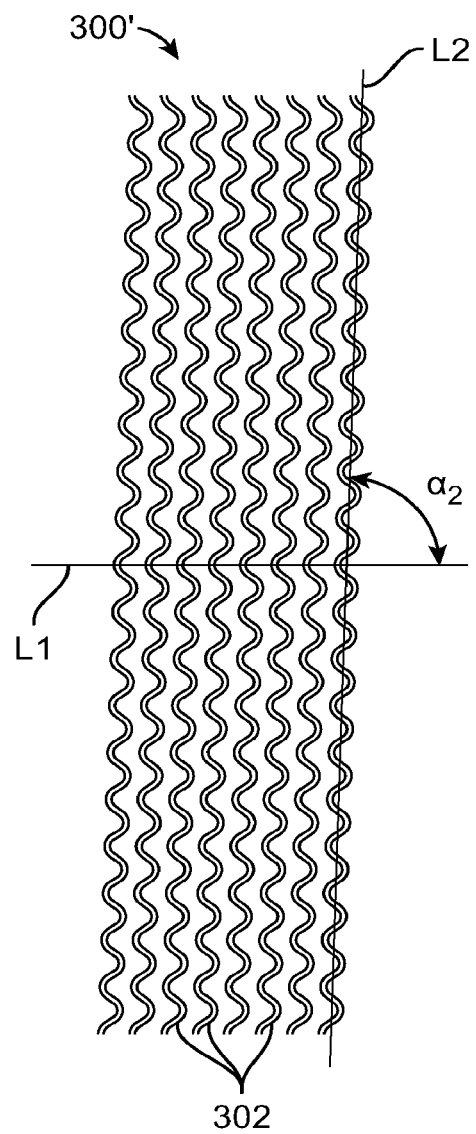
FIG. 14A
FIG. 14B

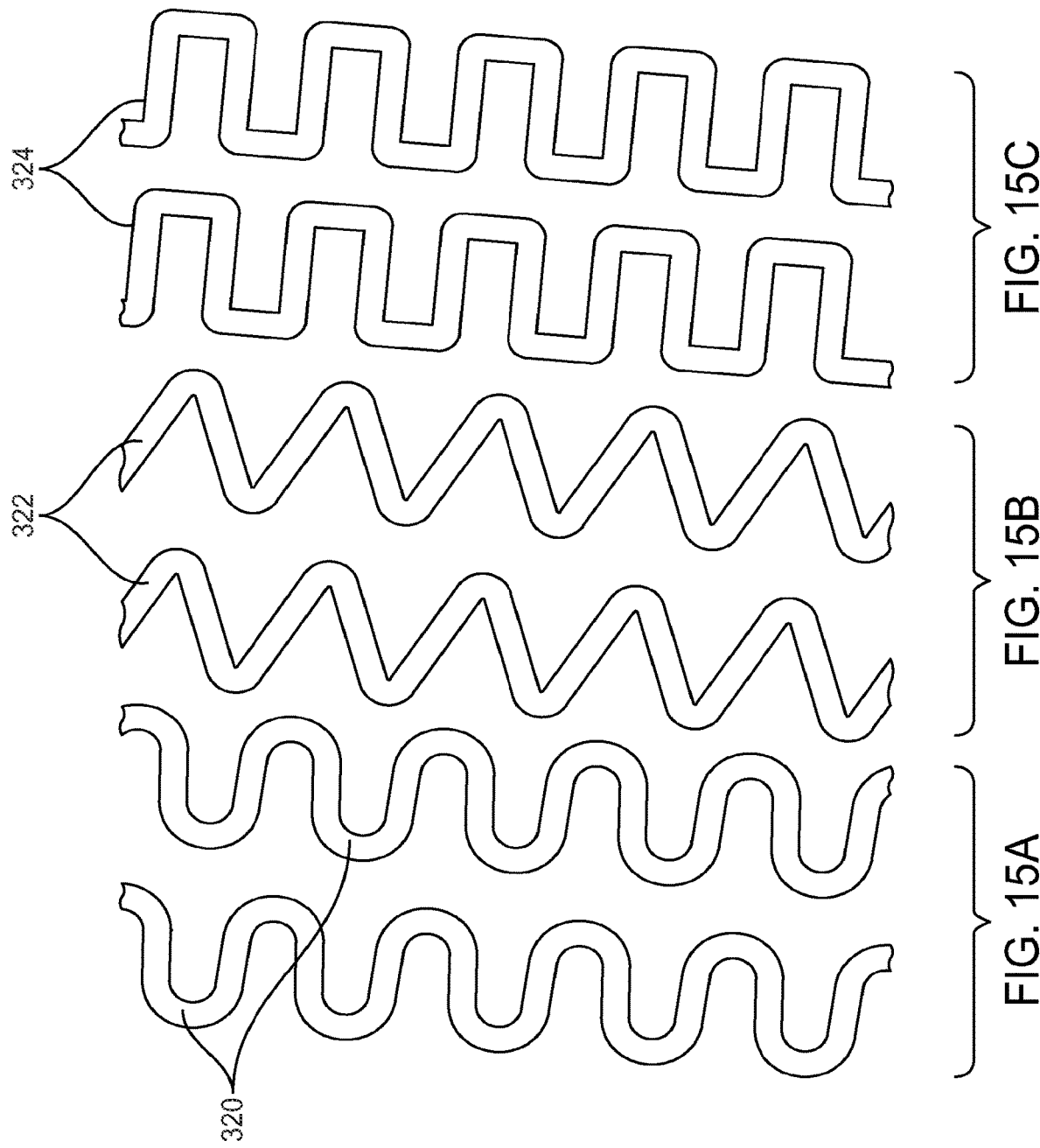

ASPIRATION CATHETERS WITH EXPANDABLE DISTAL TIP

CROSS-REFERENCE

This application is a continuation of PCT Application No. PCT/US23/16449, filed Mar. 27, 2023, which claims the benefit of U.S. Provisional No. 63/324,540, filed on Mar. 28, 2022; U.S. Provisional No. 63/327,326, filed Apr. 4, 2022; and U.S. Provisional No. 63/487,773, filed Mar. 1, 2023, the entire contents of each being incorporated herein by reference.

BACKGROUND OF THE INVENTION

1. Field of the Invention

The present application relates generally to medical devices and methods for their use. More particularly, the present invention relates to apparatus and methods for removing clot from a patient's cerebral and other vasculature.

Every year millions of people worldwide suffer strokes caused by blood clots in the brain. Even when not fatal, these clots can lead to severe and permanent disability. Until recently the only means of treating patients presenting with symptoms of an occlusive stroke was pharmaceutical, in which tissue plasminogen activator (tPA) is given to the patient intravenously to dissolve the clot and restore blood flow in the brain. However, since a vascular thrombus (clot) tends to become more fibrous and/or firm up with time, the efficacy window for tPA is just a few hours after the clot first forms. Considering the time involved with recognizing an individual may be having a stroke, transporting them to the hospital, and performing the diagnosis and applying treatment, many patients' clots are too mature to respond to tPA, such that perhaps two thirds or more of stroke victims were not being significantly helped by pharmaceutical treatment.

Advances in medical technology led to the development of various mechanical thrombectomy techniques, in which the blood clot is physically extracted from the brain. Mechanical thrombectomy has the major advantage over pharmaceutical treatment in that it can remove clots many hours after the efficacy window for pharmaceutical treatment has passed and still provide benefit to the patient.

There are two primary approaches to mechanical thrombectomy, which may be used independently or in combination with each other depending on patient characteristics and physician preference. The first is to use a catheter to apply a vacuum to the clot, in a technique known as direct aspiration. The second is to use a stent retriever to snare and physically pull out the thrombus, optionally in combination with applying a vacuum to the clot through a separate aspiration catheter.

Both mechanical thrombectomy approaches have their limitations. While stent retrievers are small and flexible enough to access most clots to engage and snare the clots, their ability to snag and remove a clot varies and has limitations. In some cases, only a portion of the clot can be removed, and debris from the procedure can be released downstream causing secondary occlusions. Stent retrievers can also induce trauma to the vessel as they are dragged proximally typically in an expanded configuration pulling the clot with them, but potentially causing trauma to the vessel. The struts of the retriever scrape the endothelium off the vessel walls, creating areas more prone to generating future occlusions. Procedure time is also an issue with stent retrievers, since in addition to delivery and extraction time they typically require a significant time to settle into and secure the clot before the first removal attempt can be made. In an environment of blood-starved brain tissue, the difference in procedure times is very clinically significant on successful outcomes.

The effectiveness of aspiration catheters depends on the ability of the catheter to vacuum the clot through the aspiration lumen of the catheter, and it varies depending on the type of clot, size, location, and the catheter lumen inner diameter to extract the clot through. Although larger inner diameter aspiration catheters are desired to extract clots successful and consistently, at least some of the following continue to hamper such desired designs, such as reduced catheter flexibility, lack of ability to reach desired anatomy to extract the clots, lack of ability to resist collapse under vacuum, and/or lack of such catheters ability to access the vessel using current accessory access devices. Current aspiration catheters are limited in diameter by the size of the accessory devices used by the physician to introduce the aspiration catheter into the anatomy, for example the hemostatic valve, introducer, and guiding membrane/catheter, and are limited by their ability to navigate and reach the clot location. As a result, many aspiration catheters today for neurovascular occlusive stroke for example typically have an inner diameter of about 0.072". Since most clots tend to be significantly larger than the aspiration catheter size, the small size of conventional aspiration catheters represents a challenge to successful aspiration, due to their inability to fully aspirate the clot on the first vacuum attempt or at all and in the absence of breaking or fragmenting the clot.

In order to enhance the suction force and still be able to fit within the access devices, some neurovascular occlusive clot aspiration catheters to retrieve clots were developed to have a larger lumen diameter such as the 0.088" aspiration catheters. However, these catheters tend to be more bulky and less deliverable, compromising their ability to reach many clot locations and/or take longer time to reach the clot location.

Because of their bulkiness, current aspiration catheters often have limited ability to navigate the tortuous anatomy of the brain to reach the common target occluded segments. Such catheters are even less successful in reaching the more distal clots due to the bulky size of these catheters and the very tortuous neurovascular anatomy. Smaller aspiration catheters designed specifically to be more deliverable and/or access the more distal clots often fail to extract the clot due to lack of sufficient suction force at the tip due to the small tip area, and/or because the aspiration lumen of the smaller catheters is too small/narrow to absorb or extract the clot.

In order to enhance deliverability and fit within the accessory devices, while maintaining an ability to retrieve larger clots, many clot aspiration catheters have an expandable distal tip that provide a larger distal opening an a reduced-size body. While generally an improvement, such expandable tips can collapse when negative pressure (vacuum) is applied to draw in the clot thereby compromising their ability to extract the clot.

To reduce the risk of collapse, some expandable tips have been reinforced with expandable metal and other scaffolds, but even with such reinforced scaffolds, the expandable segment of the aspiration catheter can still substantially deform or collapse in response to the applied negative pressure (vacuum) in the expanded configuration, and/or it becomes stiffer thereby its deliverability is compromised, and/or is prone to deformation or kinking when advanced into the anatomy in the as delivered configuration compromising the integrity of the aspiration lumen.

What is needed is a device that is capable of being flexible in the delivery configuration to enhance deliverability thereby reaching clots in the anatomy containing a clot such as the brain in the proximal and distal neuro anatomy or other vascular anatomy, a device able to remove clots without fragmenting or without substantially fragmenting the clot, a device able to remove clots without causing secondary occlusions, a device able to remove clots reliably without requiring the use of a stent retriever or other supplementary device, a device able to reach the occlusion and retrieve the clots quickly, a device that does not scrape or otherwise induce trauma to the vessel wall at any point during the procedure, a device that is successful in retrieving the clot during the first aspiration attempt, a device that can capture fragments breaking off from the original clot, a device having an expandable distal tip that in the expanded configuration resists deformation substantially maintaining the aspiration lumen configuration in the expanded configuration under vacuum when aspirating a clot, and/or a device having an expandable tip that resist collapse in the expanded configuration even when exposed to high vacuum pressures during aspiration of a clot, a device that resist deformation or kinking in the as delivered configuration when navigating vascular anatomy, a device that is contractible to a smaller configuration after being expanded to the expanded configuration, and/or a device having an expandable distal tip aspiration lumen wherein the distal tip aspiration lumen is configured to maximizes the lumen area or configuration in the expanded configuration. The present invention will address at least some of these needs.

2. Listing of the Background Art

Relevant patents and applications include US2022/0125450 and Ser. No. 18/156,921, commonly owned with the present application, the full disclosures of which are incorporated herein by reference. Other relevant patents and patent publications include US2015/0359547; WO2021/016213; U.S. Pat. No. 8,858,497; US2019/0328411; U.S. Pat. No. 8,075,510; US2018/235644; US2017/333060; US2011/152920; US2010/174290; US2011/160761; US2019/0381221; US2020/0121334; WO2019/115809; WO2019/212984; WO2018/132387; WO2016/113047; WO2020/079082; WO2020/099386; WO2017/074721; US2015/0305756; US2017/0265878; US2018/0193043; U.S. Pat. Nos. 10,231,751; 10,500,047; US2021/0153883; U.S. Pat. No. 10,792,056; and US2007/005103.

SUMMARY OF THE INVENTION

In a first aspect, the present invention provides an aspiration catheter, such as but not limited to a cerebral aspiration catheter, a coronary aspiration catheter, an arterial aspiration catheter, or a venous aspiration catheter, which comprises a tubular catheter body having a proximal end, a distal end, and an aspiration lumen extending therebetween. The aspiration catheter has an expandable distal tip with a central passage (or a passage) contiguous with the aspiration lumen of the tubular catheter body. An expandable supporting structure is attached to, embedded within, or otherwise coupled to the expandable distal tip of the tubular catheter body. In some instances, the expandable supporting structure may be attached to an outer or inner surface of an expandable membrane, but more often will be embedded or laminated within an expandable membrane, such as a polymeric membrane comprising one, two, three or more layers and being composed of one, two, three or more polymeric materials or other materials.

The phrase "distal tip" as used herein and in the claims refers to a length or region at the distal end of the aspiration catheter. The distal tip will typically be constructed differently than a proximal region or shaft of the aspiration catheter. In particular, the distal tip will typically be configured to expand from a small diameter or from low-profile configuration or from as delivered configuration or from a delivery configuration to a large diameter or to a larger configuration or to an expanded configuration or to a deployed configuration, or to an enhanced extraction configuration, which has a larger clot aspiration force or clot extraction force when a vacuum is applied at a proximal end of the aspiration catheter and the distal tip is engaging a clot, wherein the expanded (or deployed) configuration of the distal tip remains substantially the same (or remains substantially expanded or deployed) when the vacuum is applied, thereby resisting collapse, typically being balloon expandable but sometimes being self-expanding. In contrast, the proximal region or shaft will typically have a fixed diameter along its length. The fixed diameter of the proximal region or shaft may be constant or may vary along its length. The distal tip in the as delivered configuration maybe a first clot extraction configuration while the expanded configuration maybe a second clot extraction configuration wherein the second clot extraction configuration has a larger extraction force than the first clot extraction configuration. In other examples, the expanded configuration maybe the clot extraction configuration or maybe the preferred clot extraction configuration as it typically has enhanced clot extraction force. The distal tip typically terminates at the distal end of the aspiration catheter.

The supporting structure is typically in the form of a scaffold and is configured to permit radial expansion of the expandable membrane, typically by the application of a radially outward expansion placed within the supporting structure using a balloon or other expandable member, and is configured to enhance collapse resistance of the expandable membrane, particularly when the distal tip is engaging a clot (or blocked or plugged with clot) and a vacuum is being applied through the aspiration lumen, i.e., resist or prevent collapse of the expandable membrane or prevent a decrease in the lumen configuration of the expandable membrane, after expansion of the expandable supporting scaffold to the expanded configuration, or the supporting scaffold substantially maintain the expanded lumen configuration of the expandable membrane, when a vacuum is applied at a proximal end of the aspiration lumen while engaging a clot).

The supporting structure typically comprises a plurality of radially expandable rings arranged along a longitudinal axis with gaps therebetween (forming circumferential gaps between adjacent rings). The radially expandable rings will typically comprise circular, square, rectangular, oval, helical or other looped ring elements, where the looped ring elements are configured to non-elastically elongate (along their curved lengths) to permit circumferential expansion of the distal tip. Exemplary ring elements can be formed as serpentine, zig-zag ring, box (square or rectangular), diamond, or other patterns comprising bends that non-elastically open in response to a radially outward force supplied by a balloon or other expandable deployment member or structure. Exemplary rings maybe open cell design, closed cell design, combination of open and closed cell designs, or other.

Exemplary ring designs maybe formed from a tubular body, a bent wire, a patterned sheet rolled up into a tube, or printed, or other.

Exemplary open cell supporting structures may comprise serpentine and zig-zag ring patterns comprising struts joined by crowns, where the crowns comprise the "bends" which non-elastically open to allow radial and circumferential ring expansion. While every circular or circumferential ring may have an even or odd number of crowns and struts, each side or face of the ring may have even or odd number of crowns. Each ring (including terminal ring(s)) preferably has at least 14, 17, 12, 26, 30, 32, 34, 38, 40, 42, 60, 80, 100, 120, 140, 161, 160, 180, 200, or more crowns as counted on both side/face of the ring. For example, when a ring is referred to as having 14 crowns, the total number of crown when counting both sides or faces of the ring is 14. Higher crown numbers of 60, 80, 100, 120, 1400, 1600, 180, 200, and 400, and above are preferred when the supporting structure does not include additional supporting elements or when the supporting structure cells within a ring, or cells within a plurality of rings, or cells within each ring include a few supporting elements or include at least some but not all supporting elements, as described below. Fewer crown numbers, such as 14, 22, 26, 30, 32, 34, 38, 40, 42, 48, 60, and 80, are usually sufficient when the supporting structure includes at least some, or substantial number of supporting elements per ring, per at least some adjacent rigs, or per each ring of the expandable tip. The number of crowns per ring, or per at least some adjacent rings, or per the rings along the length of the expandable supporting structure is configured to allow the expandable supporting structure to expand to the expanded configuration.

It has been found that both (1) a higher number of crowns or other bends in the absence of supporting elements and (2) a lower number of crowns in combination with supporting elements will enhance circularity of the rings in the distal tip in both the as delivered configuration and the as expanded configurations, maximizing available aspiration lumen area. The phrase "number of crowns or bends per ring" refers to the total number of crowns or bends as counted in a single 360° turn about each ring. While the number "number of crowns or bends per ring" will usually be constant for each ring in an open cell supporting structure, in some instances the number may vary from ring to ring. Enhanced circularity of the distal tip (expandable supporting structure and expandable membrane) in the expanded configuration can increase the aspiration lumen area, increase the vacuum force, resist lumen collapse and deformation when a vacuum is applied at a proximal end of the aspiration lumen and the distal tip is engaging a clot (or when the distal tip is blocked or plugged with clot or other substances). Furthermore, enhanced circularity resist deformation and/or kinking of the expandable distal tip in the as delivered configuration when the catheter is advanced into the vasculature. Maximizing circularity of a ring maybe further enhanced by having a small cell period and/or small cell amplitude. In a preferred example, the expandable supporting structure comprises a plurality of rings wherein at least some rings, preferably substantially all rings are configuration to have a large number of crowns, a small cell period, and a small cell amplitude, to have an enhanced circumferential circularity.

In a preferred ring pattern, such as a serpentine patterns for example, comprising struts joined by crowns, the ratio of (1) the number of bends, e.g. crowns, crowns per ring to (2) the circumference (perimeter) of the ring measured in millimeters (mm) is typically at least 3 crowns or bends per mm of circumferential length, frequently being at least 4 crowns or bends per mm of circumferential length, usually in a range from 3 to 18 crowns or bends per mm of circumferential length, typically from 4 to 15 crowns or bends per mm of circumferential length, and most preferably ranges from 4 to 12 crowns or bends per mm of circumferential length. An increased number of crowns or bends or a high ratio of crown or bends per circumference length in each ring (or in some instances in most rings or in other instances in a plurality of rings) improves circularity of the distal tip (including the expandable supporting structure and the expandable membrane) in the expanded configuration, increases aspiration lumen area or maximizes lumen area, enhances vacuum force, and resist collapse of the distal tip when a vacuum is applied to the proximal end of the aspiration lumen and the distal tip is engaging a clot. In addition, the higher number of crowns or crowns to circumference length ratio increases the resistance to collapse of the distal tip comprising the expandable membrane and expandable supporting structure when a vacuum is applied at a proximal end of the aspiration lumen and the distal tip is engaging a clot (or blocked with clot or other substances). Furthermore, having a small cell period, enhances circularity further. In addition, having a small cell amplitude may further enhance circularity.

For example, in embodiments comprising supporting structure comprising supporting elements, 40 crowns per ring in the as delivered 2 mm outer diameter expandable tip will typically be sufficient to maintain circularity after expansion while 60, 80, 100, or more crowns per ring may be needed to provide equivalent support with supporting structures which do not include supporting elements. Thus, the number crowns per ring in as delivered supporting structures having a 2 mm outer diameter for example including supporting elements will typically range from 30 to 75, preferably from 40 to 75, and more preferably from 50 to 60. The range for rings not having supporting structures will be from 60 to 150, preferably from 70 to 120, more preferably from 100 to 120. The ratio of number of crowns to circumference in mm for embodiments including supporting elements will range from 3 to 10, preferably from 4 to 9, more preferably from 4.5 to 8, and most preferably from 5 to 7, while the ratio of crown number to circumference (measured in mm) for embodiments without supporting elements will range from 5 to 18, preferably from 6 to 12, more preferably from 8 to 12, and most preferably from 10 to 12.

Exemplary closed cell supporting structures may comprise "box" structures joined end-to-end by links in circular, helical or other patterns. Typically, the boxes will be joined by circumferential links to form circular rings which are in turned joined by axial links to form the supporting scaffold or other supporting structure. Alternatively, the circumferential links may be arranged in a helical or spiral pattern to form a continuous series of rings, preferably without additional axial links or attachment points.

While the boxes will typically be square, diamond, or rectangular, boxes may have any closed polygonal structure which includes a plurality of straight (or sometimes curved) sides joined by bends. In some instances, circular and oval closed shapes could also be considered boxes within the scope of the present invention. Such box structures will be configured to circumferentially elongate (expand) when a radial opening force is applied inside of the supporting structure in the distal tip of an aspiration catheter.

In a preferred example, the expandable distal tip comprising the expandable supporting structure has an outer diameter in the as delivered configuration of about 1 mm, 2 mm, 3 mm, 4 mm, or of about 5 mm, or the expandable distal tip comprising the expandable supporting structure has an outer diameter in the as delivered configuration ranging from 1 mm to 5 mm. In other examples, the distal tip comprising the expandable supporting structure has an outer diameter in the as delivered configuration of about 7 mm, 8 mm, 9 mm, or of about 10 mm. Typically, the distal tip has a cylindrical shape in the as delivered configuration. In some other examples, the distal tip may have other shapes such as funnel, cone, an oblong, oval, or other shapes, in the as delivered configuration. In yet another example, the distal tip comprising the expandable supporting structure wherein the distal tip has cylindrical shape, oblong shape, oval shape, cone shape, funnel shape, or other shapes, in the expanded configuration, wherein the distal tip outer diameter in the expanded configuration ranges from 2 mm to 10 mm, preferably ranges from 3 mm to 8 mm, and more preferably ranges from 3 mm to 7 mm. The outer diameter of the distal tip may vary along the length or about the circumference of the distal tip or may be fixed or constant along the length or about the circumference of the distal tip.

In some instances, the scaffold or other supporting structure will also include supporting elements, which will help support spaces which open in in the support structure as the support structure is being expanded. For example, in a support structure including serpentine rings comprising crowns and struts, as the rings expands, the struts will spread apart and leave unsupported spaces or gaps therebetween. The gaps between adjacent rings will also be unsupported spaces, both before and after the supporting structure is radially expanded. The membrane will lack support in those gaps, and the circularity and/or crush strength (crush resistance) of the expanded distal tip will both decrease. Additionally, such unsupported regions of the membrane will be at increased risk of invagination (collapse or partial collapse of the membrane and/or expandable supporting structure) when a negative pressure is applied to the aspiration lumen of the catheter when a clot is engaged, particularly when the open distal tip is partially or totally occluded with clot, or when the expandable tip is delivered to the vasculature in the as delivered configuration.

The supporting elements of the present invention will be configured to fill as many of the open space within a ring. In contrast, the spaces or gaps between axially adjacent rings will preferably be free from supporting elements (although axial links and other portions of the supporting structure will usually be present in some examples while in other examples the spaces or gaps between axially adjacent rings maybe free from any supporting elements or attachment points and free from any portions of the supporting structures). The spaces between adjacent rings should have minimum number of supporting structure, if any, in order to enhance flexibility, particularly in the unexpanded delivery configuration.

In certain examples, in the unexpanded, delivery configuration, the supporting elements of the present invention will cover or fill from 50% to 98% of the unsupported area within each ring, preferably from 65% to 95%, more preferably from 75% to 95%, and most preferably from 80% to 95%. In contrast, in the expanded configuration (i.e., after deployment in a blood vessel), the supporting elements of the present invention will cover or fill from 10% to 85% of the unsupported area within each ring, preferably from 15% to 85%, more preferably from 20% to 85%, and more preferably from 40% to 85%.

Preferred supporting elements will be "cantilevered" from the ring and be configured to fill or to support the openings or gaps within an "axial width" of a ring, usually remaining outside of the gaps and spaces between adjacent rings in order to support the distal tip after it has been radially expanded, without significantly reducing flexibility of the distal tip as it is being advanced into the vasculature, or without reducing flexibility of the distal tip as it is being advanced into the vasculature, or while maintaining the flexibility of the distal tip as it is being advanced into the vasculature. Exemplary supporting element having a base (proximal) end and a free (distal) end. The base end is usually attached to one of the radially expandable rings (e.g., to a ring structural element, such as a crown or a strut) and the free end is often oriented toward the gap between adjacent rings, usually not extending into the gap between adjacent rings in the as delivered configuration. In a preferred example, the expandable supporting structure comprises a plurality of supporting elements within each ring each having a width, a length, and thickness, sufficiently to support unsupported spaces (or region) within said ring, to prevent collapse or invagination (partial collapse) of the unsupported region, when a vacuum is applied to extract an engaged clot at the distal end of the aspiration catheter. In another example, the expandable supporting structure comprises a plurality of circumferential rings wherein at least some rings comprise a plurality of supporting elements configured to resist collapse or resist invagination of the unsupported region when a vacuum is applied at a proximal end and a clot is engaging the distal end of the aspiration catheter. In yet another example, the expandable supporting structure comprises a plurality of circumferential rings wherein at least some rings comprise at least some supporting elements configured to resist collapse or resist invagination of the unsupported region when a vacuum is applied at a proximal end and a clot is engaging the distal end of the aspiration catheter.

In some cases, the supporting elements may extend into an adjacent gap between adjacent rings even prior to radial expansion of the distal tip, but preferably most or all of the supporting elements are configured to be recessed (or confined) within an axial width of the ring (or within an amplitude of a ring cell) prior to ring expansion and will extend further, protrude further, or emerge towards the adjacent gaps between adjacent rings or into the adjacent gaps between adjacent rings as the distal tip is radially expanded (or only after radial expansion of the distal tip, or during the radial expansion of the distal tip). It has been found that presence of the supporting structures in the gap between adjacent rings prior to distal tip expansion will reduce tip flexibility during advancement in the vasculature prior to distal tip deployment. Such loss of flexibility is undesirable.

The use of such "cantilevered" supporting elements as "supporting of unsupported regions or gaps located within rings axial width" which are deployed to enhance support of the expandable membrane after deployment of the distal tip without increasing stiffness of the distal tip during delivery (introduction and advancement) of the aspiration catheter into and through the patient's vasculature. Use of the supporting elements also allows increased expansion of the distal tip (thus increasing the available aspiration lumen diameter) while resisting collapse when a vacuum is applied at a proximal end of the aspiration lumen. In another example, the supporting elements deploy (or protrude, or extend further) towards a gap between two adjacent rings, or deploy into a gap between two adjacent rings, as the distal tip is expanded (or after the distal tip expansion) to enhance support of the expandable membrane after deployment of the distal tip without increasing stiffness of the distal tip during delivery (introduction and advancement) of the aspiration catheter into and through the patient's vasculature.

The supporting elements may have various shapes and configurations such as I, T, U, M, Z, curved shaped, straight shaped, or other shapes and configuration to support or to enhance support of the unsupported segments of the expandable membrane, preferably without increasing stiffness of the distal tip. The free end may have a flat shape, rounded shape, spherical shape, or other shapes. The width of the supporting elements maybe the same along the length of the supporting elements or different. The supporting elements may be tapered, either increasing or decreasing in width in a direction from the attached base end to the free distal end.

In a preferred instance, the dimensions of the supporting elements will preferably be selected to fill or occupy as much of the unfilled spaces or gaps within any given ring (but usually not between adjacent rings) in the supporting structure which may exist prior to expansion. For example, gaps between struts joined by crowns on a ring may be filled with supporting elements cantilevered from the inside curve of the crown, as illustrated in many embodiments herein. The cantilevered supporting elements can be patterned fill virtually the entire space between the struts, leaving only cuts or very small separating lines therebetween. By maximizes the area of the supporting element prior to expansion, coverage of the gap which is created after expansion is also maximized between the struts after the ring is expanded. In a preferred example, the width of the supporting elements at the attached base end is approximately equal to or larger than the width of the structural element (e.g., strut, crown, or link) to the location at which the supporting element is attached.

While the supporting elements and the expandable supporting structure are typically formed from the same material, in some instances they be formed from different materials or types of materials, e.g., (1) one may be formed from a metal and the other from a polymer or (2) one may be formed from a metal or a polymer and the other from a different metal or a different polymer.

In another preferred example, the supporting elements are recessed in space between structural elements of the rings, e.g. in space between struts joined by crowns, so that the distal ends of said supporting elements do not extend substantially beyond peaks of adjacent crowns or other structural element into the gaps between adjacent rings in the as delivered configuration.

In specific examples, the supporting elements may have one base end and one free end, two free distal ends, three free distal ends, or more.

In another example, the supporting elements may have two or more base ends attached each to one or more structural element on one ring (the same ring). Such supporting elements may have one, two, three, or more distal free ends.

In another example, the supporting elements may be bisected to have at least two base ends, each base end being attached to a different structural element on a single ring. The base ends of the supporting element may be attached to an axially inner or to an axially outer surface of a ring or of a ring's structural elements comprising a crown, a strut, or a link.

In specific examples, the radially expandable rings are arranged within a cylindrical "envelope" prior to expansion. The cylindrical envelope is a virtual space having an inner generally cylindrical surface and an outer generally cylindrical surface and an annular volume therebetween, where the radially expandable rings will be dimensioned and arranged to lie within this space prior to expansion. Usually, the supporting elements are also configured to lie within this virtual cylindrical envelope prior to expansion of the rings. The cylindrical envelope may have a diameter greater than, equal to, or smaller than that of the tubular catheter body prior to expansion.

In specific examples, the distal tip of the expandable supporting structure may be configured to expand into a cylinder, a cone, or a combination thereof after expansion to an expanded configuration. In a preferred example the distal tip of the expandable supporting structure maybe configured to expand from a cylindrical configuration to an expanded cylindrical configuration, to an expanded cone shaped configuration, or to an expanded cone shaped distal tip configuration to maximize or to enhance the suction force when a vacuum is applied at a proximal end of the aspiration lumen. In another example, the distal tip of the expandable supporting structure maybe configured to expand from a cylindrical configuration in the delivery configuration to a substantially cylindrical shaped configuration after the expandable supporting structure is expanded to an expandable configuration, wherein the expanded configuration is larger than the delivery configuration, or wherein the expanded configuration is larger than the as delivered configuration by a range from 1.1 to 4 times larger, preferable 1.3 to 3 times larger. In yet another example, the distal tip of the expandable supporting structure is configured to expand from a cylindrical configuration to an expanded cone shaped configuration, at a proximal segment of the distal tip, and is continuously connected to an expanded cylindrical shaped configuration distal to the expanded cone shaped configuration. In still other configurations, the expanded configuration may be a combination of a long conical proximal base (there will usually be at least a short conical portion at the proximal end) attached to the proximal end of the shaft and a distal cylindrical portion. A number of specific configurations are illustrated in the figures.

In specific examples, the expandable supporting structure is configured to expand in response to expansion of a balloon catheter within the expandable supporting structure. The balloon catheter maybe configured to be delivered together with the aspiration catheter comprising the expandable supporting structure at the distal end, typically said balloon catheter being delivered together along with the aspiration catheter, within the aspiration lumen of the aspiration catheter, wherein after the distal end of the distal tip of the aspiration catheter is positioned adjacent to a clot, the balloon catheter is expanded to expand the expandable supporting structure to an expanded configuration, and is then deflated and withdrawn out of the aspiration catheter prior to applying a vacuum at a proximal end of the aspiration catheter to extract the clot. In another example, the balloon catheter is delivered to the distal end of the aspiration catheter after the aspiration catheter is delivered to and positioned adjacent to a clot, wherein the balloon catheter is advanced through the aspiration catheter until the balloon reaches the expandable distal tip segment or reaches the expandable distal tip, then it is expanded to expand a distal tip segment of the aspiration catheter and is then deflated and removed from the aspiration catheter and a vacuum is applied at a proximal end of the aspiration catheter to remove (extract) the clot. In another example, an expansion catheter having an expandable member at a distal end of said catheter, said expandable member is expanded, to expand an expandable distal tip comprising an expandable supporting structure (scaffold) and an expandable membrane, wherein the distal tip is incorporated into or coupled to the distal end of an aspiration catheter wherein the expandable member comprises a balloon, a scaffold, a cage, or other structure capable of expanding to expand the expandable supporting structure from an as delivered configuration to an expanded configuration. The expandable member maybe polymeric, metallic, or other material wherein said member being expandable from an as delivered configuration, a crimped configuration, or a deflated configuration to an expanded configuration. While the distal tip may be fully expanded along its entire length, often only a portion of the length of the distal tip may be expanded by the balloon or other expandable member depending on the patient anatomy or other circumstances. The portion of the distal tip that is expanded can be controlled by adjusting the length of the balloon present in the distal tip during expansion and/or selecting an expansion balloon having a different length.

In a preferred example, the expandable supporting structure of the distal tip of the aspiration catheter is formed from a deformable material, preferable plastically deformable material. In a preferred example, the expandable supporting structure is formed from a plastically deformable metal or metal alloy. In a specific example, the expandable supporting structure is formed from a metallic material comprising stainless steel alloy, cobalt chrome alloy, platinum chromium alloy, or other metal or metal alloy.

The expanded shape of the supporting structure will usually be determined by the shape of the balloon or other expanding structure, i.e., expansion of a cylindrical balloon within the plastically deformable supporting structure will impart a cylindrical shape to the distal tip while expansion of a conical balloon will impart a conical shape to the distal tip.

In some less preferred examples, the expandable supporting structure may be configured to self-expand when released from radial constraint. The radial constraint may be positioned over the expandable supporting structure. In other example, the radial constraint may be positioned within the expandable supporting structure (inner lumen) and is configured to release the expandable supporting structure in-vivo, to allow expansion of the expandable supporting structure. The expandable supporting structure in one example is formed from a shape memory material such as NiTi nitinol or other shape memory material.

The supporting elements may have any one or more of a variety of shapes and attachment locations on the expandable structure. For example, the supporting elements may extend, in an axial direction to the radially expandable rings, towards the gap between adjacent rings, or extend into the gap between adjacent rings. In other examples, the supporting elements may extend in a circumferential direction to the radially expandable rings, typically attached to the outwardly curved surfaces of the crowns (peaks), extending circumferentially into an adjacent gap. In other examples, the supporting elements may extend in a axial direction to the radially expandable rings into the gap contained within or bounded by a ring's axial width, or is contained within or bounded by the space between structural elements of each ring or of said ring, typically attached to the curved surfaces of the crowns. In still other examples, at least some of the supporting elements may comprise any one or more of linear and/or non-linear segments, may have expanded tips (forming contact pads as discussed hereinafter) at the free end. In some examples, the supporting elements may branch into two or more segments in a direction toward the free end. The supporting elements may have the same or different lengths or widths. In some specific examples, the supporting elements may have a length equal to or less than a length of an adjacent strut length in the as delivered configuration. In other examples, the supporting elements may have a length equal to or less than the ring cell amplitude in the as delivered configuration, or less than 1 time the ring cell amplitude in the as delivered configuration. In yet another example, the supporting elements may have a length equal to or less than the length of the ring period in the as delivered configuration. In other examples, the supporting elements may have a length greater than the ring cell amplitude only in the expanded configuration.

In some examples, the supporting elements are attached to one or more of axial inner crown regions, axial outer crown regions, struts, mid strut, or attached to axial or circumferential links.

In some preferred examples, at least some of the radially expandable rings comprise a serpentine, zig-zag, box, diamond, or other pattern including struts joined by crowns, and at least some of the adjacent rings are joined in one or more locations by axial links or attachment points using soldering, bonding, or fusing crown on adjacent rings for example, or as patterned. Alternatively, at least some of the adjacent rings maybe joined end-to-end in a helical arrangement free from axial links or attachment points, and wherein preferably the amplitude on the at least some rings is fixed within each ring. In a preferred example, at least two adjacent rings, or at least some adjacent rings, of the expandable supporting structure distal tip have no more than two links or two attachment points joining said at least two adjacent rings (or joining said at least some adjacent rings). In another example, the comprises a plurality of circumferentially expandable rings including struts joined by crowns, wherein one or more adjacent rings being axially separated by gaps and being unconnected, typically the one or more unconnected adjacent rings are located at the distal end of the distal tip of the aspiration catheter, and are held together by an expandable membrane attached to the one or more adjacent unconnected rings providing the distal tip enhanced flexibility in the as delivered configuration and allowing the one or more rings to expand from an as delivered configuration to an expanded configuration. In a preferred example, an expandable supporting structure comprising a plurality of adjacent expandable rings wherein along a length of said expandable structure, adjacent rings have two or less connections or attachment points joining said adjacent rings, preferably adjacent rings have one connection or attachment point joining said adjacent rings, wherein the length is the entire length of the expandable structure, or a segment along the axial length of the expandable structure, wherein the segment comprises two or more rings. In yet a preferred example, the expandable supporting structure comprising a plurality of adjacent rings joined end to end in a helical arrangement to enhance flexibility of the aspiration catheter to navigate tortuous anatomy in the as delivered configuration. The adjacent rings in this example are not joined by links or attachment points on the adjacent rings, and the at least some adjacent rings each has fixed (or constant or same) ring cell amplitude, preferably all the at least some rings have the fixed (or constant or same) ring cell amplitude. In this example, at least some rings maybe patterned into an open cell pattern, a closed cell pattern, or a combination of open and closed cell pattern along a length of the expandable scaffold.

Alternatively, in another example, at least some of the adjacent rings in the expandable supporting structure may be joined end-to-end in a helical arrangement. Such helical arrangements will typically comprise a "smooth" helix free from additional curves or bends, i.e. a curve formed over on a conical or cylindrical surface that would become a straight line if the surface were unrolled into a plane. In other instances, one, two, three or more additional bends, curves or other secondary non-linearities can be superimposed over the helical rings to enhance bendability of the expandable structures, particularly in their crimped or reduced diameter configurations during delivery. Such one, two, three or more additional bends, curves or other secondary non-linearities may be formed from an expandable supporting structure or a non-expandable structure. In a specific preferred example, the expandable supporting structure forms a helical coil.

In other preferred examples the expandable membrane may comprise an elastic membrane, or an in-elastic membrane (stretchable membrane). The elastic and/or in-elastic membrane may comprise one or more elastomers, polymeric material, or other material. In a preferred example, the expandable membrane is selected from a group consisting of NeuSoft UR862A, NeuSoft UR852A. NeuSoft UR842A, NeuSoft NEU 455-50A, NeuSoft™ 596-NeuSoft NEU 455-55A, NeuSoft NEU 455-60A NeuSoft NEU 455-65A, Tecothane AR-62A, Tecoflex EG 80A, Tecoflex EG 85A, Tecoflex EG-93A, Tecoflex TT-1074A, Tecoflex TT-1085A Tecoflex TT-18095A, Elastollan S 50 A 15SPF Elastollan S 60 A 10W Elastollan S 60 A 10WH, Pellethane 2103-70A, Pellethane 70A, Pellethane 2363-80A, Estane 2103-70A, ReZithane Rx50A, Texin RXT 70A, Chronoflex C 80A-Q, Chronoflex AL Chronoflex C 80A-Q, Polyblend 1100-75A, ResMart Ultra TPU 60A, ResMart Ultra TPU 70A, ResMart Ultra TPU 85A, ResMart Ultra TPU 90A, ResMart Ultra TPU 95A, Ecoflex 00-30, Ecoflex 00-20, Ecoflex 5A, Dragon Skin 20, Pebax 2533, Pebax 3033, chronoprene, chronothane, chronosil, polyethylene, such as LDPE, HDPE, Ultra HMWPE, or the like, Pebax such as Pebax 2533, Pebax 3533, Pebax 4033, Pebax 4533, Pebax 5533, Pebax 7233 or the like, Nylon such as Nylon 12, Nylon 6/6 or Nylon 6, Polyurethanes such as Pellethane 2363-55D, Pellethane 2363-65D, ResMart Ultra TPU 64D, ResMart Ultra TPU 72D, Fluoropolymers such as PTFE, Poly(vinylidene fluoride-co-hexafluoropropylene), Poly(vinylidene fluoride-co-hexafluoropropylene), Fluorinated ethylene propylene, Polychlorotrifluoroethylene, or the like, or combination thereof, or other elastomers, polymers, or other material.

In one example, the expandable membrane is comprised of a polymeric elastic membrane which may have isotropic properties, but in other instances may have anisotropic properties, for example the elastic membrane may have a higher elasticity in a circumferential or radial direction than in an axial direction.

In some instances, the expandable membrane may be formed by heat shrinking over or onto the expandable supporting structure such as a scaffold. In other instances, the expandable membrane may be formed by laminating the expandable supporting structure such as a supporting scaffold between two or more layers of the polymeric material such as elastomer(s) material, elastomer(s) on an outer surface and an inelastic/stretchable polymeric material on an inner surface of the expandable structure, stretchable/inelastic material on both outer and inner surface of the expandable structure, or a stretchable material on the outer surface and an elastic material on the inner surface of the expandable structure. For example, the two layers of elastomer(s), two layers one elastic and one stretchable, or two layers both stretchable may be bonded to each other over (sandwiching) the expandable supporting structure such as a supporting scaffold so that there is a seal between or bonding of the two layers as well as said two layers are sandwiching, bonding to, and/or adhering to the scaffold or other expandable structure. In another example, the expandable membrane comprising a polymeric or other material configured to stretch and/or expand from an as delivered configuration to an expanded configuration, wherein the material is configured to expand from said as delivered configuration to a larger configuration ranging from 1.1 to 5 times larger than the as delivered configuration. The expandable membrane is configured to have axial, radial, and/or circumferential stiffness to allow radial flexibility while maintaining axial push transmission. The expandable membrane is configured to allow radial expansion of the expandable supporting structure and/or allow axial movement of the expandable supporting structure rings as the rings are being expanded from the as delivered configuration to an expanded configuration.

In a preferred example, an aspiration catheter, which comprises a tubular catheter body having a proximal end, a distal end, and an aspiration lumen extending therebetween. The aspiration catheter has an expandable distal tip with a central passage contiguous with the aspiration lumen of the tubular catheter body, said expandable segment comprising an expandable supporting structure is attached to or embedded within an expandable membrane. In one preferred example, the expandable supporting structure is patterned from a tube, a bent wire, or rolled up patterned sheet. The tube, rolled up sheet, or bent wire in the preferred example are patterned into said expandable supporting structure being expandable from as delivered configuration to an expanded configuration. In some other preferred examples, an aspiration catheter, which comprises a tubular catheter body having a proximal end, a distal end, and an aspiration lumen extending therebetween. The aspiration catheter has an expandable distal tip with a central passage contiguous with the aspiration lumen of the tubular catheter body. An expandable supporting structure is attached to or embedded within the expandable distal tip of the tubular catheter body. the tubular catheter body may be reinforced with a reinforcement structure over at least a portion of its length, proximal to the expandable tip, by one or more of a coil, a scaffold, a scaffold with supporting features, or other means. In some instances, at least a portion of the catheter body reinforcement structure comprising one or more of a coil, a scaffold, or braid that may be formed continuously with the expandable supporting scaffold or other expandable supporting structure of the expandable tip. In a preferred example, the reinforcement structure and the expandable scaffold or other expandable supporting structure are formed from a patterned tube. In other example the reinforcement structure and the expandable scaffold or other expandable supporting structure are formed from a bent wire. In other instances, the reinforcement structure in the catheter body may be separately formed from the supporting scaffold of the expandable distal tip and are then coupled or joined together by one or more of solder, fusing, bonding, or weaving the structures together, overlapping them over a length segment at their interface.

In another example, an aspiration catheter, which comprises a tubular catheter body having a proximal end, a distal end, and an aspiration lumen extending therebetween. The aspiration catheter has an expandable distal end, with a central passage contiguous with the aspiration lumen of the tubular catheter body, said expandable distal end comprising an expandable supporting structure attached to or embedded within an expandable membrane. In one specific example, the expandable distal end comprising the expandable supporting structure has a length ranging from 0.5 mm to 50 cm, preferably ranging from 1 cm to 25 cm, and more preferably ranging from 2 cm to 10 cm. In yet another example, the expandable distal end may have a length spanning substantially the length of the aspiration catheter. In specific examples, the expandable distal end may have a length ranging from 50 cm to 150 cm. In a preferred example, the expandable distal end comprises an expandable distal tip wherein the distal tip comprises a segment of the expandable supporting structure attached to or embedded within an expandable membrane. In some specific examples, the expandable distal tip segment includes the expandable distal end segment. In some other instances, the expandable distal tip is the same as the expandable distal end.

In other preferred examples, at least some of the multiplicity of supporting elements may have their base ends each attached to a strut. In other preferred embodiments, at least some of the multiplicity of supporting elements may have their base ends each attached to either the inner curved surface or the outer curved surface of a crown. The supporting elements may be extending or oriented axially, circumferentially, or at other angles or directions relative to the supporting scaffold or other expandable supporting structure, supporting scaffold rings, or structural elements of the scaffold rings.

In a second aspect, the present invention provides an aspiration catheter having an alternative expandable supporting structure design. The alternative aspiration catheter comprises a tubular catheter body having a proximal end, a distal end, and a lumen extending therebetween. The expandable supporting structure is attached at or is incorporated into the distal end or to the distal tip of the tubular catheter body and has a central passage contiguous with the lumen of the tubular catheter body, and the expandable supporting structure includes an expandable membrane and an expandable scaffold or other expandable supporting structure configured to radially expand the expandable membrane. The expandable membrane is typically elastically expandable, and the expandable scaffold or other expandable supporting structure is typically inelastically expandable, i.e., the scaffold plastically deforms to and maintains an expanded shape and size in response to radial expansion by a balloon or other radial expansion tool. In this way, the expanded supporting structure "supports" the membrane in an expanded configuration.

In other instances, the membrane could be plastically or otherwise inelastically expandable while the supporting structure is elastic or inelastic, but such embodiments are generally not preferred.

The expandable supporting structure may comprise a plurality of radially expandable rings arranged along a longitudinal axis, wherein at least some of the radially expandable rings comprise "expandable cells" having bends which can plastically deform to allow radial opening of the ring. The cells may have an "open" configuration, such as U-shaped cells in serpentine rings and a V-shaped in zig-zag rings; squares, rectangular, or other regular or irregular polygons with one or more missing sides; and CƆ-shaped cells. Alternatively, cells may have a "closed" configuration, such as diamond shaped, or box-shaped cells in boxed rings, wherein the box shape can be rectangular, square or other or other regular or irregular polygonal shapes.

Supporting elements may be positioned inside or outside of an open cell. For example, the base of a cantilevered supporting element may be attached to the inside bent surface of a crown and positioned between adjacent struts in a U-shaped, V-shaped, or ω-shaped open cell. Alternatively, the base of a cantilevered supporting element may be attached to an outside bent surface of a crown and extend away from struts into a gap adjacent a U-shaped, V-shaped, or ω-shaped open cell.

Supporting elements may also be positioned inside or outside of a box or other closed cell. For example, the base of a cantilevered supporting element may be attached to an inside surface of the box and project into an interior space of the box. Alternatively, the base of a cantilevered supporting element may be attached to an outside of the box or onto circumferential links which attaches the boxes or other closed cells together to form a ring.

Typically, at least one end of a supporting elements is attached to at least one location on a strut or crown or the ring of the radially expandable rings. In some instances, however, at least some of the supporting elements may be unattached to the supporting scaffold or other expandable supporting structure and are attached or coupled only to the expandable membrane so that they will reinforce the V-shaped, CƆ-shaped, U-shaped, or square/box shaped spaces between struts to enhance resistance of the expandable membrane to collapse under vacuum/negative pressure when the distal tip is blocked or plugged with clot or other substances.

In some instances, at least some of the supporting elements may extend in a circumferential direction from the radially expandable rings into the cell space (V-shaped, CƆ-shaped, U-shaped, or square/box shaped space). In a preferred example, at least some supporting elements extend circumferentially from an outer crown region to an adjacent outer crown region, in one direction or in two opposite directions. In another preferred example, at least some supporting elements extend circumferentially from a strut to an adjacent strut, in one direction or in two opposite directions. In other instances, at least some of the supporting elements extend in an axial direction from the radially expandable rings into and/or beyond the cell space (V-shaped, CƆ-shaped, U-shaped, or square/box-shaped space). In a preferred example, the supporting features are configured to shorten when the expandable supporting structure is expanded to an expanded configuration such that said supporting features length is equal to or less than the amplitude of the expandable ring cell, or the supporting features do not extend axially beyond the peak of an adjacent crown. In another preferred example, the supporting features are configured to deploy or project further when the expandable supporting structure is expanded to an expanded configuration providing enhanced support to the expandable membrane and providing the expandable membrane enhanced resistance to collapse when a vacuum is applied at a proximal end of the aspiration lumen.

In a preferred example, the present invention provides an aspiration catheter having an expandable supporting structure design. The aspiration catheter comprises a tubular catheter body having a proximal end, a distal end, and a lumen extending therebetween. The expandable supporting structure is attached at or incorporated within the distal end (or distal tip) of the tubular catheter body and has a central passage contiguous with the lumen of the tubular catheter body, and the expandable supporting structure includes an expandable membrane and a supporting scaffold or other expandable supporting structure configured to radially expand the expandable membrane. The expandable supporting scaffold or other expandable supporting structure comprises a plurality of radially expandable rings arranged along a longitudinal axis, wherein at least some of the radially expandable rings comprise a serpentine or zig-zag or open other open pattern including struts joined by crowns forming a V-shaped, ◯-shaped, U-shaped, or open square/box shaped space therebetween. A multiplicity of supporting elements are positioned in the V-shaped, ◯-shaped, U-shaped, or square shaped space to support the membrane in said V-shaped, ◯-shaped, U-shaped, or open square/box shaped space in the as delivered configuration and/or in the expanded configuration, and wherein the supporting scaffold or other expandable supporting structure resist collapse of the membrane in said space in the expanded membrane and scaffold or other expandable supporting structure configuration when a vacuum is applied at a proximal end of the aspiration lumen and the distal tip is blocked or plugged with clot or other substances, and wherein the supporting scaffold or other expandable supporting structure being capable to contract from the expanded configuration to a smaller configuration when the aspiration catheter is withdrawn into a guiding catheter having an inner lumen configuration smaller than the expanded configuration of the supporting scaffold or other expandable supporting structure.

In a preferred example, the present invention provides an aspiration catheter having an expandable supporting structure design. The aspiration catheter comprises a tubular catheter body having a proximal end, a distal end, and a lumen extending therebetween. The expandable supporting structure is attached at the distal end (or distal tip) of the tubular catheter body and has a central passage contiguous with the lumen of the tubular catheter body, and the expandable supporting structure includes an expandable membrane and a supporting scaffold configured to radially expand the expandable membrane. The expandable supporting scaffold comprises a plurality of radially expandable rings arranged along a longitudinal axis, wherein at least some of the radially expandable rings comprise a serpentine or zig-zag or open pattern including struts joined by crowns forming a cell space there between. A multiplicity of supporting elements are positioned in the cell space to support the membrane in said cell space in the as delivered configuration and/or in the expanded configuration, and wherein the supporting elements resist collapse of the membrane in said space in the expanded membrane configuration when a vacuum is applied at a proximal end of the aspiration lumen and the distal tip is blocked or plugged with clot or other substances, and wherein the supporting elements allow contraction the expanded supporting structure from an expanded configuration to a smaller configuration when the aspiration catheter is withdrawn into a guiding catheter having an inner lumen configuration smaller than the expanded configuration of the supporting structure.

In a third aspect, the present invention provides a method for aspirating clot from a patient's vasculature. The method comprises positioning a distal end of the expandable supporting structure of any of the aspiration catheters, as described, in the patient's vasculature at or near a region of clot. The expandable supporting structure is expanded, typically by balloon expansion (but alternatively by self-expansion), to engage a clot or to engage a vascular wall adjacent the region of clot. A negative pressure (vacuum) is applied to a proximal end of the aspiration lumen in the catheter body to aspirate the clot into the aspiration central passage of the expanded expandable structure.

In a preferred example, the present invention provides a method for aspirating clot from a patient's vasculature. The method comprises positioning a distal tip of the expandable supporting structure of any of the aspiration catheters, as described, in the patient's vasculature at or near a clot. The expandable supporting structure is expanded to an expanded configuration, typically by balloon expansion but alternatively by self-expansion, to engage a clot or to engage a vascular wall adjacent to a clot. A vacuum is applied to a proximal end of the lumen in the catheter body to aspirate the clot into the central passage of the expanded expandable structure, at least a portion of the expandable supporting structure is optionally contracted from the expanded configuration to a smaller configuration, prior to removal from the vasculature.

In a fourth aspect, the present invention provides an aspiration catheter comprising a tubular catheter body having a proximal end, a distal end, and a lumen extending along a longitudinal axis. A distal tip has a proximal end incorporated into or is attached to the distal end of the tubular catheter body and a central passage (aspiration lumen) longitudinally contiguous with the lumen of the tubular catheter body. The distal tip is adapted to expand from an as delivered configuration to a radially expanded configuration or from a radially contracted configuration to a radially expanded configuration in response to a radially outward expansion force applied within the distal tip segment, and the distal tip comprises an expandable membrane and an expandable supporting structure such as a scaffold where the expandable scaffold or other expandable supporting structure comprises a plurality of rings spaced-apart along the longitudinal axis with gaps therebetween. At least some of the rings comprise a malleable metal or metal alloy configured to plastically deform to circumferentially expand the scaffold or other expandable supporting structure in response to the radially outward expansion force applied from within the distal tip.

In some instances, the expandable membrane is attached to an inner and/or outer surface of the expandable scaffold or other expandable supporting structure. In other instances, the expandable scaffold or other expandable supporting structure is embedded in or within the expandable membrane, wherein the expandable membrane comprises at least two membrane one is attached to an outer surface of the expandable scaffold or other expandable supporting structure while the other is attached to an inner surface of the expandable scaffold or other expandable supporting structure. In other instances, an aspiration catheter comprising an expandable tip, wherein the expandable tip comprises an expandable membrane and an expandable supporting structure such as a scaffold where the expandable scaffold or other expandable supporting structure comprises a plurality of rings spaced-apart along the longitudinal axis with gaps there between and within each of the rings, wherein the rings comprise structural elements comprising struts and crowns. The expandable scaffold or other expandable supporting structure is embedded in or within the expandable membrane, wherein the expandable membrane comprises at least one membrane wherein the at least one membrane is softened and/or melted over an outer surface of the expandable scaffold or other expandable supporting structure and/or over an inner surface of the expandable scaffold or other expandable supporting structure, allowing the expandable membrane to protrude or flow into the gaps present within the ring structural elements and gaps present between adjacent rings, adhering to said rings and rings structural elements, providing a unified (an integrally) expandable scaffold/membrane(s) system, expandable from contracted or as delivered configuration to an expanded larger configuration. The expandable membrane, in a preferred aspect, covers an outer and/or an inner surface of the expandable structure, and also covers wherein covers comprises one or more of fills, flows into, or protrude into at least some gaps present within each ring of the expandable scaffold or other expandable supporting structure and gaps present between adjacent rings of the expandable scaffold or other expandable supporting structure, wherein the flowing membrane adheres sufficiently to the scaffold or other expandable supporting structure rings structural elements to provide a unified system (integrated system) being capable to expand from an as delivered configuration to an expanded configuration as an integrated system. The expandable membrane in a preferred aspect flows into gaps present between each of the rings, within each of the rings structural elements comprising struts joined by crowns, wherein the one or more expandable membranes in a preferred aspect covers an outer surface and/or inner surface of the expandable scaffold or other expandable supporting structure, covers at least some side surfaces of the expandable scaffold structural elements, preferably covers substantially all side surfaces of the expandable scaffold structural elements, and covers substantially all gaps between adjacent rings of the expandable scaffold or other expandable supporting structure. The expandable scaffold or other expandable supporting structure in a preferred aspect comprises an outer surface, an inner surface, and two side surfaces. In other aspect, an expandable scaffold or other expandable supporting structure is formed from a bent wire comprising an outer surface and an inner surface.

In some instances, the scaffold or other expandable supporting structure has an as delivered configuration or a radially contracted (e.g. crimped) delivery configuration and an expanded deployed configuration. Typically, the radially contracted configuration has a maximum outer diameter in a range from 0.5 mm to 30 mm, usually from 1.0 mm to 5 mm, and more usually from 2 mm to 5 mm, and the radially expanded configuration has a maximum outer diameter in a range from 1 mm to 60 mm, preferably from 1.5 mm to 45 mm, more preferably from 3 mm to 45 mm.

In some instances, the distal tip may be configured to expand from an initial cylindrical shape to an enlarged cylindrical configuration in response to the radially outward expansion force applied within at least a portion of the distal tip. In other instances, the distal tip is configured to expand from an initial cylindrical shape to an enlarged conical configuration in response to the radially outward expansion force applied within at least a portion of the distal tip. In a preferred example, the enlarged conical configuration ends at the distal end of the distal tip, providing the largest area (cross sectional area) for clot extraction.

In some instances, the tubular catheter body may have a working length from the proximal end to the distal end in a range from 50 cm to 200 cm, an outer diameter in a range from 0.5 mm to 30 mm, and an inner lumen diameter from 0.25 mm to 25 mm.

In some instances, the distal tip may have a bending resistance below 1 N, preferably below 0.5 N, more preferably below 0.3 N, and most preferably below 0.2 N in its initial radially contracted configuration or in the as delivered configuration as measured by a three-point flexure test (described in more detail below). The distal tip may also have a collapse pressure (vacuum) at or above 0.5 atm, preferably at or above 0.75 atm, and more preferably at about 1 atm, in its radially expanded configuration, and most preferably above 1 atm in its radially expanded configuration when a vacuum is attached to a proximal end and a clot (or plug) is engages and blocks the open distal end of the distal tip. In other examples, the distal tip may have a bending resistance range from 0.1N to 2N, preferably range from 0.1N to 0.5N, more preferably range from 0.1N to 0.35N, and most preferably range from 0.1N to 0.2N, in its initial radially contracted configuration or in the as delivered configuration.

The bending resistance is a measure of the distal tip flexibility to navigate tortuous anatomy. A lower the bending resistance indicates a higher flexibility and a better ability of the distal tip to navigate tortuous anatomy. The bending resistance of the distal tip (or any other portion of the aspiration catheter) may be measured by a three-point flexure test, such as ASTM F2606 Standard Guide for Three-Point Bending of Balloon Expandable Vascular Stents and Stent Systems or equivalent. A section of the catheter rests perpendicularly on two lower static supports with a wedge centered between them. The spacing of the two supports is 13 mm. The middle of the supported catheter section is displaced by lowering the wedge which is held in an upper grip of an Instron Tensile Tester (Instron, Norwood, MA, USA) at a deflection rate 5.0 mm/min while measuring the resistance force. The test is ended when the displacement reaches 2 mm (approximately 15% of Span Length). The three-point bending resistance for that catheter section is equal to the maximum deflection force measure during the test.

The collapse pressure is the vacuum or negative pressure which, when applied at the proximal end of the catheter body lumen, will cause the distal tip to at least partially collapse when distal tip is fully occluded. By "at least partially collapse," it is meant that an irreversible contraction (contraction that is not resolved after applied vacuum is stopped) of more than 5%, of more than 10% or of more than 15% of the distal tip inner lumen diameter or configuration. In a preferred example, the distal tip inner lumen diameter or configuration comprising a plurality of expandable rings under applied vacuum in the expanded (deployed) configuration is configured to have the expandable rings in the expanded configuration resist collapse when a vacuum is applied at a proximal end of the aspiration catheter and the distal tip is blocked or plugged with clot or other substances; or is configured to resist collapse by contracting no more than 5%, no more than 10%, or no more than 15% of any of the distal tip rings configurations when the rings are under applied vacuum in the expanded configuration of the rings and the tip engaging a clot (or a plug), or preferably by contracting no more than 10%, of the expanded configuration under vacuum, or most preferably by contracting no more than 5% of the expanded configuration under vacuum. In another example, the distal tip inner lumen diameter or configuration comprising a plurality of expandable rings under vacuum of about 1 atm, in the expanded deployed configuration, resist collapse by radially contracting by no more than 5% of any of the expandable rings, wherein the said radial contraction of no more than 5% is substantially reversible to the expanded configuration when the vacuum or negative pressure applied at a proximal end of the catheter body lumen with the central passage of distal tip is removed or stopped (i.e., the distal tip inner lumen diameter or configuration expands to the larger expanded configuration.

In another example, the present invention provides an aspiration catheter comprising a tubular catheter body having a proximal end, a distal end, and a lumen extending along a longitudinal axis. A distal tip has a proximal end attached to the distal end of the tubular catheter body and a central passage longitudinally contiguous with the lumen of the tubular catheter body (aspiration lumen). The distal tip is adapted to expand from an as delivered configuration to a radially expanded configuration or from a radially contracted configuration to a radially expanded configuration in response to a radially outward expansion force applied within the distal tip, and the distal tip comprises an expandable membrane and an expandable supporting structure such as a scaffold where the expandable scaffold or other expandable supporting structure comprises a plurality of rings spaced-apart along the longitudinal axis with gaps therebetween. At least some of the rings comprise a malleable metal or metal alloy configured to plastically deform to circumferentially expand the scaffold or other expandable supporting structure in response to the radially outward expansion force applied from within the distal tip. In a preferred example, the expandable tip comprising an expandable membrane and expandable scaffold or other expandable supporting structure are configured to radially contract by no more than 15%, preferably by no more than 10%, and more preferably by no more than 5% of any of the expandable rings, when a vacuum is applied to a proximal end of the aspiration lumen and the distal tip is engaging a clot (or plug), and to passively expand (without outward expansion force applied within the distal tip by an expandable member), wherein said expanded configuration is larger than the contracted configuration when the applied vacuum is stopped (or removed), preferable wherein the expanded configuration is larger than the contracted configuration and is substantially the same as the expanded configuration prior to applying any vacuum. In another example, the distal tip inner lumen diameter or configuration under vacuum of about 1 atm, in the expanded deployed configuration, radially contracts by no more than 15%, preferably by no more than 10%, and more preferably by no more than 5% resisting collapse, wherein the said radial contraction is substantially reversible when the vacuum or negative pressure applied at a proximal end of the catheter body lumen with the central passage of distal tip is removed or stopped (i.e., the distal tip inner lumen diameter or configuration expands to a larger configuration, larger than the contracted configuration under vacuum).

In another example, the present invention provides an aspiration catheter comprising a tubular catheter body having a proximal end, a distal end, and an aspiration lumen extending along a longitudinal axis. A distal tip has a proximal end attached to the distal end of the tubular catheter body and a central passage longitudinally contiguous with the aspiration lumen of the tubular catheter body. The distal tip is adapted to expand from an as delivered configuration (or from a first extraction configuration) to a first radially expanded configuration in response to a radially outward expansion force applied within the distal tip, wherein the first radially expanded configuration (second extraction configuration or extraction configuration) ranges from 1.1 to 2 times the as delivered configuration, and wherein the distal tip comprises one or more expandable membranes and an expandable scaffold where the expandable scaffold comprises a plurality of expandable rings spaced-apart along the longitudinal axis with gaps therebetween, and wherein the expandable rings comprise structural elements including struts joined by crowns. At least some of the rings comprise a malleable metal or metal alloy configured to plastically deform to circumferentially expand the scaffold or other expandable supporting structure in response to the radially outward expansion force applied from within the distal tip. The expandable tip comprising the one or more expandable membranes and expandable scaffold comprising a plurality of expandable rings are configured to radially contract to a first contracted configuration wherein the first contracted configuration is smaller than the first expanded configuration but larger than the as delivered configuration, preferably wherein the first contracted configuration is smaller than the first expanded configuration by no more than 15%, preferably by no more than 10%, and more preferably by no more than 5% smaller than the first expanded configuration when a vacuum is applied to a proximal end of the aspiration lumen wherein the applied vacuum, or when the applied vacuum ranges from 0.75 atm to 1 about atm, and wherein the expandable tip is configured to passively expand, to a second expanded configuration wherein the second expanded configuration is larger than the first contracted configuration and equal to or smaller than the first expanded configuration, when the applied vacuum is removed or stopped, wherein the expandable tip passively expand without outward expansion force applied within the distal tip by the one or more expandable membranes, and wherein the expandable tip is configured to contract to a second contracted configuration, wherein the second contracted configuration is smaller than the first contracted configuration and equal to or larger than the as delivered configuration, when the distal tip is withdrawn into a guiding catheter positioned proximally to the distal tip in the patient anatomy. In one example, the expandable distal tip has a length ranging from 0.5 mm to 500 mm, preferably having a length ranging from 1 cm to 50 cm, and more preferably ranging from 1 cm to 25 cm. The one or more expandable membranes of the expandable distal tip in one example extends proximally beyond the proximal end of the distal tip of the aspiration catheter. In another example, the one or more expandable membranes of the expandable distal tip has about the same length as the expandable scaffold and are both incorporated within or attached at their proximal end to the distal end of the aspiration catheter. In yet another example, the one or more expandable membranes extend from the distal end of the distal tip to a proximal end of the aspiration catheter.

In some instances, the distal tip comprising an expandable scaffold or other expandable supporting structure has a minimum bending radius without deformation and/or kinking of 5 mm, preferably 3 mm, and more preferably 2 mm in its as delivered configuration or the radially contracted configuration, and preferably, a minimum bending radius without deformation and/or kinking of 10 mm, preferably 6 mm, and more preferably 2 mm in its radially expanded configuration. Minimum bending radius may be determined by bending the distal tip about a cylinder of a known radius and observing if the distal tip deforms and/or kinks.

In some instances, the rings of the expandable scaffold or other expandable supporting structure span a length in a range from 0.25 mm to 500 mm or more measured in a longitudinal direction, preferably a range from 1 mm to 100 mm, more preferably a range from 10 mm to 70 mm, and most preferably range from 20 mm to 50 mm.

In another example, the present invention provides an aspiration catheter comprising a tubular catheter body having a proximal end, a distal end, and an aspiration lumen extending along a longitudinal axis. A distal tip has a proximal end incorporated into the distal end of the tubular catheter body and a central passage longitudinally contiguous with the aspiration lumen of the tubular catheter body. The distal tip is adapted to expand from an as delivered configuration to a first radially expanded configuration in response to a radially outward expansion force applied to the distal tip, wherein the first radially expanded configuration ranges from 1.1 to 2 times the as delivered configuration, and wherein the distal tip comprises one or more expandable membranes and an expandable scaffold where the expandable scaffold comprises one or more expandable rings spaced-apart along the longitudinal axis with gaps therebetween, and wherein the expandable rings comprise structural elements including struts joined by crowns. The one or more rings are composed of a malleable metal or metal alloy (or alternatively are formed from shape memory metallic alloy) configured to plastically deform to circumferentially expand the scaffold or other expandable supporting structure in response to the radially outward expansion force applied from inside the distal end or distal tip. In a specific example, the expandable scaffold consists of one, two, or three expandable rings. In another specific example, the expandable scaffold consists of one expandable ring.

In some instances, the distal tip comprising an expandable scaffold or other expandable supporting structure has a minimum bending radius without deformation and/or kinking of 5 mm, preferably 3 mm, and more preferably 2 mm in its as delivered configuration or the radially contracted configuration, and preferably, a minimum bending radius without deformation and/or kinking of 10 mm, preferably 6 mm, and more preferably 2 mm in its radially expanded configuration. Minimum bending radius may be determined by bending the distal tip about a cylinder of a known radius and observing if the distal tip deforms and/or kinks.

In some instances, the rings of the expandable scaffold or other expandable supporting structure span a length in a range from 0.25 mm to 500 mm or more measured in a longitudinal direction, preferably a range from 1 mm to 100 mm, more preferably a range from 10 mm to 70 mm, and most preferably a range from 10 mm to 40 mm.

In some instances, the expandable scaffold or other expandable supporting structure consists of from 1 ring to 800 rings or more, preferably consist of 25 rings to 650 rings or more, more preferably consist of 50 rings to 500 rings or more, spanning one or more expandable axial segments lengths ranging from 0.2 mm to 50 cm, preferably ranging from mm to 40 cm, more preferably ranging from 15 mm to 25 cm said rings arranged in a longitudinal direction from the distal end of the distal tip to a distal end or to a proximal end, of the aspiration catheter. In a preferred example, the expandable scaffold or other expandable supporting structure comprises or consists of a plurality of rings per mm of axial (longitudinal) scaffold or other expandable supporting structure length, ranging from 2 rings/mm to 5 rings/mm of length, preferably consists of from 2.5 rings/mm to 4 rings/mm of length, and more preferably consists of from 3 rings/mm to 4 rings/mm of length, of axial (longitudinal) scaffold length.

In some instances or examples, the expandable supporting structure comprises a plurality of adjacent rings having a gap between the adjacent rings. In some examples, the gap between adjacent rings has length in a range from 0.0125 mm to 0.25 mm measured in a longitudinal/axial direction, preferably from 0.025 mm to 0.2 mm, and more preferably range from 0.05 mm to 0.17 mm.

In some instances, the axial length of gap (i.e., gap length measured is an axial direction) between adjacent rings may be constant. In other instances, the axial length of gap between adjacent rings may be variable. For example, the length (or axial length) of gaps between at least some adjacent rings range from 0.05 mm to 0.2 mm. In another preferred example, a plurality of adjacent rings spanning at least 3 mm segment along a length of the expandable structure, more preferably spanning at least 7 mm segment along a length of the expandable scaffold, more preferably spanning at least 20 mm segment along a length of the expandable scaffold wherein the adjacent rings having gap lengths adjacent the adjacent rings ranging from 0.05 mm to 0.2 mm.

In some instances, the distal tip has at least 2 ring per mm of axial length, preferably at least 3 rings per mm of length, typically from 1.5 to 5 rings per mm of length, and more typically from 2 to 5 rings per mm of length, or more typically from 3 to 4 rings per mm of length.

In some preferred instances, at least some of the adjacent rings are joined continuously, end-to-end in a helical arrangement. In other instances, at least some of the adjacent rings are planar, arranged in parallel, and joined by axial links or other means such as attachment points and are not joined end-to-end. The parallel planes may be normal or inclined relative to a longitudinal axis of the distal tip in its as delivered configuration. The adjacent rings may be joined preferably by a single axial link or attachment point, or by no more than two axial links or two attachment points. In some preferred instances, at least some adjacent rings of the expandable scaffold are joined continuously, end-to-end in a helical pattern or arrangement. In other instances, at least some adjacent rings of the expandable scaffold are planar, arranged in parallel, and joined by axial links or attachment points joining or connecting structural elements on adjacent rings. In this other instance, the scaffold adjacent rings are not joined continuously end-to-end in a helical arrangement. The parallel planes may be normal or inclined relative to a longitudinal axis of the distal tip in its as delivered configuration. The adjacent rings may be joined preferably by a single axial link or attachment point, or by no more than two axial links or attachment points.

In other instances, at least some adjacent rings of the expandable scaffold are planar, arranged in parallel, and are unconnected to each other. (Unconnected by links, attachment points, or joined end to end in a helical arrangement). The parallel planes may be normal or inclined relative to a longitudinal axis of the distal tip in its as delivered configuration The at least some adjacent rings in this instance are covered by one or more membrane adhering to the unconnected adjacent rings, holding them together, and allowing the at least some adjacent ring to expand from an as delivered configuration to an expanded configuration. This allows for enhanced deliverability of the distal tip to navigate vascular anatomy in the as delivered configuration and allows the at least some rings to expand from an as delivered configuration to an expanded configuration and resist collapse of the distal tip from the expanded configuration when a vacuum is applied at a proximal end of the aspiration lumen and a clot is engaging (or a plug is blocking) the distal end of the distal tip.

In some instances, at least some of the adjacent rings in the helical and/or planar arrangement may comprise non-linearities.

In some instances, all the adjacent rings in the helical and/or planar arrangement are free from non-linearities.

In some instances, at least some of the adjacent rings have thickness ranging from 0.03 mm to 0.3 mm, preferably ranging from 0.05 mm to 0.25 mm, more preferably ranging from 0.05 mm to 0.2 mm.

In some instances, the malleable metal comprises a metal or metal alloy selected from the group consisting of Cobalt Chrome such as L-605, MP35N, Stellite 6B, ASTM F1537/F799 Alloy 1, ASTM F1537/F799 Alloy 2, Stainless Steel such as 316, 316L, 316LS, 316LVM, 304, 304V, 304L, 304LV, 304LVM, 410, 410L, 410S, 420, 420L, and 420S, Tantalum, Niobium, Tungsten, Molybdenum, Molybdenum, Molybdenum alloys such as Molybdenum-Rhenium where total of the two adds up to 90% to 100% and may include one or more metals such as Boron, Calcium, Chromium, Cobalt, Copper, Gold, Iron, Lead, Magnesium, Manganese, Mercury, Nickel, Niobium, Platinum, Rare Earth metals, Silicon, Silver, Sulfur, Tantalum, Tin, Titanium, Tungsten, Yttrium, Zinc, and Zirconium, Platinum, Platinum alloys such as Platinum-Iridium, Platinum-Chromium, Platinum-Cobalt-Chromium, Magnesium, Magnesium alloy such as Mg-3Al-1Z, Mg—Zn—Se and Mg—Zn—Cu, Zinc, or the like, or other.

In some instances, the scaffold or other expandable supporting structure comprises metal or metal alloy selected from the group consisting of Nitinol, Superelastic Nitinol, or the like, or other. In such instances, the expandable supporting structure is constrained in the as delivered configuration and is released from the constraint to expand the scaffold to the expanded configuration.

In some instances, the expandable membrane comprises one or more of an elastic membrane, and/or inelastic but stretchable membrane, and/or one or more plastically deformable membrane where the membrane may comprise one or more membranes comprising polymers, elastomers, or other as listed previously.

In some instances, the elastic membrane may have isotropic properties. In other instances, the elastic membrane may have anisotropic properties. For example, the membrane may have a higher elasticity in a circumferential direction than in an axial direction.

In some instances, the expandable membrane may comprise an elastic membrane, an inelastic but stretchable membrane, or other type expandable material. Suitable material examples as listed previously.

In some instances, the inelastic membrane may be configured to stretch, or plastically deform as the scaffold or other expandable supporting structure expands. In other instances, an inelastic membrane may be configured to unfold as the as the scaffold or other expandable supporting structure expands.

In some instances, the distal tip may be formed by heat shrinking the tubular membrane on the expandable scaffold or other expandable supporting structure. In other instances, distal tip may be formed by laminating the expandable scaffold or other expandable supporting structure between layers of the tubular membrane. For example, the layers may be bonded to each other so that there is a seal between the layers. In a preferred example, the one or more expandable membranes flow and cover at least some side surfaces of the expandable supporting structure structural elements, adhere to said structural elements sufficiently to provide a unified system (an integrated system) in the as delivered configuration and when expanded to an expanded configuration. In yet another example, the polymeric layers on an outer surface of the scaffold and on the inner surface of the scaffold may be bonded to each other and/or adhere to the scaffold structural elements so that there is a seal between the layers and/or adherence to the structural elements providing a unified integrated system expandable from an as delivered configuration to an expanded configuration. In a preferred example, the structural elements of the scaffold are not free to move or expand without moving or expanding the expandable membrane adjacent to said structural elements. In yet another example, the layers on an outer scaffold surface and inner scaffold surface may be bonded to each other so that there is a seal between the layers. In yet another example, the layers on an outer scaffold surface and on an inner scaffold surface maybe coupled, attached, and/or adhered to each other substantially eliminating the gaps between the structural elements (or filling the gaps) of the scaffold, and providing a unified expandable scaffold being expandable from an as delivered configuration to an expanded configuration. In yet another example, the one or more layers on an outer surface of the scaffold or the one or more layers on an inner surface of the scaffold are melted or laminated onto the structural elements of the scaffold, eliminating at least in part the gaps between said structural elements and adhering to said structural elements providing the scaffold the ability to expand from an as delivered configuration to an expanded configuration as a unified system.

In some instances, the tubular membrane may consist of at least two membrane segments, where the at least two membrane segments may comprise a single type of material, at least two types of material, or three or more different material types.

In some instances, the at least two membrane segments may cover at least an outer surface of the expandable scaffold or other expandable supporting structure. In some instances, the at least two membrane segments may cover at least an inner surface of the expandable scaffold or other expandable supporting structure. In some instances, the at least two membrane segments cover both an inner surface and an outer surface of the expandable scaffold or other expandable supporting structure, wherein at least one membrane segment of said at least two membrane segments covers an outer surface of the scaffold while at the least the second membrane segment covers an inner surface of the expandable scaffold.

In some instances, the tubular catheter body may be reinforced over at least a portion of its length by a catheter scaffold or other supporting structure, typically a flexible but non-expandable supporting structure. In specific examples, the catheter scaffold or other supporting structure may be formed continuously with the expandable scaffold or other expandable supporting structure. For example, the catheter and supporting scaffold may be patterned from the same tube or bent wire. In other instances, the catheter scaffold and the expandable scaffold may be formed from one or more bent wires which each span at least portions of the typically non-expandable catheter scaffold and the expandable distal tip scaffold.

In some instances, the expandable scaffolds may further comprise a multiplicity of cantilevered or other supporting elements, each supporting element having a base end and a free end, wherein the base end is attached to one of the radially expandable rings and the free end extends toward or into an adjacent axial and/or circumferential gap.

In some instances, at least some of the plurality of rings may comprise struts joined by bends (crowns) and at least some of the multiplicity of supporting elements have their base ends attached to a strut and at least some of the multiplicity of supporting elements have their base ends attached to a bend (crowns).

In some instances, at least some of the multiplicity of supporting elements may have their base ends attached to an inside surface of the ring, i.e., the inside bend of a crown.

In some instances, at least some of the multiplicity of supporting elements may have their base ends attached to an outside surface of the ring, i.e., an outside surface of a crown, or to the apex of the outside surface of a crown.

In some instances, at least some of the multiplicity of supporting element have a constant width over their distal portions. In some instances, at least some of the multiplicity of supporting element have a constant width over their entire length.

In some instances, at least some of the multiplicity of supporting element have a variable width over their distal portions.

In some instances, at least some of the multiplicity of supporting element have distal tips which extend into an adjacent circumferential, axial or other gap.

In some instances, at least some of the multiplicity of supporting element have distal tips which terminate flush with the bends that struts join the struts.

In some instances, at least some of the multiplicity of supporting element have distal tips which are recessed between adjacent bends that join the struts.

In a fifth aspect, the present invention provides an aspiration catheter comprising a tubular catheter body having a proximal end, a distal end, and a lumen extending along a longitudinal axis. The distal end comprises an expandable distal tip and a central passage where the central passage is typically longitudinally contiguous with the lumen of the tubular catheter body. The distal tip is adapted to expand from a radially contracted or as delivered configuration to a radially expanded configuration in response to a radially outward expansion force applied inside the distal tip, and the distal tip includes a tubular membrane covering (e.g., adhered to, attached to, bonded to, or laminated with) an expandable scaffold or an expandable supporting scaffold. The expandable scaffold or the expandable supporting scaffold comprises a plurality of rings spaced-apart along the longitudinal axis with gaps therebetween (extending between rings) and at least some of the rings comprise circumferentially adjacent cells having bends (such as crowns) configured to unbend (such as to expand) in response to a radially outward expansion force applied inside the distal tip to allow the ring to expand from the radially contracted or as delivered configuration to the radially expanded configuration, wherein the radially expanded configuration is larger than the contracted configuration. In some preferred instances, at least some adjacent rings of the expandable scaffold or expandable supporting scaffold are joined continuously, end-to-end in a helical arrangement, typically free from axial links or attachments points. In a preferred instance, the at least some adjacent rings of the expandable scaffold or expandable supporting scaffold have a fixed cell amplitude within each ring. In other instances, the at least some adjacent rings of the expandable scaffold or expandable supporting scaffold have a fixed cell amplitude within the at least some rings. In rare instances, the at least some adjacent rings of the expandable scaffold or expandable supporting scaffold may have a variable cell amplitude within each ring or within the at least some rings. The at least some adjacent rings in this instance have a pitch angle in a range from 70° to 89.9°, or from 75° to 89.9°, usually from 80° to 89.9°, more usually from 84° to 89.75°, and frequently from 85° to 88.5° degrees as patterned, or as delivered, relative to the longitudinal axis of the scaffold or distal tip. As used herein and as illustrated in the drawings, the "pitch angle" will be the acute angle (between 0° and 90°) not the obtuse angel (between 90° and 180°) formed by the ring relative to the longitudinal axis of the distal tip of the aspiration catheter. In some other instances, at least some adjacent rings of the expandable scaffold or the expandable supporting scaffold are planar, arranged in parallel, and are joined by one axial link or attachment point joining structural elements on adjacent rings. In rare cases, the at least some adjacent rings are joined by no more than two axial links, by no more than two attachment points joining structural elements on adjacent rings, or by no more than one link and no more than one attachment point. The parallel planes may be normal or inclined relative to a longitudinal axis of the distal tip in its as delivered configuration.

In some instances, the cells may be arranged in any one or more of a box pattern, diamond pattern, a sinusoidal pattern, serpentine pattern, an omega-wave pattern, a zig-zag pattern, a square wave pattern, a rectangular wave pattern, an undulating pattern, a slotted pattern, open cell pattern, closed cell pattern, a combination of open and closed cell patterns, a combination of patterns, or other, and the like.

In some instances, adjacent and/or non-adjacent rings have crowns that are in-phase or out-of-phase.

In some instances, the cells may comprise struts joined by bends.

In some instances, at least some expandable cells on one or more rings of the expandable scaffold, or at least some expandable cells on at least some rings of the expandable scaffold, or at least some expandable cells on each ring of the expandable scaffold, or the at least some circumferentially adjacent cells of at least some rings of the expandable scaffold, or at least some circumferentially adjacent cells on at least some adjacent rings of the expandable scaffold may, or substantially all cells on the expandable scaffold, or all cells along a length of a scaffold wherein the length is less than the length of the scaffold, or all cells along the length of a scaffold, have a cell period (distance between like points on circumferentially adjacent cells measured in the contracted configuration) in a range from 0.03 mm to 1.3 mm, preferably from 0.04 mm to 0.8 mm, more preferably from 0.05 mm to 0.5 mm, and most preferably from 0.05 mm to 0.15 mm, in the as delivered configuration, or in the as patterned configuration. Having a small cell period enhances circularity of a ring, or circularity of the plurality of rings, or circularity of the expandable scaffold, thereby enhances navigation of the expandable scaffold into the vasculature without deformation or kinking in the as delivered configuration, and said enhanced circularity resist collapse of the expandable distal tip when expanded to the expanded configuration and a vacuum is applied at a proximal end of the aspiration catheter while the distal tip is engaging a clot (or is plugged). Furthermore, having small cell period increases (or enhances) the aspiration area within the ring, within the plurality of rings, or within the expandable scaffold or expandable distal tip.

In some instances, the circumferentially adjacent cells on at least one ring or on at least some rings (or at least some circumferentially adjacent cells on the same ring, or at least some circumferentially adjacent cells on at least some adjacent rings) of the expandable scaffold, or at least one ring, or at least some rings, or all the rings of the expandable scaffold, may have a peak-to-peak amplitude (ring width in the longitudinal/axial direction (the axial width of a ring)) in a range from 0.05 mm to 1.2 mm, preferably from 0.05 mm to 0.8 mm, more preferably from 0.15 mm to 0.5 mm, and most preferably from 0.15 mm to 0.35 mm, in the as delivered configuration or in the as patterned configuration. In a preferred example, the cell amplitudes of each cell on the same ring have the same length (is fixed or is constant) in the as delivered configuration or as patterned configuration. In another preferred example, at least some adjacent rings have cell or ring amplitude being the same length on said at least some rings. Having small amplitude enhances flexibility of the expandable scaffold thereby enhances the navigation of the expandable scaffold (or expandable distal tip) when the aspiration catheter is advanced into the vasculature. Furthermore, having small amplitude further strengthen the expandable scaffold in the expanded configuration and resist collapse of the scaffold or the expandable membrane coupled to the scaffold when a vacuum is applied at a proximal end of the aspiration catheter and the distal tip is engaging a clot.

In some instances, the circumferentially adjacent cells (or at least some circumferentially adjacent cells, or at least some circumferentially adjacent cells on at least some adjacent rings, or all cells on the expandable scaffold, or at least some cells within a ring, or all cells within at least some rings, or all cells within rings of the expandable scaffold) may have a cell period to a (peak to peak axial width of a ring) amplitude range as follows: In one example, a cell period to a (peak to peak axial width of a ring) amplitude range from 0.3:1 to 1.6:1. In other example, a cell period to a (peak to peak axial width of a ring) amplitude range from 0.4:1 to 1.5:1. In yet other example, a cell period to a (peak to peak axial width of a ring) amplitude range from 0.5:1 to 1.3:1. In yet other example, a cell period to a (peak to peak axial width of a ring) amplitude range from 0.6:1 to 1.2:1. In yet other instances, a cell period to a (peak to peak axial width of a ring) amplitude range from 1:1 to 1.6:1. In yet other instances, a cell period to a (peak to peak axial width of a ring) amplitude range from 0.3:1 to 1.2:1, measured in the as delivered configuration or in the as patterned configuration for all the examples. In some other examples, the circumferentially adjacent cells (or at least some cells on a ring or on a plurality of rings or on at least some rings, or all cells on at least one ring or on at least some rings, or at least some rings of the expandable scaffold) may have a cell period and a (peak to peak axial width of a ring) amplitude each having a length of 0.25 mm±0.2 mm, preferably each having a length of 0.25 mm±0.15 mm, and more preferably each having a length of 0.25 mm±0.1 mm, measured in the as delivered configuration (or measured in the as patterned configuration). Having the length of at least some cell periods and amplitudes within a ring or within a plurality of rings or within at least some rings being within ±0.2 mm of each other enhances symmetry and/or compactness of the rings of the expandable scaffold resisting deformation and/or kinking when the expandable scaffold navigates into the vasculature in the as delivered configuration.

In some instances, each ring (or at least some rings) may include from 2 cells to 15 cells per mm of circumference, preferably each ring (or at least some rings) may include from 3 cells to 10 cells per mm of circumference, and most preferably each ring (or at least some rings) may include from 4 cells to 9 cells per mm of circumference.

In some instances, at least some rings in the scaffold or other expandable supporting structure may have a ratio of (1) number of bends to (2) circumference, where the ratio is typically in a range from 0.8 per mm to 15 per mm, preferably from 1 per mm to 15 per mm, more preferably from 2 per mm to 15 per mm, more preferably from 3 per mm to 15 per mm and most preferably from 4 per mm to 12 per mm. Supporting structures having cantilevered or other supporting elements will typically have fewer bends per unit length of the ring circumference.

The ratio of (1) number of bends to (2) circumference may be constant or variable over at least some rings, over all or a portion of the scaffold or other expandable supporting structure.

In some instances, the rings may span a segment of the distal tip having a length in the distal tip in a range from 0.5 mm to 500 mm or more, usually from 10 mm to 100 mm, and more usually from 10 mm to 40 mm, measured in a longitudinal direction.

In some instances, the rings may span a segment of the distal tip having a length in the distal tip in a range from 0.5 mm to 500 mm or more, usually from 10 mm to 100 mm, and more usually from 10 mm to 40 mm, measured in a longitudinal direction. In some instances, the scaffold is composed of one expandable ring spanning a length in the distal tip in a range from 0.1 mm to 0.5 mm, usually from 0.15 mm to 0.35 mm, and more usually from mm to 0.3 mm, measured in a longitudinal direction.

In some instances, the distal tip may have from 1 to 10 rings per mm of length of the distal tip, usually from 2 to 8 rings per mm of length of the distal tip, more usually from 3 to 5 rings per mm of length of the distal tip.

In a preferred example, the rings of the expandable supporting structure comprise bends, e.g., crowns, and struts, where the bends have a length measure along their arc and the struts have an axial length, wherein a ratio of the arc length of the bend or crown to the axial length of the strut ranges from 0.2:1 to 2:1, preferably from 0.5:1 to 1.5:1, and more preferably from 0.75:1 to 1.25:1. In specific preferred examples, the arc lengths of crowns and axial lengths of the struts connected to the crowns are each in a range from 0.05 mm to 0.25 mm, preferably from 0.075 mm to 0.225 mm, and more preferably from 0.1 mm to 0.2 mm, preferably being about 0.15 mm, or preferably being 0.15±0.05 mm, for example being 0.15±0.05 mm.

In some instances, at least some of the adjacent rings in the expandable distal tip may be formed from a tube or a bent wire and joined continuously in an end-to-end in a helical arrangement. For example, the at least some adjacent rings may be joined at an absolute pitch angle in a range from 70° to 89.9°, or from 75° to 89.9°, usually from 80° to 89.9°, more usually from 84° to 89.75°, and frequently from 85° to 88.5° as patterned or as delivered, relative to the longitudinal axis. The absolute pitch angle may be constant or variable along at least some rings, or along the length of the expandable scaffold (or a long a length of the expandable scaffold wherein the length is shorter than the length of the scaffold or along other expandable supporting structure) or other expandable supporting structure. The absolute pitch angle of at least some adjacent rings maybe constant or variable along the length of the expandable scaffold or other expandable supporting structure. The pitch angles are typically measured in the as patterned configuration. Alternatively, the pitch angles above maybe measured in the as delivered configuration. In a preferred instance, the at least some adjacent rings are free from links or attachments points between the adjacent rings. In other preferred instances, the at least some adjacent rings have fixed cell amplitude within each ring or within the at least adjacent rings. In rare instances, at least some adjacent rings may have attachment point or links connecting adjacent rings. In other rare instances, at least some adjacent rings may have a variable cell amplitude or a variable ring amplitude within each ring or within the adjacent rings.

In other instances, at least some of the adjacent rings may be arranged as separate parallel planes and joined by axial links or joined by other means such as crowns on adjacent rings which are fused/soldered or otherwise joined together (attachment points). The separate parallel planes may be oriented perpendicularly or at an angle relative to a longitudinal axis of the scaffold or other expandable supporting structure when straightened. In some instances, the separate adjacent rings are not joined together by links or by other means but are held together by one or more expandable membrane containing, covering, and/or embedding the separate rings.

In some instances, at least some of the cells may comprise a malleable metal or metal alloy configured to plastically deform. The malleable metal may comprise a metal or metal alloy as identified previously in this application.

In some instances, the radially contracted configuration of the scaffold or other expandable supporting structure and/or the distal tip may have a maximum diameter in a range from 0.5 mm to 30 mm, usually from 1.3 mm to 5.5 mm, and the radially expanded configuration may have a minimum diameter in a range from 1 mm to 40 mm, usually from 2 mm to 5.5 mm.

In some instances, the distal tip may be configured to expand from an initial cylindrical shape to an enlarged cylindrical configuration in response to the radially outward expansion force applied within the distal tip.

In some instances, distal tip may be configured to expand from an initial cylindrical shape to an enlarged conical configuration in response to the radially outward expansion force applied within (or applied from inside) the distal tip.

In some instances, circumferentially adjacent cells in at least some of rings in the distal tip may have round, oval, oblong, flat or substantially flat outer and/or inner surfaces which define "facets" in a polygonal structure. In those instances, the ring may have a first radius from an axial center line of the ring to the circumferential center of each facet and a second radius from an axial center line of the ring to the a circumferential edge of each facet where the length of the first radius is from 97% to 99.9% of the length of the second radius, preferably being from 98% to 99.7%, more preferably being from 98.5% to 99.5%, and most preferably being from 99% to 99.5%, in the expanded configuration. This provides the expandable distal tip with one or more of the following: enlarged inner lumen configuration (or maximum inner lumen configuration), enhanced aspiration lumen area, maximize the aspiration lumen area in the expanded configuration, resist collapse in the expanded configuration under vacuum when the distal tip is engaging a clot (or blocked or plugged with clot or other substances, enhance deliverability of the aspiration catheter distal tip, and enhance deformation resistance or kink resistance of the expandable distal tip in the as delivered configuration when navigating the vasculature. In a preferred instance, the expandable tip in the expanded configuration has a "circularity" (as defined below with respect to FIG. 16) ranging from 97% to 99.9%, preferably ranging from 98% to 99.5%, and more preferably ranging from 98.5% to 99.5%. In another preferred instance, the circularity of the expandable tip in the expanded configuration is greater than 97%, preferably greater than 98%, more preferably greater than 98.5%, and most preferably greater than 90%. The circularity of the expandable distal tip refers to the inner lumen configuration. Alternatively, the circularity of the expandable distal tip measuring the outer circumference of the distal tip.

In some instances, the tubular catheter body may have a length from the proximal end to the distal end in a range from 50 cm to 200 cm, an outer diameter in a range from 0.5 mm to 30 mm, and an inner lumen diameter from 0.25 mm to 25 mm. In one example, the expandable distal tip length ranges from 0.5 mm to 50 cm. In another example, the expandable distal tip length is the same as the distal end length. In other examples, the expandable distal tip comprises substantially the entire length of the catheter tubular body. In yet another example, the expandable distal tip is composed of an expandable scaffold (or expandable supporting scaffold) covered with or embedded within one or more polymeric material, wherein the expandable scaffold comprises one circumferential ring, said one ring comprises a plurality of struts joined by crowns, and wherein the ring is expandable from an as delivered configuration to an expanded configuration, said ring resist collapse when a vacuum is applied at a proximal end of the aspiration lumen and the distal end of the distal tip is opposed to a clot or plugged. In some other instances, the expandable scaffold comprises 2, 3, 4, or 5 circumferential rings.

In some instances, the expandable distal tips may further comprise a multiplicity of supporting elements, where each supporting element may have a base end and a free end and where the base end is attached to one of the radially expandable rings and the free end extends towards or extends into an adjacent gap in an axial and/or circumferential direction to the distal tip. For example, at least some of the plurality of rings may comprise struts joined by bends and at least some of the multiplicity of supporting elements may have their base ends attached to a strut and/or at least some of the multiplicity of supporting elements may have their base ends attached to a bend.

In other instances, at least some of the multiplicity of supporting elements may have their base ends attached to an inside surface of the ring (or the rings ring's structural elements) and/or attached to an outside surface of the ring (or the ring's structural elements).

In some instances, at least some of the multiplicity of supporting elements may have a constant width over their distal portions or along their entire length. In other instances, at least some of the multiplicity of supporting element may have a variable width over their distal portions or along their length. In other instances, at least some of the multiplicity of supporting elements may have a larger width at their base and a constant width along the remaining length of the supporting elements. In a preferred example, the width of the supporting elements is larger than the width of an adjacent struts, crown, or ring segment. Having larger supporting elements width that adjacent structural elements allow contraction of the expandable scaffold or other expandable supporting structure after expansion of the scaffold to an expanded configuration when the scaffold is withdrawn into a guiding catheter having an inner lumen smaller than the expanded configuration of the expandable scaffold.

In some instances, at least some of the multiplicity of supporting elements may have distal tips which extend toward and/or into the adjacent circumferential and/or axial gap.

In some instances, at least some of the multiplicity of supporting elements may have distal tips which terminate flush with adjacent bend or crowns that join the struts.

In some instances, at least some of the multiplicity of supporting elements have distal tips which are recessed between adjacent bends that join the struts in the as delivered configuration and wherein the supporting elements project further towards or further into an adjacent gap.

In still other aspects, the present invention provides methods for aspirating clot from a patient's vasculature comprising positioning a distal tip of any one of the aspiration catheters described herein in the patient's vasculature at a region of clot. The distal tip is expanded to its radially expanded configuration, or to a radially expanded configuration from an as delivered configuration, to engage a vascular wall adjacent the region of clot, or to engage a clot, and a negative pressure is applied to a proximal end of the lumen in the catheter body to aspirate the clot into the central passage of the expanded expandable supporting structure (the aspiration lumen). The expanded configuration has a suction force larger than the as delivered configuration under the same applied vacuum. The suction force in the expanded configuration is larger by a range from 1.1 to 10 times, preferably larger by a range from 1.5 to 6 times, more preferably larger by a range from 1.8 to 6 times the suction force of the as delivered configuration.

In some instances, at least a portion of the expandable scaffold or other expandable supporting structure remains at least partially unexpanded after expansion of another portion of the expandable scaffold. The at least partially unexpanded portion may have a variety of shapes such as cone shape, oval shape, oblong shape, flat shape, or other shapes. In some other instances, at least one segment of the expandable scaffold or other expandable supporting structure comprises remains unexpanded after expansion of another adjacent segment of the expandable scaffold or other expandable supporting structure to the expanded configuration.

In still other aspects, the present invention provides a method for aspirating clot from a patient's vasculature comprising positioning a distal tip of any one of the aspiration catheters described herein in the patient's vasculature at a region of clot. At least a segment of the distal tip is expanded to its radially expanded configuration from an as delivered configuration (contracted configuration) to engage a vascular wall adjacent to the region of clot, or to engage a clot, and a negative pressure is applied to a proximal end of the lumen in the catheter body to aspirate the clot into the central passage of the expanded expandable structure. In other examples, the clot is aspirated in the contracted (as delivered) configuration without expanding the distal tip to the expanded configuration.

In some instances, a segment or other portion of the expandable scaffold or other expandable supporting structure remains at least partially unexpanded after expansion of another portion of the expandable scaffold.

In still other aspects, the present invention provides an aspiration catheter comprising a tubular catheter body having a proximal end, a distal end, and a lumen extending along a longitudinal axis. An expandable coil comprising successive helical turns is disposed along a longitudinal axis, where the expandable coil comprises undulating bends and struts and said successive turns having a gap therebetween, wherein the successive turns are inclined at an acute pitch angle relative to the longitudinal axis. A jacket is disposed about the expandable coil. In a preferred example, the acute pitch angle ranges from 70° to 89.9°, usually from 80° to 89.75°, and more usually from 82° to 89.75° degrees, relative to the longitudinal axis, in the as patterned or as delivered configurations. In a preferred instance, at least some successive turns are free from links or attachment points joining said adjacent turns. In yet another preferred instances, at least some adjacent turns have fixed cell amplitudes within each turn or within the at least some adjacent turns.

In some instances, the expandable scaffold or other expandable supporting structure is composed of an expandable coil wherein the expandable coil comprises a plurality of adjacent expandable rings joined continuously, end-to-end in a helical arrangement, wherein each ring comprises structural elements comprising struts joined by crowns, and wherein the expandable coils have an acute pitch angle ranging from 70° to 89.9°, preferably ranging from 80° to 89° degrees, relative to the longitudinal axis as patterned or as delivered. The expandable coil is expanded from an as delivered configuration or a contracted configuration to an expanded configuration by an expandable supporting structure radially expanded in an interior of the expandable coil such as a balloon catheter, wherein said expandable coil is said to be balloon expandable.

In some instances, the expandable coil may be configured to be expanded by an expandable supporting structure radially expanded in an interior of the expandable coil. For example, the expandable coil may be balloon expandable.

In some instances, the coil may be formed at least in part from a malleable metal or metal alloy. In some other examples, the coil may be formed from a malleable metal or metal alloy.

In some other instances, the coil maybe formed from a shape memory metal or shape memory alloy, wherein the expandable distal tip is constraint in the as delivered configuration and is released to expand to the larger expanded configuration. Examples of shape memory alloys include nickel titanium alloy, or other.

In some instances, at least a proximal portion of the tubular catheter body may be non-expandable.

In some instances, at least a proximal portion of the tubular catheter body may be radially expandable.

In some instances, the expandable coil may be attached to a reinforcement member in a proximal segment of the catheter body.

In some instances, the expandable coil and the reinforcement member may be formed from a continuous wire or tube.

In some instances, the adjacent rings may be joined at an acute pitch angle in a range from 70° to 89.9°, preferably range from 80° to 89.9°, more preferably range from 85° to 89° degrees, and most preferably range from 86° to 89° relative to the longitudinal axis in the as patterned configuration or in the as delivered configuration.

In some instances, the expandable coil may be attached to distal end of the tubular catheter body, incorporated within the distal end of the tubular catheter body, or coupled to the distal end of the tubular catheter body. In some other instances, the expandable coil may extend from the distal end of the tubular catheter body to a proximal end, or to the proximal end of the tubular catheter body. The expandable coil in some instances maybe attached to a proximal end of the tubular catheter body.

In some instances, expandable coil is embedded or laminated in the expandable membrane or embedded or laminated in the tubular catheter body.

In some instances, the expandable coil may have a crimped delivery configuration and an expanded deployed configuration.

In some instances, the crimped delivery configuration of the expandable coil has a maximum outer diameter in a range from 0.5 mm to 30 mm and the expanded deployed configuration has a maximum outer diameter in a range from 1.5 mm to 40 mm.

It should be appreciated that all features and aspects of the apparatus and methods of the present invention described herein may be arranged in different combinations and are covered by the claims even if no specific embodiments or examples of the particular combinations have been provided. The features which are described in whole or in part in all paragraphs, examples, embodiments, drawings and other aspects as set forth herein may be combined in ways not specifically described and may be part of this invention.

BRIEF DESCRIPTION OF THE DRAWINGS

FIG. 1A illustrates a second system comprising (1) an aspiration catheter having an expandable distal tip and (2) a distal tip expansion catheter constructed in accordance with the principles of the present invention.

FIG. 1A-1 is a detailed view of a region defined by boundary line 1A-1 to 1A-1 of FIG. 1A.

FIG. 1A-2 is a detailed view of a region defined by boundary line 1A-2 to 1A-2 of FIG. 1A.

FIG. 2A is a detailed view of an example of an expandable distal tip of the aspiration catheter of the system of FIG. 1 shown in a non-expanded configuration (or in as delivered configuration) with a portion of a cover (or laminated) membrane removed or broken away to expose an expandable supporting scaffold or other expandable supporting structure. A reinforcement coil continuously connected to the expandable supporting scaffold or other expandable supporting structure proximal end and is formed continuously connected to the expandable supporting scaffold proximal end as shown. The expandable distal tip configuration and the non-expandable proximal segment (reinforcement coil) configuration in this example of FIG. 2A have the same delivery configuration (or have the same outer diameter profile).

FIG. 2B is a "rolled out" view of an example of the expandable supporting scaffold or other expandable supporting structure of the expandable distal tip of the aspiration catheter of the system of FIG. 1. A reinforcement structure formed continuously with the expandable supporting structure proximal end is shown.

FIG. 2C is a detailed view of an adjacent pair of circumferentially expandable supporting rings of the expandable distal tip of the aspiration catheter of the system of FIG. 1 showing supporting elements within most cells but not all and a link joining the adjacent rings.

FIG. 11A is a detailed view of an expandable distal tip of an alternative example of the aspiration catheter of the present invention having supporting scaffold comprising a plurality of rings shown in a non-expanded configuration with a portion of a cover membrane removed or broken away. FIG. 11 also shows the transition ring comprising an expandable section and non-expandable section (coil in tis example). It also shows the expandable scaffold and non-expandable coil being formed continuously from the same tube or bent wire FIG. 11B is a "rolled out" view of the supporting scaffold of the expandable distal tip of the aspiration catheter of the system of FIG. 11A showing the transition from an expandable scaffold of the distal tip to a non-expandable supporting scaffold formed as a helical coil in a body of the aspiration catheter.

FIG. 11C is a detailed view of the individual cells of the supporting scaffold of the expandable distal tip of the aspiration catheter of the system of FIG. 11A showing recessed supporting elements and a compacted pattern configuration in the as patterned configuration (or as delivered configuration). FIG. 11C also shows the arc length of crowns being about the same length as the axial length of struts.

FIGS. 14A and 14B illustrate how the "pitch angle" as referred to herein can be determined as an acute angle.

FIGS. 15A-15C are detailed exemplary views illustrating different bending patterns that can be utilized in the radially expandable distal tip rings of the present invention.

DETAILED DESCRIPTION OF THE INVENTION

Figure 1:
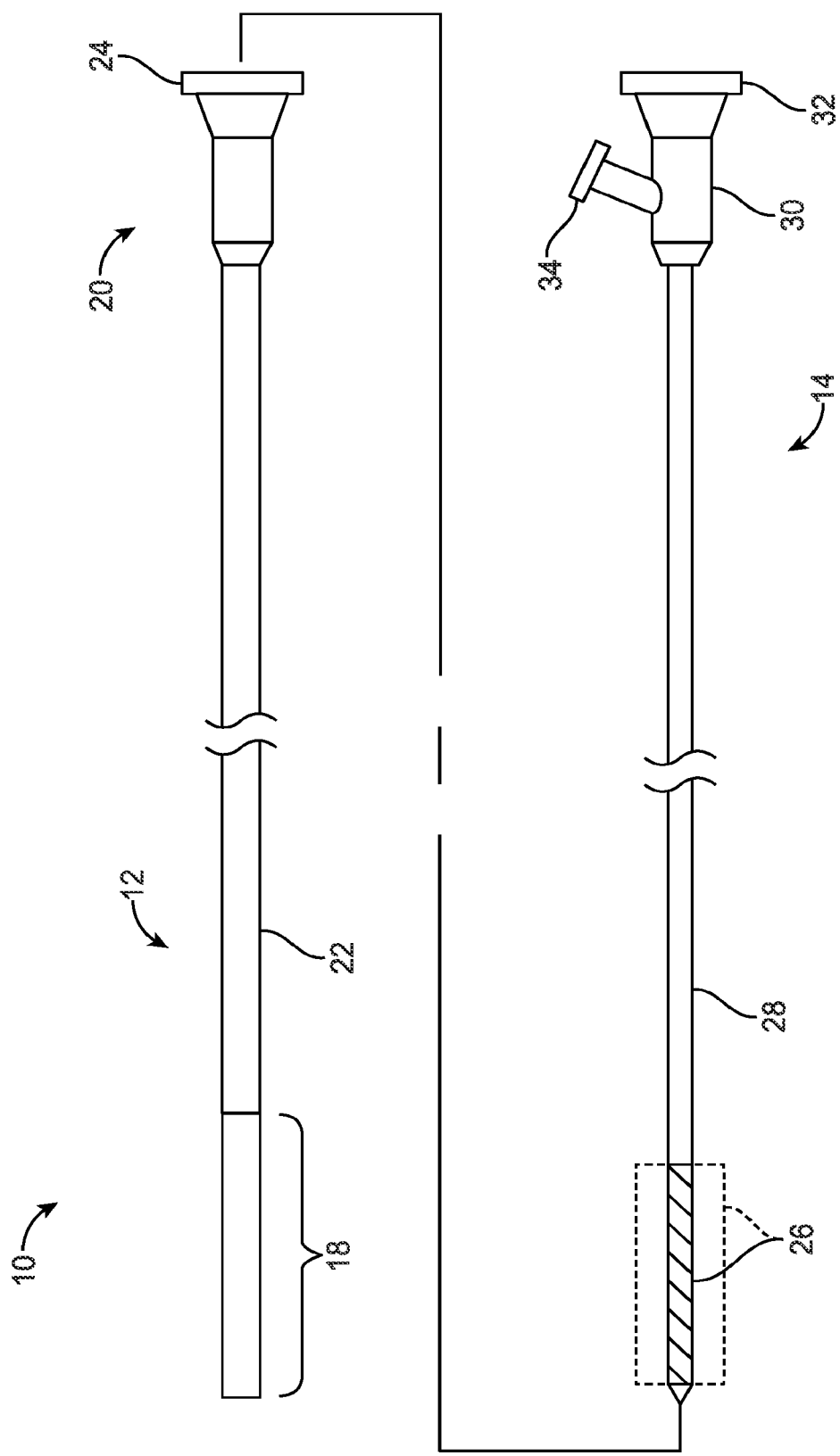
FIG. 1 illustrates a first system comprising (1) an aspiration catheter having an expandable distal tip and (2) a distal tip expansion catheter constructed in accordance with the principles of the present invention.

Referring now to FIG. 1, a system 10 for removing clot from a patient's vasculature, typically the cerebral vasculature, comprises an aspiration catheter 12 and a distal tip expansion catheter 14, typically an inflatable balloon catheter. The aspiration catheter 12 has an expandable distal tip 18 at a distal end of a tubular body 22 and a proximal hub 20 at a proximal end of the tubular body. The tubular body 22 has an aspiration lumen extending from its distal end to the proximal end, and a luer fitting/connector 24 is configured to attach to a syringe or other vacuum or negative pressure source of the type typically found in a hospital or other medical care facility. By applying a negative pressure to the luer fitting/connector 24, clot can be aspirated into an open distal end of the expandable distal tip 18 as described in more detail below. The drawings of system 10 shows a proximal hub 20 having a luer fitting/connector 24 which is connected to a guidewire lumen (not shown) which is also the same lumen as the aspiration lumen in this example. The guidewire is typically removed prior to attaching luer fitting/ connector 24 to a vacuum pump in order to maximize the suction forces. In another example, the system 10 may be adapted to have a proximal hub similar to proximal hub 30 in which luer fitting/connector 34 would be connected to a vacuum pump, while luer fitting/connector 32 would be connected to a guidewire lumen (not shown).

The distal tip expansion catheter 14 comprises a balloon or other expandable member 26 at a distal end of shaft 28. A proximal hub 30 is attached to a proximal end of the shaft 28 and includes a first luer connector 32 and a second luer connector 34. The first luer connector 32 is connected to a guidewire lumen (not shown) which extends the entire length of shaft 28 and allows the catheter 14 to be advanced over a guidewire or a microcatheter to target location in the patient's cerebral or other vasculature. The second luer connector 34 is configured to connect to the balloon inflation lumen (not shown) in the shaft 28 which allows to expand the expandable distal tip 18 of the aspiration catheter 12 proximate a target clot in the patient's vasculature, as will be described in more detail below.

FIG. 1A illustrates a second exemplary aspiration catheter 112 suitable for use with the distal tip expansion catheter 14 of FIG. 1. The aspiration catheter 112 has a similar construction as that of the aspiration catheter 12 and includes an expandable distal tip 118 at a distal end of a tubular body 122 and a proximal hub 120 at a proximal end of the tubular body. The tubular catheter body 122 has an aspiration lumen extending from its distal end to the proximal end, and a luer fitting 124 at the proximal end of the tubular body 122 is configured to attach to a vacuum pump or negative pressure source of the type typically found in a hospital or other medical care facility. By applying a negative pressure to the luer fitting/connector 124, clot engaging the distal tip can be aspirated into an open distal end of the expandable distal tip 118 as described in more detail below. The drawing of an aspiration catheter 112 shows a proximal hub 120 having a luer fitting/connector 124 which is connected to a guidewire lumen (not shown) which is also the same lumen as the aspiration lumen in this example. The guidewire is typically removed prior to attaching luer fitting/connector 24 to a vacuum pump. In another example, the aspiration catheter 124 may be adapted to have a proximal hub similar to proximal hub 30 of FIG. 1, in which luer fitting/connector 34 would be connected to a vacuum pump, while luer fitting/connector 32 would be connected to a guidewire lumen (not shown).

In contrast to the aspiration catheter of FIG. 1, the expandable scaffold 118 of aspiration catheter 112 is connected to or attached at or coupled to at its proximal end to typically a non-expandable reinforcement structure such as coil 128, typically a helical ribbon, which may be formed integrally (or continuously) with the helical expandable scaffold 118. While the reinforcement coil 128 may be formed from the same balloon expandable scaffold material (e.g. a malleable metal comprising a metal or metal alloy) as the expandable scaffold of the distal tip 118, the reinforcement coil will typically not be radially expandable by the distal tip expansion catheter (such as a balloon catheter) as it is not configured with an undulating pattern comprising bends and struts or otherwise to allow radial expansion, as described in greater detail herein below. In some instances, the reinforcement coil 128 will typically have the same thickness as the thickness of the expandable scaffold of the distal tip 118. Similarly, the reinforcement coil 128 will typically have an absolute pitch angle similar to the pitch angle of the expandable scaffold, wherein the pitch angle preferably ranges from 80° to 89.9° relative to the longitudinal axis in the as patterned configuration or in the as delivered configuration. In some other instances, the reinforcement coil 128 will have an absolute pitch angle ranging from 70° to 89.9°, preferably ranging from 80° to 89.9° relative to the longitudinal axis in the as patterned configuration or in the as delivered configuration. In some instances, the reinforcement coil 128 will typically have width ranging from about the same width as the expandable rings of the expandable scaffold to 3 times the width of the expandable rings of the expandable scaffold of the expandable tip 118. In some other instances, the reinforcement coil 128 has a width ranging from 0.05 mm to 0.25 mm, and has a gap ranging from 0.025 mm to 0.25 mm. In some examples the gap between coils is fixed. In other examples, the gap between coils is variable. In some instances, the reinforcement coil 128 is formed integrally from the same tube or bent wire forming the expandable scaffold of the expandable tip 118. The tube or bent wire is patterned to form a plurality of adjacent ribbons, rings, or turns, joined continuously, end-to-end in a helical arrangement, typically patterned by laser, bent wire, or other means. In other instances, the reinforcement coil 128 is formed from a bent wire forming a plurality of adjacent turns joined continuously, end-to-end in a helical arrangement. In this example, the expandable scaffold of the expandable tip 118 is formed from the same tube as coil 128, wherein the expandable scaffold is formed from a tube patterned to form a plurality of adjacent rings joined continuously, end-to-end in a helical arrangement, wherein each ring comprises structural elements comprising struts joined by crowns, and wherein the expandable coil scaffold have an absolute pitch angle ranging from 70° to 89.9°, or preferably ranging from 80° to 89°. For example, the distal tip expandable scaffold 118 may be jacketed with an expandable membrane comprising one or more membranes wherein the one or more membranes are elastic and/or inelastic but stretchable membranes (allowing expansion) covering the expandable scaffold 118 and extending from the distal end of the distal tip to at least a proximal end of the expandable scaffold. In some instances, the expandable membrane extends proximally to the proximal end of the expandable scaffold to cover at least a segment of the reinforcement coil 128, or in some cases extends proximally to cover substantially the entire length of the reinforcement coil 128. while in some other cases, the reinforcement coil 128 may be jacketed with one or more elastic membrane and/or inelastic membrane (resisting expansion) different from the one or more membranes covering the expandable scaffold 118. In some instances, the one or more expandable membranes covering the expandable scaffold are attached to an inner and/or to an outer surface of the expandable scaffold. In other instances, the expandable scaffold is laminated within, or embedded in or within, or coated by the one or more expandable membranes covering an outer surface and/or covering an inner surface of the expandable scaffold. In some instances, the expandable scaffold is covered by at least two membranes, wherein one membrane is attached to an outer surface of the expandable scaffold while the other is attached to an inner surface of the expandable scaffold. In other instances, an aspiration catheter comprising an expandable tip, wherein the expandable tip comprises an expandable membrane and an expandable supporting structure such as a scaffold where the expandable scaffold comprises a plurality of rings spaced-apart along the longitudinal axis with gaps therebetween and within each of the rings, wherein the rings comprise structural elements comprising struts and crowns. The expandable scaffold is embedded in or within the expandable one or more membrane(s), wherein the expandable membrane covering the scaffold comprises at least one membrane wherein the at least one membrane is softened and/or melted over an outer surface of the expandable scaffold and/or over an inner surface of the expandable scaffold, allowing the one or more expandable membrane(s) to soften or melt allowing and to protrude or flow into the gaps present within each ring (within each ring structural elements) and into the gaps present between rings, and said material adhere to said rings (rings structural elements), providing an integrally expandable scaffold/membrane(s) system, expandable from contracted or as delivered configuration to an expanded larger configuration. The expandable membrane, in a preferred aspect, covers an outer and/or an inner surface of the expandable supporting structure or scaffold, and also covers at least some gaps present within each ring of the expandable scaffold and gaps present between adjacent rings of the expandable scaffold, wherein covers comprises one or more of coat, provide fluid seal, fills, flows into, flow onto, or protrude into, or adheres to, embedded in, laminated within, an outer surface of the scaffold, an inner surface of the scaffold, and/or gaps in between the outer surface and inner surface of the scaffold wherein the covering membrane(s) adhere sufficiently to the scaffold rings structural elements to provide an integrated system being capable to jointly expand from an as delivered configuration to an expanded configuration as an integrated system. The expandable membrane in a preferred aspect covers at least some, preferably covers most, most preferably covers all of the following: flows into gaps present between each of the rings, within each of the rings structural elements comprising struts joined by crowns, wherein the one or more expandable membranes in a preferred aspect covers an outer surface and/or inner surface of the expandable scaffold, and covers at least some side surfaces of the expandable scaffold structural elements, preferably covers substantially all side surfaces of the expandable scaffold structural elements, and covers substantially all gaps between adjacent rings of the expandable scaffold. The expandable scaffold in a preferred aspect comprises an outer surface, an inner surface, and two side surfaces. In other aspect, an expandable scaffold is formed from a bent wire comprising an outer surface and an inner surface. In some other instances, the reinforcement coil material 128 may be formed from a different material than the expandable scaffold material 118, such as formed from a shape memory metal material, or formed from other malleable metal or metal alloy material, and is then attached to the expandable scaffold proximal end by solder or is coupled to the expandable scaffold proximal end by abutting or intertwining (nesting or interweaving) the two material ends and covering them by one or more membrane(s) to hold them together. One or more membrane(s) covering coil 128 can be the same one or more membrane(s) covering the expandable scaffold 118. In another example, at least one membrane covering coil 128 is the same membrane covering the expandable scaffold 118, typically, at least the inner surface membrane covering both the expandable scaffold 118 and the reinforcement coil 128. The expandable coil scaffold 118 may be formed from a tube forming a plurality of circumferentially expandable rings comprising structural elements comprising struts joined by crowns. Likewise, the reinforcement non expandable coil 128 may also be formed from the same tube forming helical ribbons. The expandable scaffold rings, structural elements, struts, and crowns, and the helical ribbon of the reinforcement coil each have an outer surface, an inner surface, and at least two side surfaces. In other example, the expandable coil scaffold and reinforcement non expandable coil may be formed alternatively from a bent wire forming the expandable coil 118 and the reinforcement coil 128.

The catheter body 122 includes two additional regions, i.e., an intermediate region 130 typically reinforced with a helical ribbon and a proximal region 132 typically reinforced with braid. The intermediate region 130, will have an "intermediate" flexibility between that of the flexible regions of 118 and 128 and that of the more rigid and pushable proximal region 132. A distal end of the proximal region 132 is connected to a proximal end of the intermediate region 130 by overlapping their ends and covering the junctions 1A-1 with a first adhesion jacket 140 wherein the adhesion jacket comprise one or more membrane(s) heated sufficiently to soften and/or to melt the material and wherein the material flows into or protrude into the metallic structure gaps, sufficiently to adhere to the metallic structures, holding the two structures, regions or segments together, and a distal end of the intermediate region 130 is connected to the reinforcement coil 128 by nesting their ends (intertwining their ends) and covering the junctions 1A-2 with a second adhesion jacket 142 wherein the adhesion jacket comprise one or more membrane(s) heated sufficiently to soften and/or to melt the material and wherein the material flows into or protrude into the metallic structure gaps, sufficiently to adhere to the metallic structures, holding the two structures, regions or segments together. The adhesion jackets may be the same or different. As seen in FIGS. 1A-1 and 1A-2, the outer adhesion jackets 140 and 142 typically overlap a few nested or intertwined coils of the coiled regions junction 1A-2 or a longer segment than junction 1A-2, or overlap some distance, preferably short distance on the coil region/braided region overlapped junction 1A-1 of the proximal region 132. The intermediate region 130 is typically formed integrated with or continuously with region 128 and 118 and is typically a helical coil configured to have a pitch angle, width, and gaps different than region 128 helical coil to provide better push transmission. In other examples, regions 128 and 130 are formed having the same pitch angle, width, and gaps between coils, and wherein the combined regions 128 and 130 are joined to a braided proximal shaft 132. In yet some other examples, intermediate region 130 is formed from a different metal such as shape memory metal or metal alloy such as Nitinol, formed as a coil having a pitch angle, coil width, and gap between coil to enhance flexibility and pushability of the intermediate region 130. The expandable scaffold of region 118 is preferably formed from a tube but can also be formed from a bend wire. Region 128 is preferably formed from the same tube that forms expandable region 118 in an integrated manner. Region 130 typically formed from the same tube forming regions 128 and/or region 118 but may also be formed from a different material or tube, or bent wire. In a preferred example, region 18 expandable scaffold is patterned from a tube forming structural elements having an outer surface, an inner surface, and side surfaces, wherein the structural elements comprise struts joined by crown forming a plurality of adjacent rings being expandable from a crimped configuration to an expanded configuration. Regions 128 and 130 are formed preferably from a tube, preferably the same tube, forming expandable scaffold region 118 in an integrated manner, where region 128 is formed in the form of a helical coil. While reinforcement structure is typically a coil, other types of reinforcement structures such as scaffold, supporting scaffold may be substituted for the coil in region 128, and are usually formed continuously with the expandable supporting scaffold of region 118. In other instances region 118 maybe formed from a shape memory alloy such as nickel titanium alloy and is constraint in the as delivered configuration before being released to expand from the as delivered configuration to an expanded configuration.

Figure 1B:
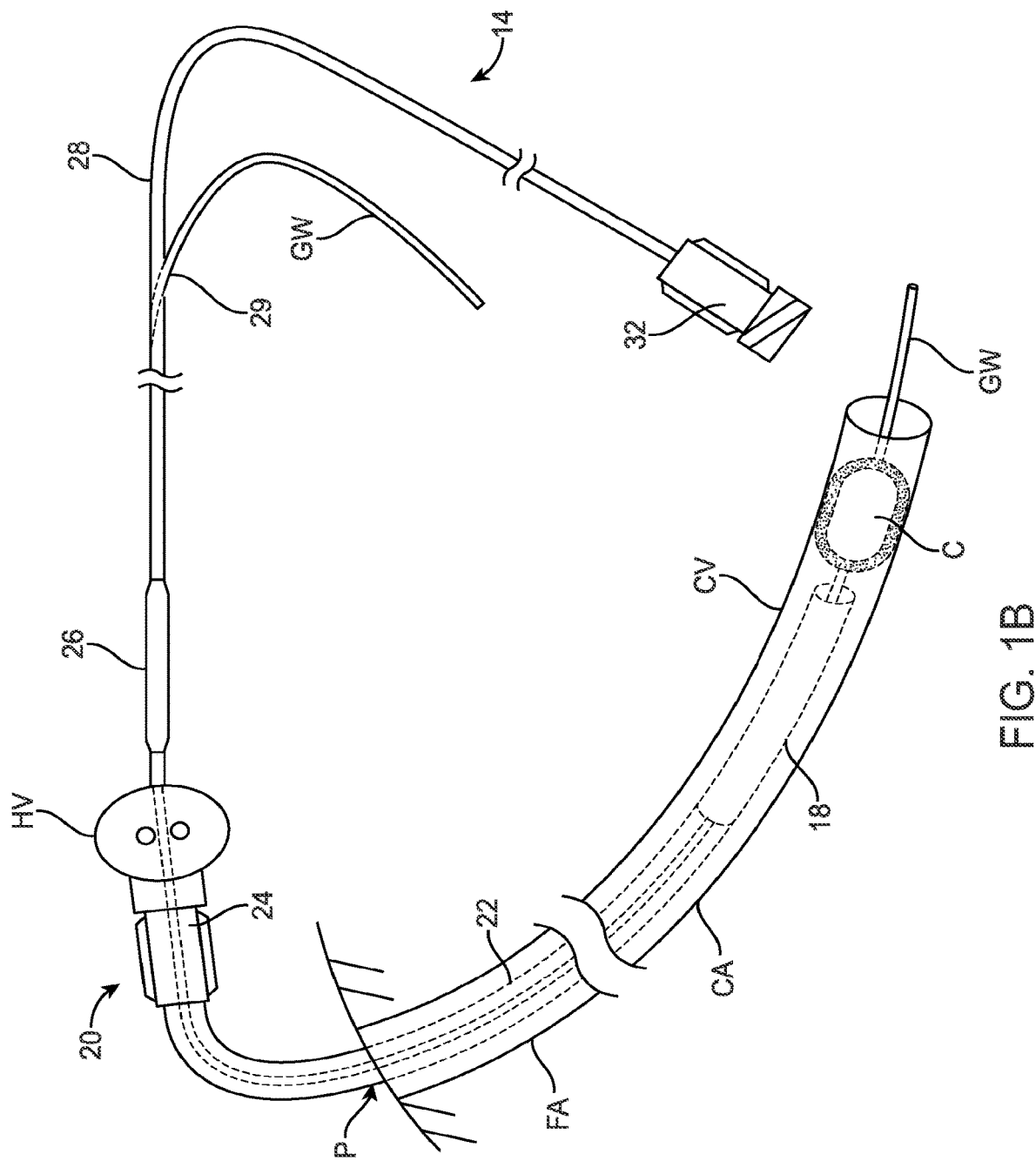
FIG. 1B illustrates the system of FIG. 1A as it is being introduced via a femoral artery to a target location in the cerebral vasculature.

FIG. 1B illustrates the system of FIG. 1 as it is introduced via a femoral artery FA to a target location with clot C in the cerebral vasculature CV. A guidewire GW is introduced into the femoral artery FA through a sheath (not shown). The aspiration catheter 12 of FIG. 1 or FIG. 1A is introduced over the guidewire GW and advanced through the femoral artery FA and through the aorta A through a guiding catheter and/or a guiding sheath (not shown) into for example the target cerebral artery CA until the expandable distal tip 18 is positioned adjacent the target clot C or engaging the target clot C. The distal tip expansion catheter 14 is then advanced over the guidewire through a hemostasis valve HV, and the expandable member 26 advanced until it is located within the expandable distal tip 18. The expandable member 26 is then expanded, typically by inflation, in order to expand the distal tip 18 so that its outer surface generally engages the clot and/or seals against the inner wall of the cerebral artery and/or expand towards the inner wall of the cerebral artery at a position adjacent to the clot C. The geometry of the expanded distal tip 18 can vary, as described hereinafter, catheter 14 is then removed, and in all cases a vacuum pump or negative pressure will be applied through the proximal hub 20 in order to draw clot C into the aspiration catheter 12 so that it may be removed from the vasculature.

Referring now to FIGS. 2A to 2C, the construction of expandable distal tip 18 of the aspiration catheter 12 in FIG. 1 will be described in more detail. The expandable distal tip 18 includes both an expandable supporting scaffold 38 and an expandable membrane 40. As described previously, the expandable membrane 40 will typically comprise one or more of an elastic or stretchable inelastic polymeric membrane having the supporting scaffold 38 embedded or laminated therein covering the scaffold. The supporting membrane(s) typically flow into, protrude, or otherwise adhere to the supporting scaffold structural elements providing an integrated expandable scaffold membrane system. The supporting scaffold 38 will typically comprise a metal or metal alloy, typically formed from a malleable metal or metal alloy, the scaffold is configured for balloon expansion but in other cases could be configured for self-expansion after release from constraint.

The supporting scaffold 38 includes a plurality of radially expandable circumferential supporting rings 42, and each ring is separated from an adjacent ring by a gap. The rings will usually comprise undulating pattern such as serpentine, box, or zig-zag pattern including struts 48 joined by crowns 50 where adjacent rings 42 may be connected by axial one link 46. The supporting scaffold 38 shows perpendicular rings having about 90° relative to the longitudinal axis, the supporting scaffold 38 may alternatively be formed from a plurality of rings having an acute pitch angle, the pitch angle preferably ranges from 70° to 89.9°, relative to the longitudinal axis in the as patterned or as delivered configuration (not shown). In a preferred example, adjacent rings are joined by one link, or no more than one link, or no more than 2 links (not shown). Links can have a variety of shapes such as offset linear (as shown) or other types of shapes linear or non-linear such as U, M, Z, S, or other shapes. In another example (not shown), at least some adjacent rings are not joined together but are held together by a membrane covering, shrunk onto, coated over, or melted over, said at least some rings, allowing said rings to be held together in the as delivered configuration and to expand from an as delivered configuration to an expanded configuration. While adjacent rings are typically joined by one or more links, alternatively, sometimes structural elements on adjacent rings are soldered or fused or attached together joining the adjacent rings in one or more location. Alternatively (not shown), the supporting scaffold 38 may be formed from an expandable coil wherein the expandable coil comprises a plurality of adjacent expandable rings (or turns) joined continuously, end-to-end in a helical arrangement, each ring comprises structural elements comprising supporting elements and struts joined by crowns, and the expandable coils have an acute pitch angle ranging from 70° to 89.9°, preferably ranging from 80° to 89°, relative to the longitudinal axis in the as patterned or as delivered configuration. The expandable rings of the expandable coil of the supporting scaffold are joined continuously, end-to-end in a helical arrangement, and are typically not joined otherwise (such as by links or by attaching structural elements or attachment points on adjacent rings). In some limited instances, at least some rings of the expandable coil may be joined by one or more links or joined by attaching structural elements on adjacent rings, typically on rings at a proximal end of region 118 of FIG. 1A to provide support. In a preferred example, the expandable coil is expanded from an as delivered configuration or a contracted configuration to an expanded configuration by an expandable supporting structure radially expanded in an interior of the expandable coil such as a balloon catheter, wherein said expandable coil is said to be balloon expandable. Alternatively, the supporting scaffold may be formed from a bent wire forming a plurality of adjacent turns joined continuously, end-to-end in a helical arrangement. The expandable coil may be formed from a tubular body and patterned into said expandable coil comprising a plurality of circumferentially expandable rings. In a preferred example, there is a gap between at least some rings of an expandable scaffold, preferably there is a gap between all adjacent rings of an expandable scaffold. As shown in these drawings, gaps between adjacent rings are typically fixed (FIGS. 2A, 2B, and 2C), but in some instances gaps may have variable axial lengths (not shown).

In an exemplary embodiment of the present invention, supporting elements 52 of the expandable scaffold 38 are located between adjacent pairs of struts 48 and have a base end 56 attached to an inner radius of the crown 50 which joins the struts with adjacent supporting members facing in opposite axial directions. In this way, the supporting elements 52 strengthen a region of the expandable membrane 40 which spans (extends across) the struts 48. Furthermore, supporting elements 52 length in this preferred example, is equal to or shorter than the ring period, thereby not extending into the gap region between adjacent rings (as shown). This enhances deliverability of the scaffold and strengthens the region of the expandable membrane. The supporting elements 52 length is longer than ½ the length of an adjacent strut and the said length is equal to or shorter than the adjacent ring period (as shown). This provides a balance between strengthening the region of the expandable membrane and enhances deliverability of the scaffold. The supporting elements 52 in this example, have an axial length, a base, and a free end, wherein the free end terminate at or prior to the start of the gap region between rings (as shown). In yet rare instances, the supporting elements length may extend beyond the peak of an adjacent crown, extending into the gap region between rings (not shown). In this preferred example, the supporting elements 52 within each ring have the same length. In this preferred example, the supporting elements 52 within at least some rings, or within the entire length of the scaffold, have the same length (as shown). However, supporting elements within one ring may have different lengths (not shown), or supporting elements on adjacent rings may have different lengths (not shown), or supporting elements on at least some rings are different (not shown). In some examples, the width of the supporting elements 52 is the same within each ring and also within a plurality of rings (as shown). However, width of the supporting elements may be different within one ring or within a plurality of rings (not shown). In a preferred example, the width of the supporting elements 52 is about the same width of an adjacent structural element such as an adjacent crown or strut. Alternatively, the width of the supporting elements 52 is equal to or larger than the width of an adjacent structural element such as an adjacent crown or strut. In yet other examples, the width of the supporting elements 52 is larger than the width of an adjacent structural elements such as an adjacent crown or strut. In yet other example, the width of the supporting elements 52 is smaller than the width of an adjacent structural elements such as an adjacent crown or strut. In some instances, the width along the length of a supporting element or along a structural element such as a strut or a crown may vary. In such examples, the width is the average of the maximum width and minimum width along the length of the supporting element or structural element. Each of the supporting elements 52 has a base end 56 which is attached/connected to the radially expandable circumferential support ring 42. The base end 56 typically has the same width as the rest of the supporting element (as shown) but in other examples, the base may have a larger width than the supporting element width. Each of the supporting elements has a free end 58 which extends into the region between the adjacent struts. The free end 58 has a rounded shape (as shown), or in other examples may have a flat shape (not shown), T shape (not shown) or other shapes or configurations. While the supporting elements 52 are shown to be attached to an inner radius or wall of crowns 50 and to be linear, in other examples, the supporting elements may be attached to other locations on the support rings 42 such as attached to struts, and to be linear or non nonlinear. In the present example, at least some supporting elements are connected to each radially expandable circumferential support ring 42. In the present example, at least some supporting elements are connected to at least some radially expandable circumferential support ring 42. In the present example, at least some supporting elements are connected to substantially all radially expandable circumferential support ring 42. In the present example, at least some radially expandable circumferential support rings, wherein each ring comprising a plurality of cells, wherein each cell comprises struts joined by a crown, wherein at least one supporting element is connected to each cell (as shown) on the at least some expandable rings. In the present example, at least one radially expandable circumferential ring, wherein the ring comprising a plurality of cells, wherein each cell comprises struts joined by a crown, wherein at least one supporting element is connected to each cell on the expandable ring (as shown). In the present example, at least one radially expandable circumferential ring, wherein the ring comprising a plurality of cells, wherein each cell comprises struts joined by a crown, wherein at least some supporting elements are connected to at least some cells on the expandable ring (as shown FIG. 2C). In the present example, at least some radially expandable circumferential support rings, wherein each ring comprising a plurality of cells, wherein each cell comprises struts joined by a crown, wherein at least some supporting elements are connected to at least some cells on the at least some expandable rings (as shown). A variety of attachment locations and supporting member geometries are described with reference to FIGS. 7A to 7AR-2 hereinbelow.

Typically, but not necessarily, the supporting scaffolds 38 will be laser cut from metal tubes, for example, in the "rolled out" pattern shown in FIG. 2B. That pattern includes a helical coil 44 (helical coil 128 of FIG. 1A) patterned continuously from the same tube that formed the expandable scaffold, the helical coil 44 is intended to support at least a portion of one or more membrane 22, as best seen in FIG. 2A. The reinforcement coil has a length ranging from 1 mm to 100 cm, preferably ranging from 1 cm to 50 cm, and more preferably ranging from 1 cm to 25 cm. The reinforcement coil has an acute pitch angle, width, and thickness as discussed previously. The helical coil will have a gap between coils ranging from 0.01 mm to 0.25 mm. The one or more membrane 22 may be the same or different than the one or more expandable membrane 40. In one example, at least one membrane 40 extends from the distal end of the distal tip to a proximal region, wherein the proximal region is about the proximal end of coil 44. In another example, at least one membrane 22 is formed, coated, or covers at least some of the coil length, preferably covers the entire coil 44 length. In this instance, the membrane 22 is formed from a stiffer material to provide enhanced support (reinforcement) to the coil region 128 of FIG. 1A. At least one membrane 22 and at least one membrane 44 in this case typically will be joined, fused, or attached at the interface of the expandable scaffold 38 and enforcement coil 44 (as shown). The reinforcement coil 44 may have a length to extend the entire length of the tubular body 122 of FIG. 1A but will more typically extend over only a shorter transition region at a distal end of the tubular body. Proximal portions of the tubular body 122 typically may have braided or other forms of reinforcement.

As the shown in FIGS. 1 and 2A-2C, the expandable distal tip 18 of the aspiration catheter and the supporting scaffold 38 are in their non-expanded configurations (or are in the as delivered configuration) which are suitable for introduction through the patient's vasculature to a target clot location. Also, as shown in FIG. 2A, the expandable scaffold 38 and the reinforcement coil 44 connected to the proximal end of the expandable scaffold have the same inner and/or outer diameter, or have the same configuration, the as delivered configuration, to facilitate introduction through the patient's vasculature. Alternatively (not sown), the expandable scaffold segment 38 can has a smaller as delivered configuration than the as delivered configuration of reinforcement coil segment connected to the proximal end of the scaffold to enhance deliverability of the aspiration catheter. Once at the target clot location, however, the expandable distal tip 18 and supporting structure 38 will be expanded to engage a clot or a wall of the blood vessel adjacent to clot, as described in more detail with reference to FIGS. 10A-10G hereinbelow. The supporting elements in FIGS. 2A to 2C comprising at least one supporting element contained within each cell on one ring, or contained within at least some cells on one ring, form a circumferential envelop about the scaffold circumference along a scaffold length or along the entire length of the scaffold. The circumferential envelop typically has a fixed axial length, width, shape, number of supporting elements per ring, pitch angle, and/or geometry (as shown), and provides support to the one or more expandable membranes to resist collapse of the one or more expandable membranes after expansion from an as delivered configuration to an expanded configuration and a vacuum is applied at a proximal end of the aspiration catheter and the distal tip is blocked or plugged with clot or other substances. In this example, the supporting elements are contained within each cell on one ring, or within each ring amplitude, preferably, within the space of struts joined by crowns the same ring, wherein the amplitude comprises the axial distance between two adjacent peaks on the same ring. In some instances, the supporting elements may have varying lengths, widths, shapes, missing supporting elements (one or more cell within a ring does not have a supporting element), pitch angle, and/or geometry within a ring or along at least some rings, wherein the different widths, lengths, shapes, missing supporting element, or geometries maintains sufficient support to the expandable one or more membrane to prevent collapse of the at least one or more membranes under vacuum in the expanded configuration when the distal tip is blocked or plugged with clot or other substances.

Figure 3A:
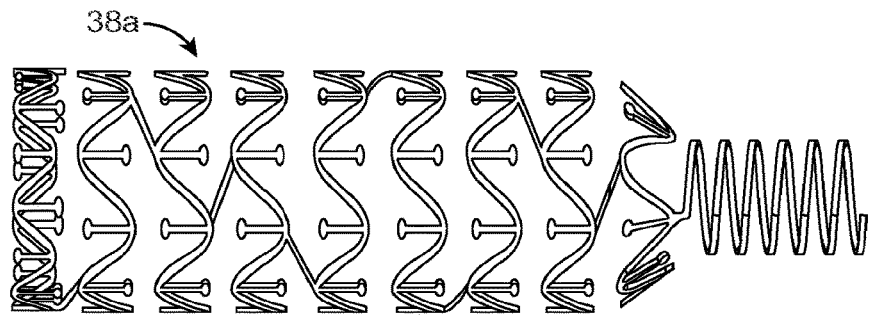
FIGS. 3A to 3D illustrate the supporting scaffold or other expandable supporting structure examples of the expandable distal tip of the aspiration catheter of FIGS. 2A to 2C shown in alternative expanded configurations.
Figure 3B:
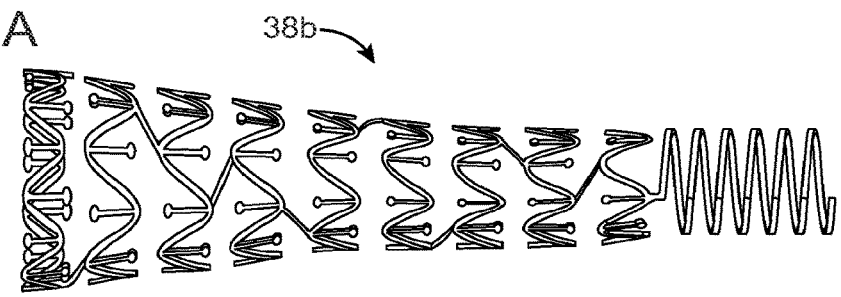
Figure 3C:
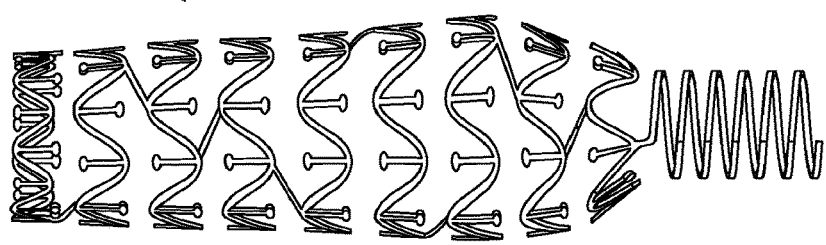
Figure 3D:
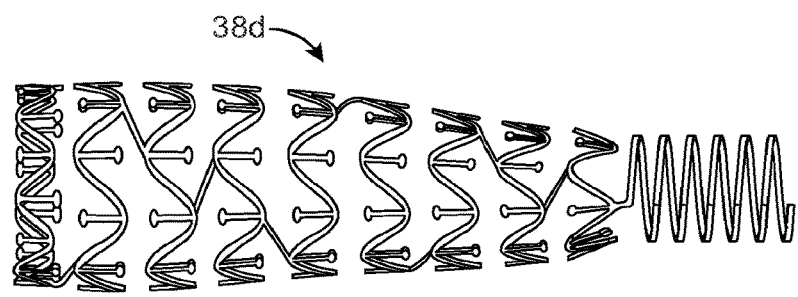

As shown in FIGS. 3A-3D, the expandable distal tip 18 (shown without the expandable membrane) may be expanded into a variety of different geometries. Often, the expanded geometry will be generally cylindrical 38a, as shown in FIG. 3A, or may have a conical tip end at the distal end of the generally cylindrical (not shown). In other instances, the expanded geometry may be generally conical 38b with a base of the cone forming an enlarged distal opening for receiving clot, as shown in FIG. 3B. In still other instances, the expanded geometry may combine expanding and tapering conical sections 38c and 38d, as shown in FIGS. 3C and 3D. Typically, the different expansion geometries will be imparted by the shape of the expandable balloon 26, i.e., the supporting scaffold 38 will be malleable and will assume the expanded shape of the expansion balloon. In other cases, however, the supporting scaffold 38 will be elastic or superelastic and be pre-shaped by heat treatment or otherwise to a desired expanded geometry when free from constraint, also such as those shown in FIGS. 3A to 3D.

Figure 3E:
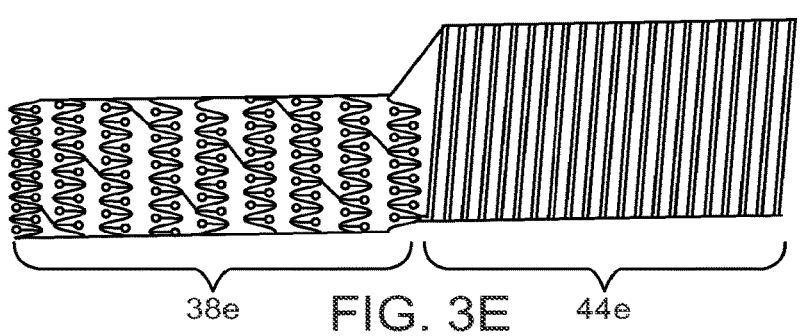
FIG. 3E illustrates a supporting scaffold (or scaffold) or other expandable supporting structure similar to that shown in FIG. 2A shown in a non-expanded configuration (or as delivered configuration) with a reduced tip configuration, relative to a proximal segment having a larger configuration, to facilitate introduction over a guidewire for enhanced deliverability into the vasculature.

Referring now to FIG. 3E, in some instances the unexpanded diameter or the as delivered diameter (configuration) of the supporting scaffold 38e may be reduced to facilitate initial introduction over a guidewire. In particular, the supporting scaffold 38e may have an unexpanded (as delivered) reduced diameter (configuration) relative to the coil support region 44e diameter (configuration) which is representative of the diameter (configuration) of the tubular body (not shown). As shown in FIGS. 3A-3D, the proximal end of the expandable scaffold is typically continuously connected as formed to a non-expandable supporting structure such as a coil (as shown in FIGS. 3A-3D) helical coil as shown in FIG. 3E, or non-expandable scaffold (not shown), or other supporting or reinforcing structures (not shown). As sown in FIGS. 3A-3E, the distal end or turn of the reinforcement coil is connected to the proximal end ring of the expandable scaffold, on a crown peak (as shown). Alternatively (not shown), the distal end of the reinforcement coil may be connected to the proximal end ring in at least one location, in at least two locations, or in at least three locations, wherein the locations on the ring may be on a crown peak, on a crown trough, and/or on a strut. The distal end of the reinforcement coil may be connected to the proximal end ring of the expandable scaffold typically by an axial link (as shown). The axial link may be linear, nonlinear, offset, or have various shapes such as U, M, W, Z, or S. Alternatively, the distal end of the coil may be connected to one or more locations on the proximal end ring directly without a link not shown). In this example, the reinforcement coil has an acute pitch angle of about 90° relative to the longitudinal axis in the as patterned or as delivered configuration. Alternatively, the pitch angle alternatively may range from 70° to 89.9° relative to the longitudinal axis in the as patterned or as delivered configuration. Reinforcement coils in FIGS. 3A-3D show the reinforcement coil turns not being connected by links. In some other examples, the reinforcement coil may have one or more links connecting at least some adjacent turns of the coil to enhance support of the reinforcement coil region. Alternatively, at least some adjacent turns may be joined by soldering points on said adjacent turns, or by other means. FIGS. 3A-3E show the expandable scaffold comprising expandable rings and adjacent rings are connected by at least one link. In an alternative example (not shown), the expandable scaffold of 3A-3E may be formed from circumferentially expandable rings wherein at least some adjacent rings are not joined or otherwise connected (by links or other means), and wherein said adjacent rings are held together by one or more membranes laminating the expandable scaffold between layers of the tubular membranes. In a preferred example, the distal end ring of the expandable scaffold preferably has flush end and about pitch angle 90° relative to the longitudinal axis in the as patterned or as delivered configuration (as shown). In some other examples (not shown), the distal end ring of the expandable scaffold may have a tapered end. Tapered end ring may be configured by controlling the pitch angle and/or by increasing the amplitude of at least some cells (or decreasing the amplitude of at least some cells) on the end ring to achieve the desired distal end taper. The end ring may have on at least some cells within the end ring the same cells amplitudes, same cells periods, and/or same cells widths or may have on the said at least some cells within the end ring different cells amplitudes, different cells periods, and/or different cells widths.

Figure 4A:
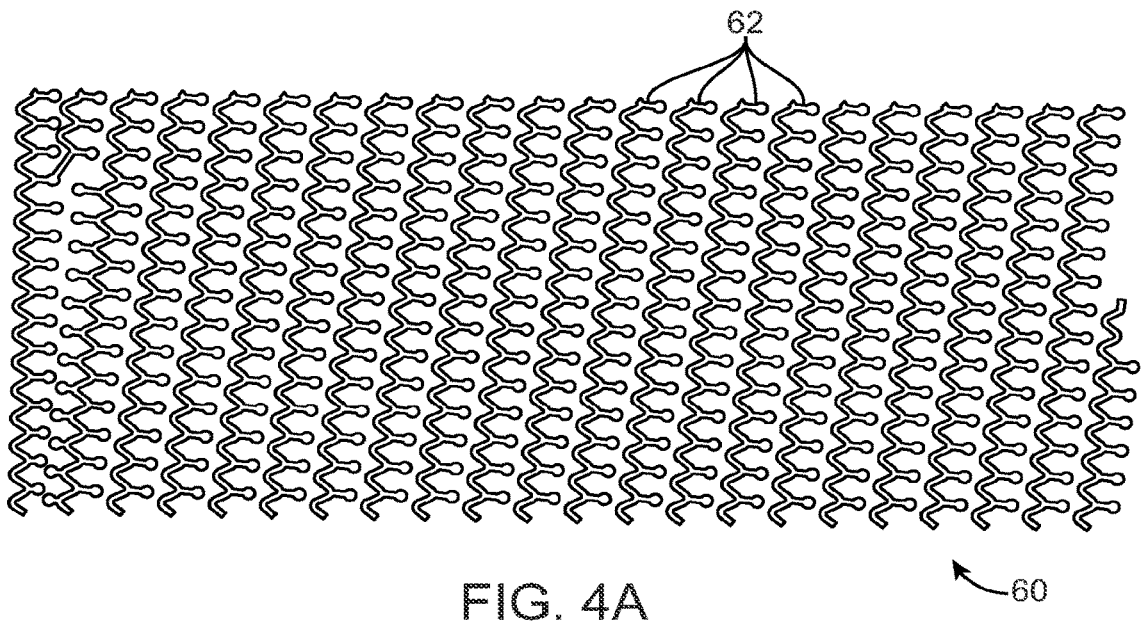
FIG. 4A is a "rolled out" view example of a supporting scaffold or other expandable supporting structure having helically arranged circumferential supporting rings constructed in accordance with the principles of the present invention.
Figure 4B:
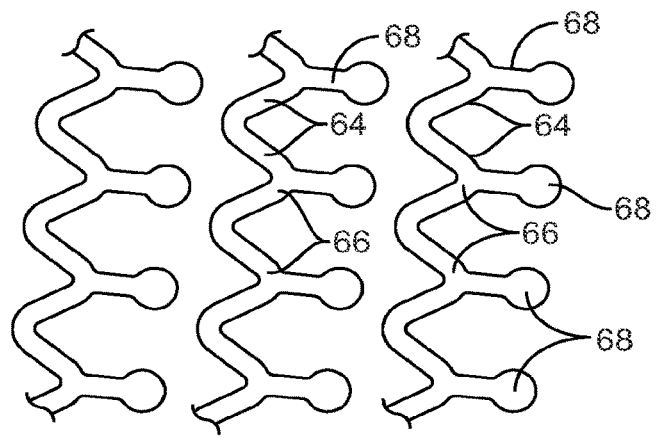
FIG. 4B is a detailed view of adjacent circumferential supporting rings of the expandable distal tip of the supporting scaffold of FIG. 4A.
Figure 4C:
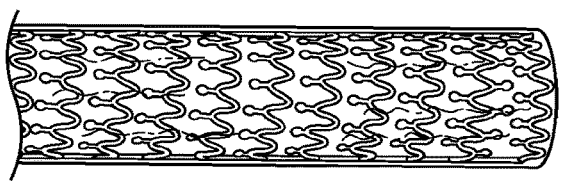
FIG. 4C is an image of the supporting cell space of FIG. 4A incorporated into polymeric tubular envelope (one or more membranes) in an unexpanded configuration (as delivered configuration).
Figure 4D:
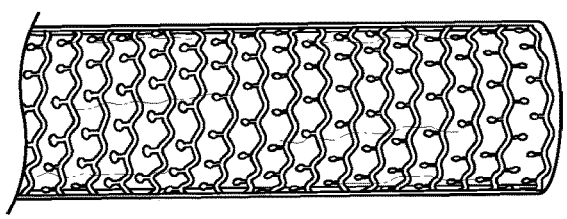
FIG. 4D is an image of the supporting scaffold and polymeric tubular envelope (one or more membranes) of FIG. 4C shown after the integrated membranes/expandable scaffold were radially expanded by a balloon from an as delivered configuration to an expanded configuration.

Referring now to FIGS. 4A to 4D, a supporting scaffold 60 pattern includes supporting elements 68 attached to the outer curved walls of crowns 66 which join adjacent struts 64. In contrast to the pattern of FIGS. 2A-2C, the supporting elements 68 do not extend between adjacent struts 64 but rather extend into a gap or open space between adjacent radially expanding circumferential support rings 62. A second difference is that the support rings 62 are joined continuously, end-to-end to form a helical pattern. FIG. 4C is an image showing an expandable region of an aspiration catheter with the scaffold pattern of FIGS. 4A and 4B in a radially constricted configuration (or as delivered configuration) suitable for delivery. FIG. 4D is an image of the same structure shown in FIG. 4C after it has been balloon-expanded to an expanded configuration, preferably to its maximally enlarged configuration suitable for aspiration. The distal end ring is configured to have a flush end with an approximately 90° pitch angle relative to the longitudinal axis in the as patterned or as delivered configuration (as shown). The end and immediately adjacent rings may be configured in various ways. The ring adjacent the end ring is this example was truncated along the circumferential path of said ring and connected to the end ring as shown in FIG. 4A. The end ring and ring adjacent the end ring may have different acute (or 90°) pitch angles (as shown). Alternatively, the ring before end and end ring may also have same or different cells amplitude, cells periods, structural elements widths, and/or number of crowns. The expandable scaffold 60 pattern has a pitch angle of about 86°. The pitch angle in other examples may range from 70° to 89.9°, preferably may range from 80° to 89° relative to the longitudinal axis in the as patterned or as delivered configuration. It is important to note that even though the supporting elements extend into gap regions (or other spaces) between adjacent rings, usually these supporting elements do not extend into adjacent ring regions, thereby maintaining enhanced deliverability of the expandable scaffold segment into the vascular anatomy.

Figure 5B:
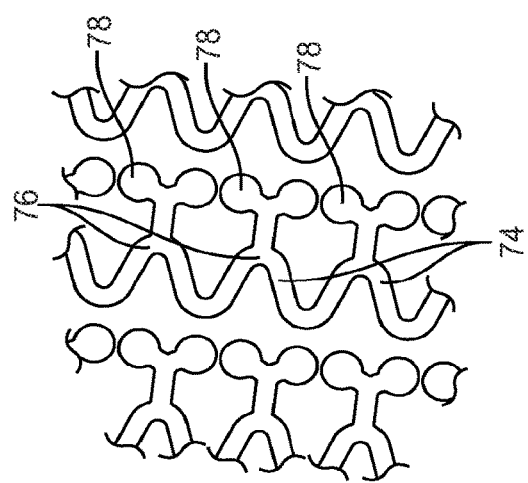
FIG. 5B is a detailed view of adjacent circumferential supporting rings of the expandable distal tip of the supporting scaffold of FIG. 5A.
Figure 5A:
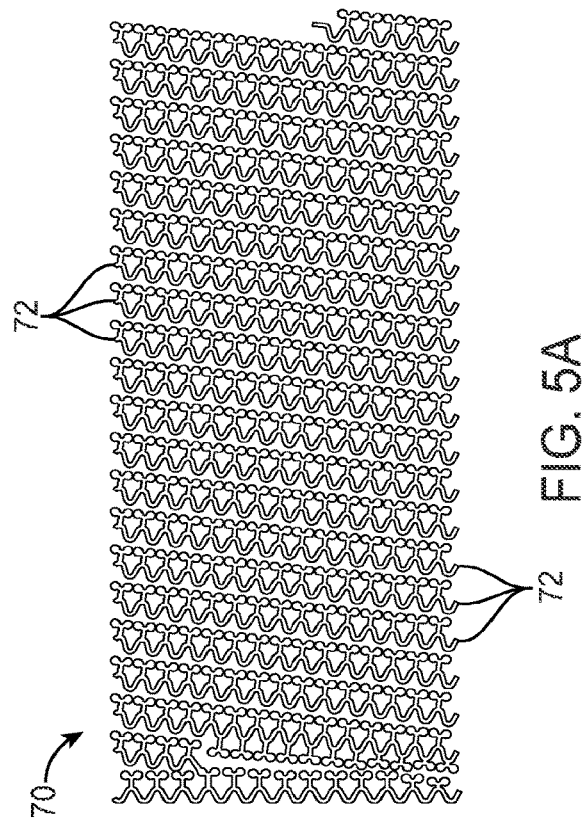
FIG. 5A is a "rolled out" view of another example of a supporting scaffold having helically arranged circumferential supporting rings constructed in accordance with the principles of the present invention.

Referring now to FIGS. 5A and 5B, a supporting scaffold 70 having a helical pattern similar to that of scaffold 60 comprises a plurality of radially expandable circumferential support rings 72 including struts 74 and crowns 76. Support elements 78 differ from support elements 68 and that they have bifurcated end support discs. The supporting elements form a circumferential envelop about the scaffold circumference along a scaffold length or along the entire length of the scaffold. The circumferential envelop typically has a fixed axial length, width, shape, and/or geometry (as shown), and provides support to the one or more expandable membranes to resist collapse of the one or more expandable membranes after expansion from an as delivered configuration to an expanded configuration and a vacuum is applied at a proximal end of the aspiration catheter with the distal tip is blocked or plugged with clot or other substances. In this example, the supporting elements base is at crowns peaks regions. The supporting elements extend axially beyond each ring amplitude or beyond at least some rings amplitude wherein the amplitude is the axial distance between two adjacent peaks on the same ring. In some instances, the supporting elements may have varying lengths, widths, shapes, or geometry within a ring or along at least some rings, wherein the different widths, lengths, shapes, or geometries continue to provide support to the expandable one or more membrane to prevent collapse under vacuum in the expanded configuration of the at least one or more membranes. As shown in FIG. 5A, FIG. 4A, and FIG. 6A, the proximal end ring of the expandable scaffold is composed of an expandable segment (shown) and a non-expandable segment (truncated), defining the transition between the expandable scaffold and the reinforcing coil. The first non-expandable reinforcement coil segment may be attached to one or more locations on the adjacent expandable ring and/or on the adjacent reinforcement coil turn, or remain free from being joined, other than being joined in a helical pattern to adjacent turns.

Figure 6B:
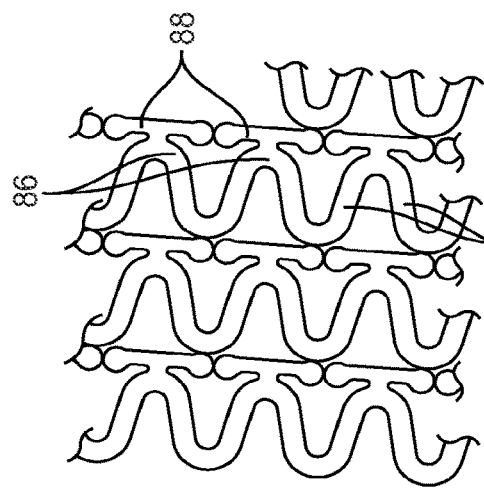
FIG. 6B is a detailed view adjacent circumferential supporting rings of the expandable distal tip of the supporting scaffold of FIG. 6A.
Figure 6A:
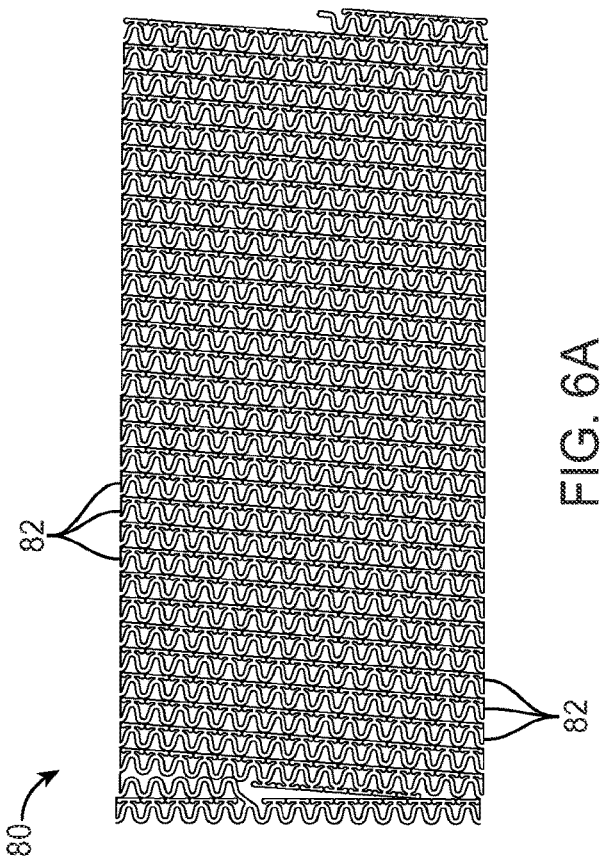
FIG. 6A is a "rolled out" view of a further example of a supporting scaffold having helically arranged circumferential supporting rings constructed in accordance with the principles of the present invention.

Referring now to FIGS. 6A and 6B, a supporting scaffold 80 has a helical pattern similar to that of scaffolds 60 and 70 comprises a plurality of radially expandable circumferential support rings 82 including struts 84 joined by crowns 86. Support elements 88 differ from support elements 68 and 78 in that they extend primarily in a circumferential direction allowing adjacent support rings 82 to be positioned very closely together in an axial direction prior to expansion. In this example, the supporting elements extend into substantially the entire gap between rings, leaving a small gap in between adjacent ring. This type of supporting elements configuration provides the one or more membranes enhanced resistance to collapse when the membranes are expanded from an as delivered configuration to an expanded configuration and a vacuum is applied at a proximal end of the aspiration catheter. On the other hand, such design configuration where the gap is small is more suitable for anatomy that is not tortuous. In this example and other example, it is important to note the symmetry of the supporting elements within each ring, preferably within at least some rings, and more preferably along substantially the entire length of the scaffold. Such symmetry provides resistance to deformation and/or kinking when navigating the vasculature. It also provides a more enhanced resistance to collapse of the expandable membrane. In some instances, one or more supporting elements may be missing within one or more rings providing a non-symmetrical supporting element pattern yet maintaining the resistance to collapse of the expandable membranes.

Figures 7A, 7B, 7C, 7D:
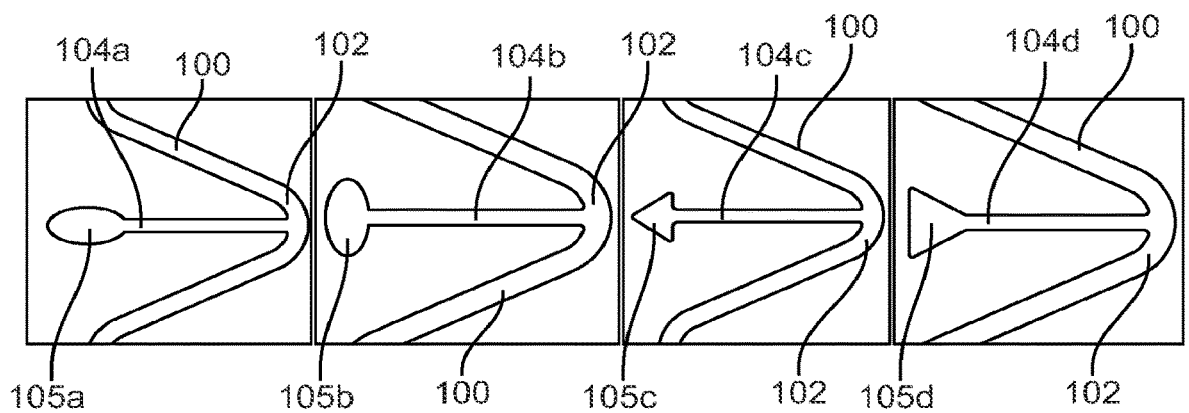
FIGS. 7A to 7AR-2 illustrate a variety of alternative examples of geometries, scaffold designs, and connection locations and shapes for the supporting elements of the present invention.
Figures 7E, 7F, 7G:
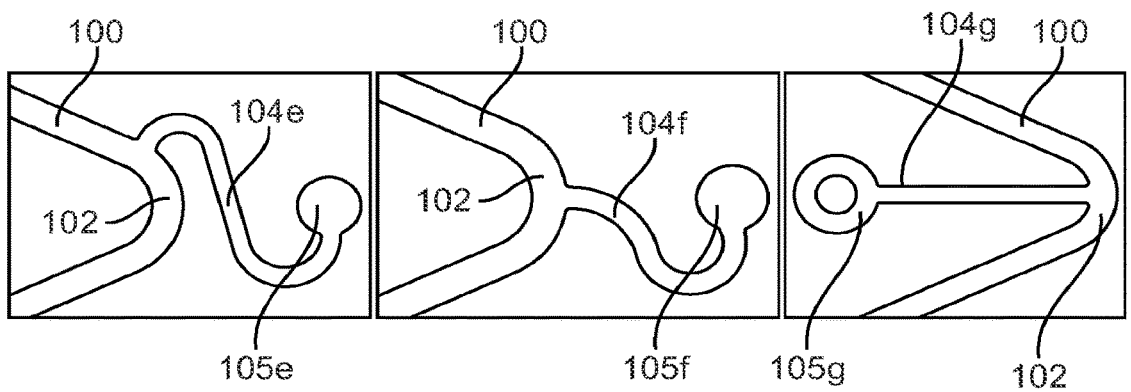
Figures 7H, 7I:
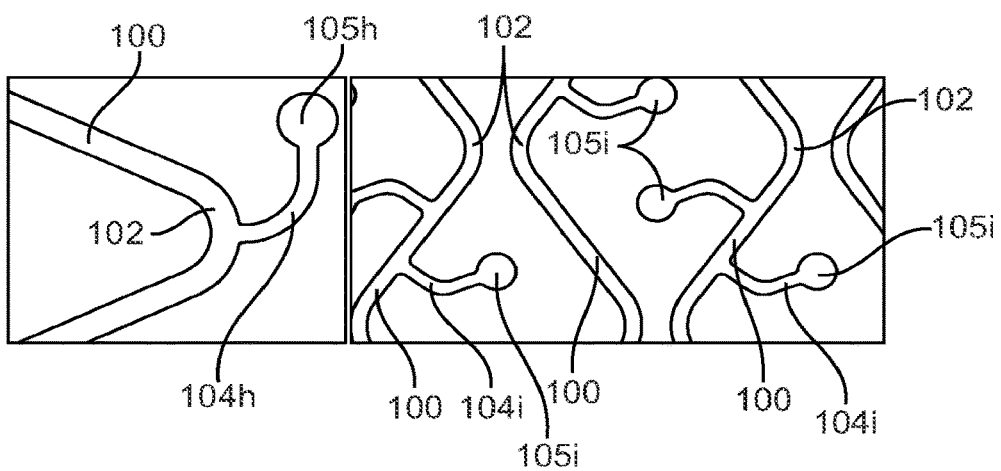

As shown thus far, the support elements have generally comprised a straight structure having a base end attached to a radially expandable circumferential support ring and a free end located in a space between adjacent struts, between adjacent struts joined by crowns, or a gap between adjacent support rings. As shown in FIGS. 7A-7N, however, the geometries and attachment locations of the support elements may vary widely. Support element 104a shown in FIG. 7A has a base end attached to an inner radius or wall of crown 102 and a free end terminating in an oval contact pad 105a in a V-shaped, ⌒-shaped space between adjacent struts 100. The oval contact pad 105a has a major axis aligned an axial direction. As shown in FIG. 7B, a support element 104b terminates in an oval contact pad 105b having a major axis aligned in a circumferential direction.

Support element 104c in FIG. 7C is similar to the previously described support elements except that it terminates in a triangular contact pad 105c with a pointed tip directed away from the attached crown. Support element 104d in FIG. 7D is similar to all of the previously described support elements except that it terminates in a triangular contact pad 105d with an expanded base directed away from the attached crown. Supporting element 104g shown in FIG. 7G has a base attached to a center of an inside wall of crown 102 and a circular contact pad 105g having a hole in its center circumferentially aligned with the attachment point.

Support elements having curved shafts are shown in FIGS. 7E, 7F, 7H, and 7I. Support element 104e shown in FIG. 7E has an S-shaped shaft with a base end attached on one side of an outer curve of crown 102 and a circular contact pad 105e circumferentially aligned with the outermost point of the crown. Supporting element 104f shown in FIG. 7F has a base attached to the outermost point on crown 102 and a circular contact pad 105f circumferentially aligned with said outermost point. Supporting element 104h shown in FIG. 7H has a base attached to the outermost point of the crown 102, a shaft with a simple 90° bend, and a circular contact pad 105h axially offset from said outermost point. Supporting elements 104i shown in FIG. 7I have their base ends attached along the length of struts 100 and circular contact pads 105i attached to their free ends. The shaft has an approximately 120° bend.

Figure 7J:
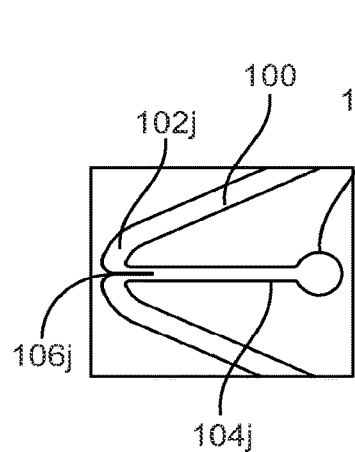

Supporting element 104j shown in FIG. 7J is similar to those shown in FIGS. 2A-2C having a circular contact pad 105j at the free end of a linear shaft but includes a short split 106j formed in crown 102j to permit an increased radial expansion.

Figure 7K:
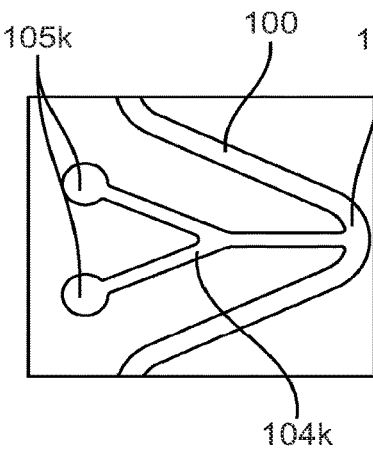
Figure 7L:
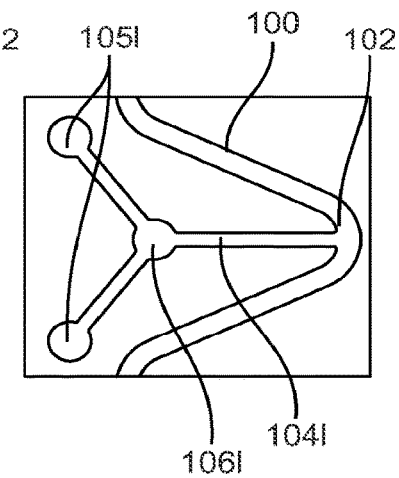
Figures 7M, 7N:
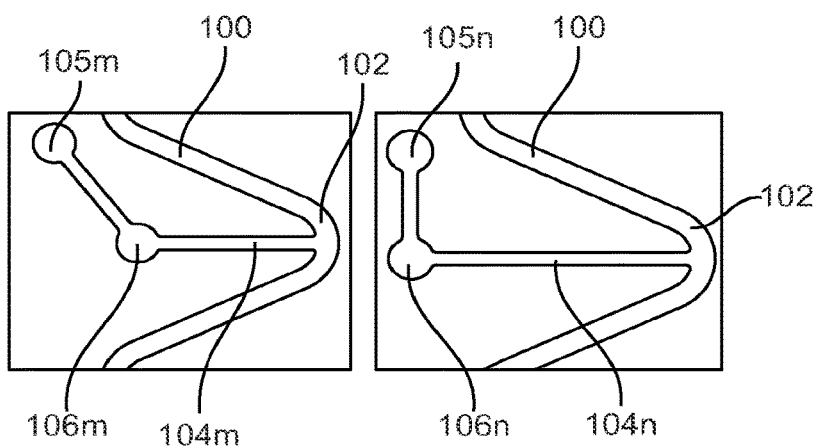

In other examples, supporting elements may have bends, bifurcations, multiple contact pads, and their structural features to enhance their ability to support the expandable membranes in regions between adjacent struts and/or adjacent support rings. As shown in FIG. 7K, supporting element 104k is bifurcated into a Y-shape and has a pair of contact pads 105k. Supporting element 104l shown in FIG. 7L also has a bifurcation with a pair of contact pads 105l and third contact pad 106l located at the point of bifurcation.

In still other examples, supporting elements may be formed as linked, linear segments optionally having contact pads at some or all junctions between the links. For example, as shown in FIGS. 7M and 7N, supporting elements 104m and 104n, respectively, each comprise a pair of linear segments with a contact pad 105m and 105n, respectively, at a terminal free end and an inner contact pad 106m and 106n, respectively, at the junction between the segments. The linear segments in supporting element 104m are attached at an approximately 120° angle while the linear segments in supporting element 104n are attached at a right (90°) angle.

Figure 7O:
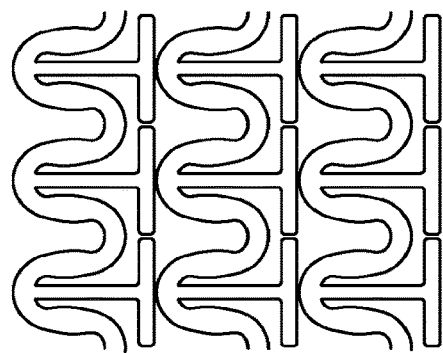
Figure 7P:
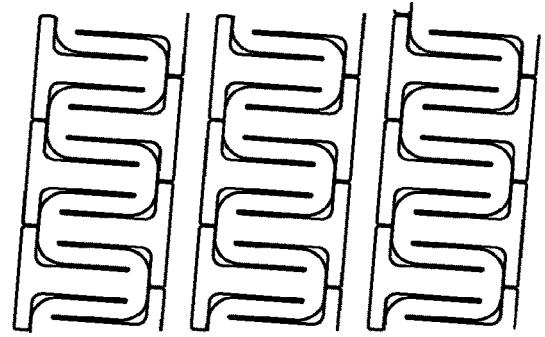
Figure 7Q:
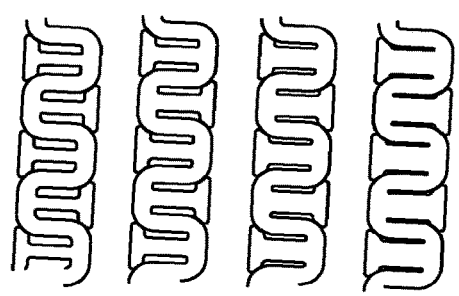
Figure 7R:
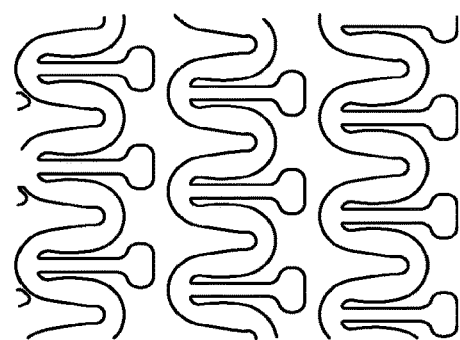

Referring now to FIGS. 7O to 7R, a variety of T-shaped supporting elements having base ends attached to an inner surface of a U-shaped crown are illustrated. The T-ends may extend into a gap between adjacent rings and may be flush with either ring as shown in FIGS. 7O and 7P. Alternatively, the T-ends may be flush with the ring to which they are attached (FIG. 7Q) or may extend into the intermediate gap without contacting either ring (FIG. 7R). In some examples, supporting elements within each ring extend in the same direction as shown in FIG. 7O. Alternatively, supporting elements within each ring may extend in opposite directions as shown in FIG. 7P.

Figure 7S:
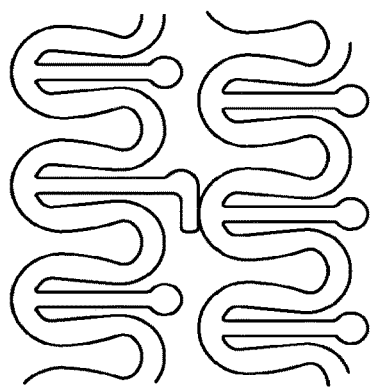

Referring now to FIG. 7S, supporting elements having base ends attached to an inner surface of a U-shaped crown may have unattached ends having different terminal geometries extending into a gap between adjacent rings. For example, some of the terminal ends may be provided with a bumper or stop element configured to engage an adjacent ring to maintain a desired gap region therebetween.

Figure 7T:
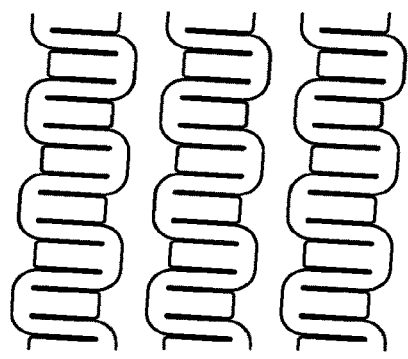
Figure 7U:
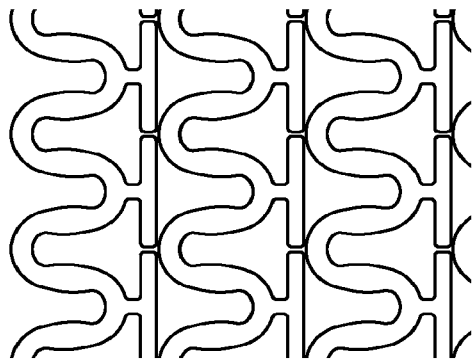

Referring now to FIG. 7T, supporting elements having base ends attached to an inner surface of a Box-shaped, or U-shaped crown may have recessed unattached ends (free ends) which fill essentially all space between adjacent struts on each ring (or which fills or covers substantially all the space between adjacent struts on each ring in the as patterned or as delivered configuration). This is a preferred ring geometry as shown in more detail in FIGS. 11A to 11D discussed in detail below.

Figure 7V:
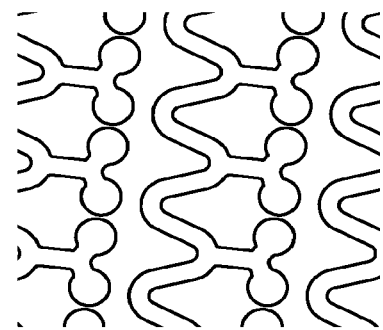
Figure 7W:
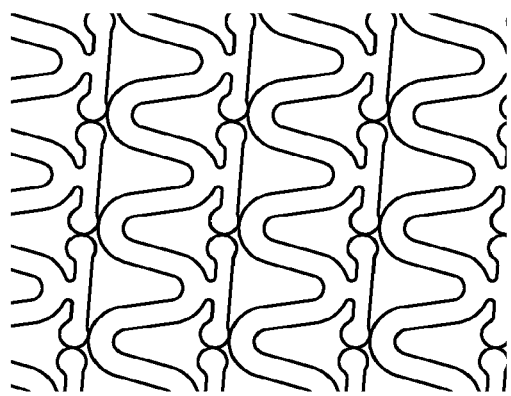
Figure 7X:
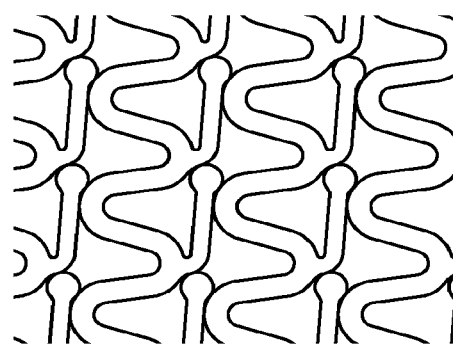
Figure 7Y:
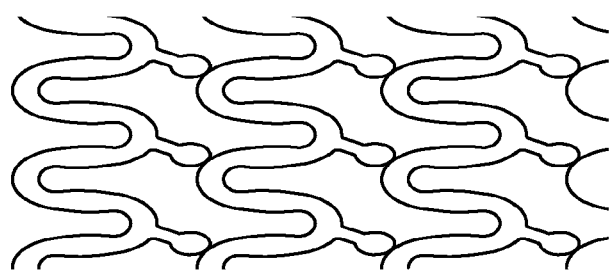

Referring now to FIGS. 7U to 7Y and 7P, a variety of supporting elements having base ends attached to an outer surface of a U-shaped crown are illustrated. The unattached ends (free ends) of the supporting elements may have T-shaped, L-shaped, deflected, or a variety of other geometries, and will fully or partially extend into a gap between adjacent ring elements. the terminal ends may be flush with an adjacent ring, as shown in FIGS. 7O, 7U, 7W, 7X, and 7Y, or may leave an intermediate gap without contacting adjacent ring (FIG. 7V).

Figure 7Z:
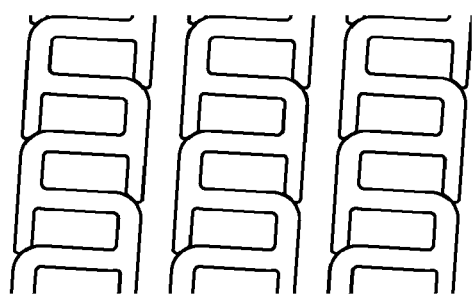
Figure 7A:
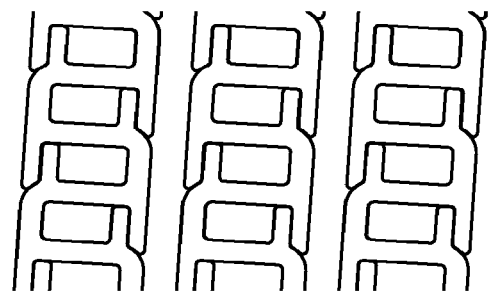
Figure 7A:
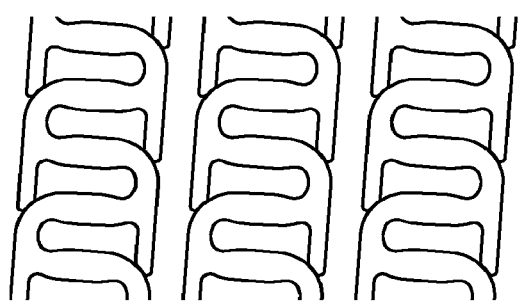
Figure 7A:
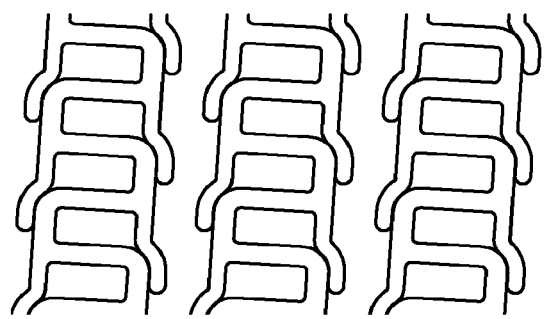
Figure 7A:
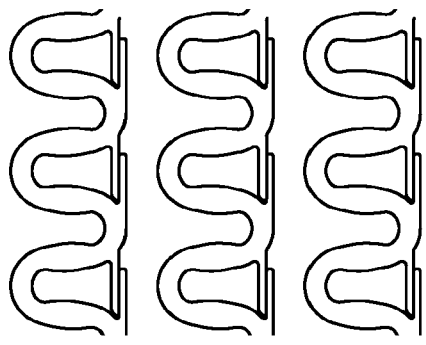
Figure 7A:
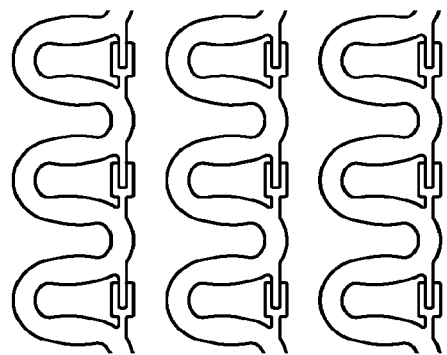
Figure 7A:
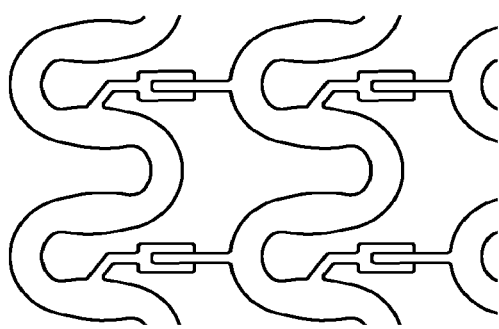
Figure 7A:
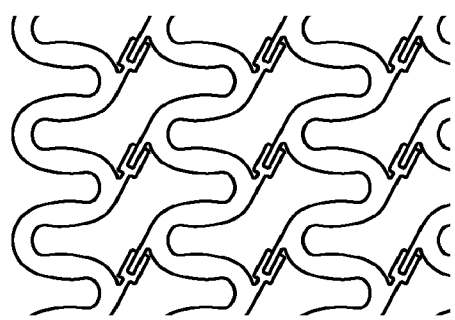
Figure 7A:
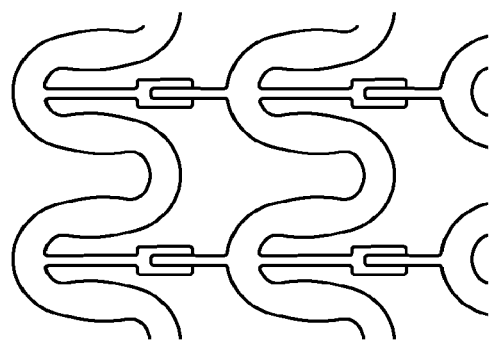
Figure 7A:
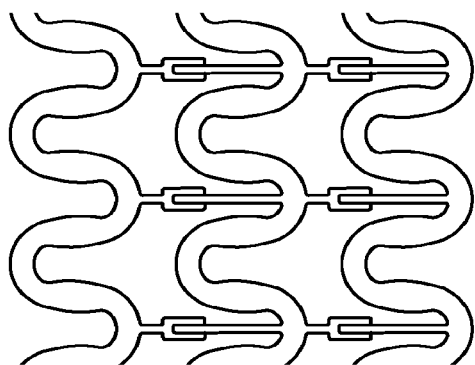
Figure 7A:
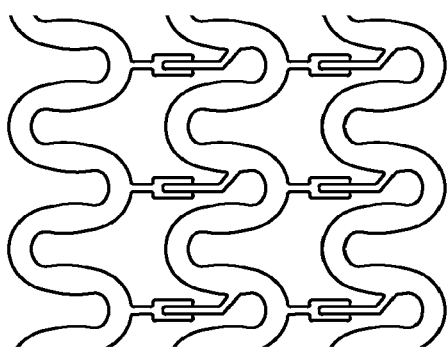
Figure 7A:
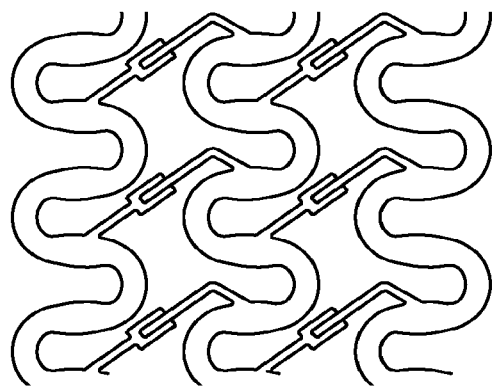
Figure 7A:
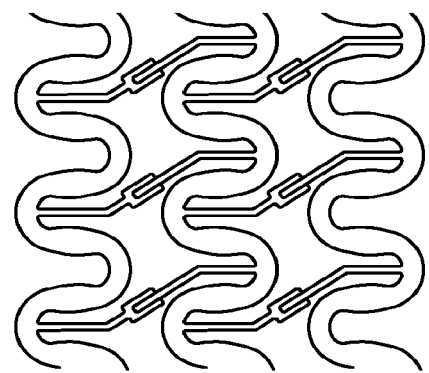
Figure 7A:
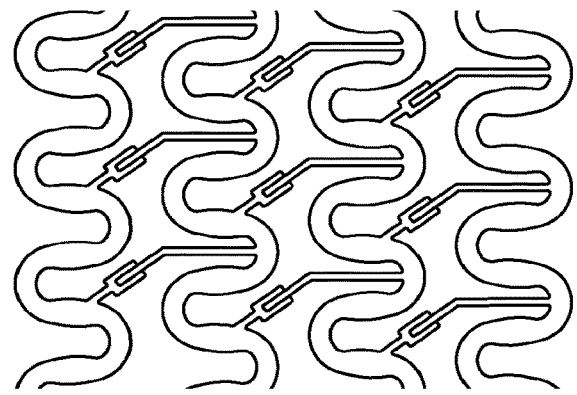
Figure 7A:
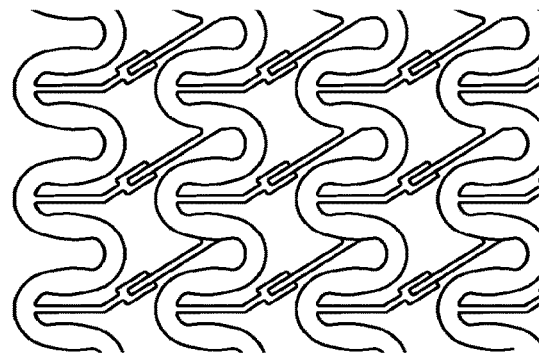
Figure 7A:
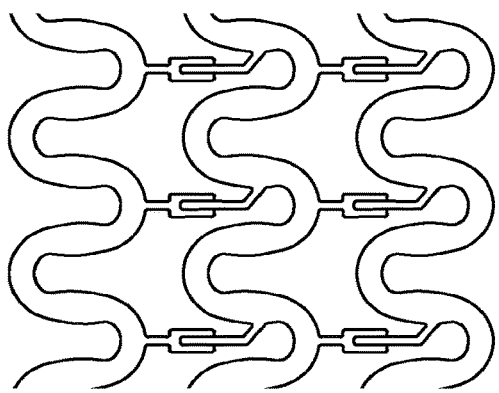
Figure 7A:
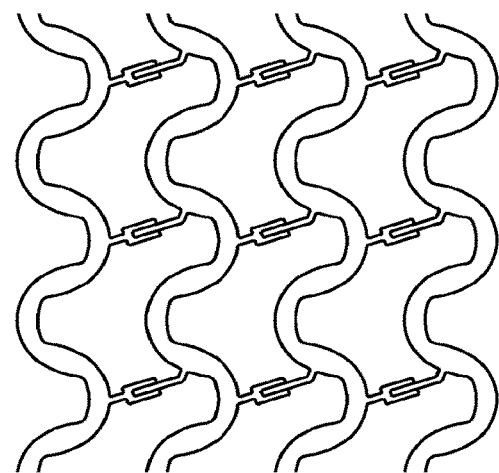
Figure 7A:
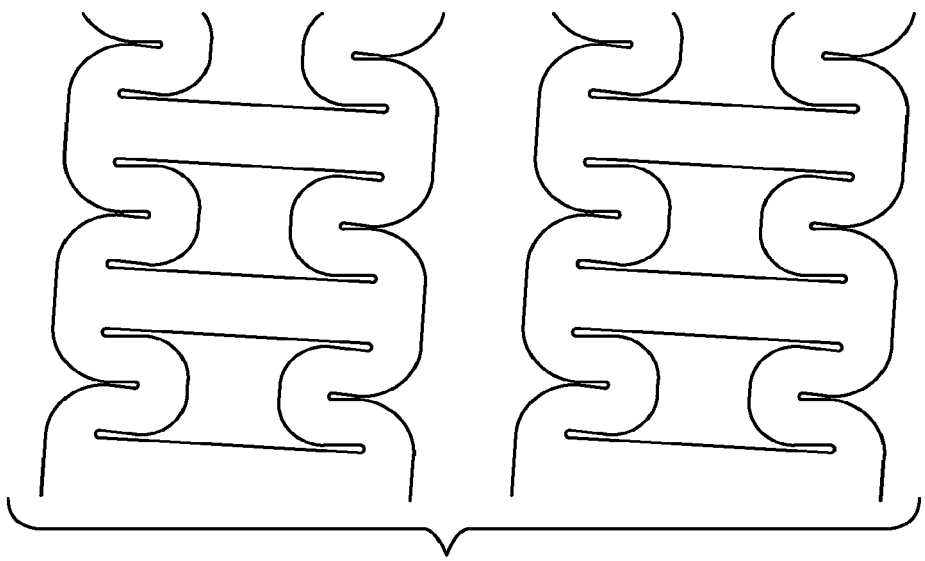
Figure 7A:
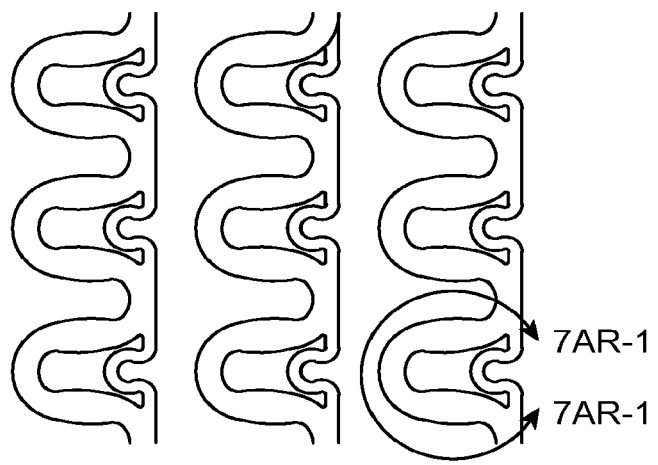
Figure 7A:
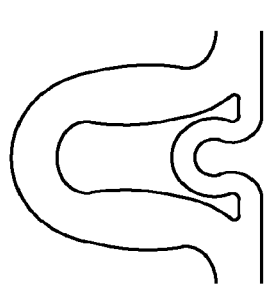
Figure 7A:
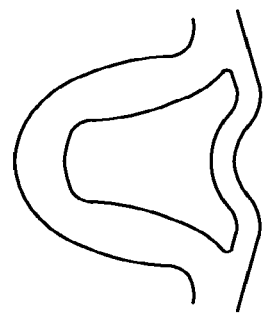

Referring now to FIGS. 7Z to 7AD, a variety of supporting elements may be attached to a side of a crown and extend circumferentially toward and adjacent crown. Single lateral supporting elements are shown in FIGS. 7Z, 7AB, and 7AC, while a pairs of sliding lateral elements are shown in FIGS. 7AA and 7AD. The lateral elements may optionally extend over the outer surface of an adjacent crown, as shown in FIG. 7AC.

As shown in FIGS. 7AE to 7AP, the supporting elements may be formed as "lock and key" structures comprising a straight or male element which is slightly received in a slotted or "clevis" member. Such supporting elements can accommodate circumferential movement and/or axial movement of adjacent ring elements as the scaffold is radially expanded. such expandable or accommodating supporting elements may extend across and opening of a U-shaped cell (including a pair of struts joined by a crown), as shown in FIGS. 7AD and 7AE, or may extend from one ring to an adjacent ring as shown in FIGS. 7AF to 7AP. The base end of the male element and/or clevis element may be attached to an inner or outer surface of a crown, to an inner surface of a strut, and may extend in a circumferential direction or may be inclined at an angle relative to the circumference. Either or both of the male elements and slash or the clevis element may have one or more bends. Various geometries and combinations are shown in FIGS. 7AE to 7AP, but it should be appreciated that many other specific geometries could be utilized.

In some instances, a supporting element may be formed between a pair of adjacent circumferential elements to form a single radially expandable ring, as shown in FIG. 7AQ. Such a "double" ring structure may be formed helically, as separate parallel rings, or in any of the other configurations as shown herein.

Referring now to FIGS. 7AR, 7AR-1, and 7AR-2, a particular serpentine ring arrangement comprises U-shaped cells with U-shaped supporting elements extending across the opening between adjacent crowns. The U-shaped supporting elements are configured to expand from a crimped configuration, as shown in FIG. 7AR-1 to an expanded configuration as shown in FIG. 7AR-2 as the ring is radially expanded.

Figure 8:
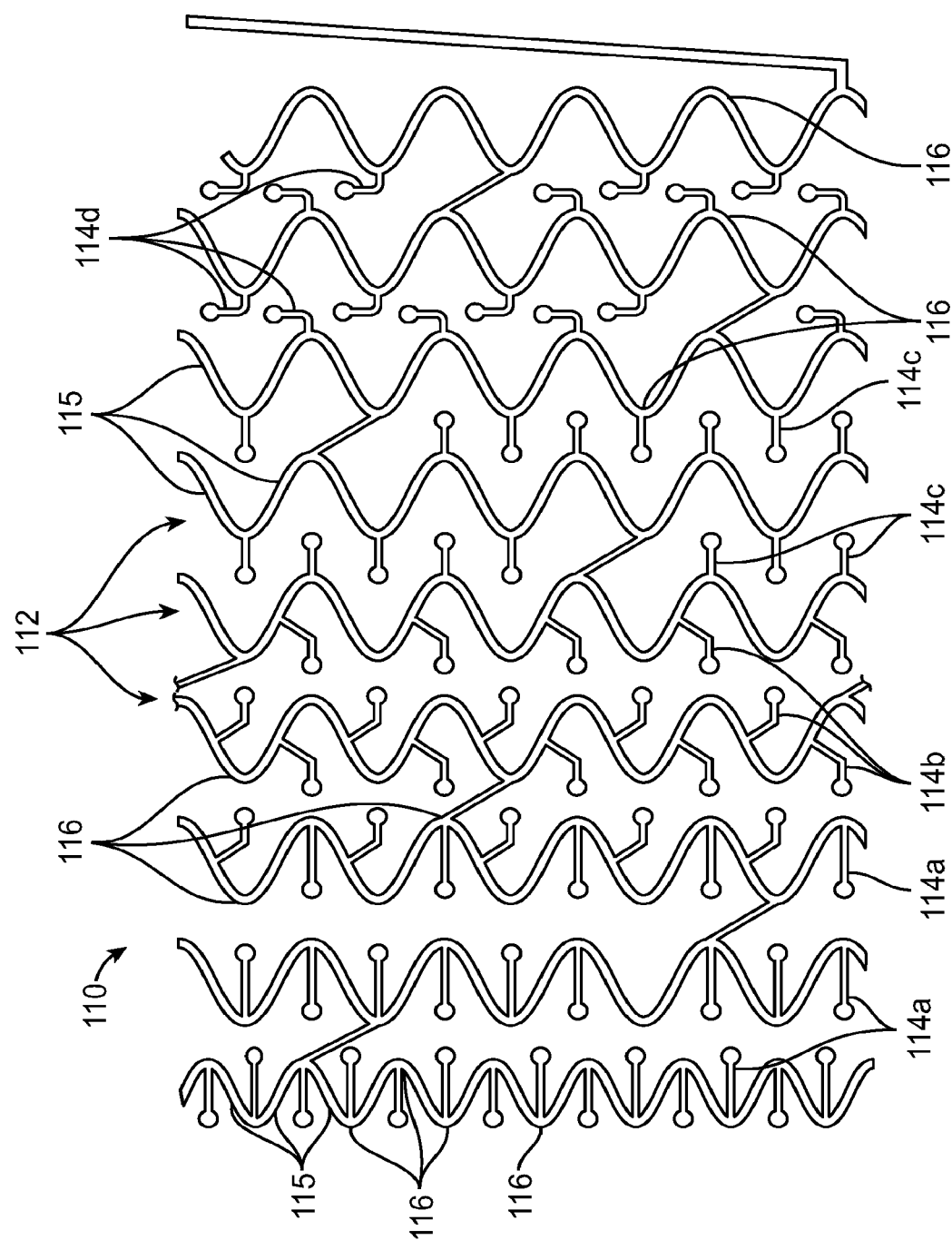
FIG. 8 is a "rolled out" view of a further example of a supporting scaffold having adjacently linked circumferential supporting rings with differing frequency of number of crowns, gap widths, cells periods, cells amplitudes and differently configured examples of supporting elements constructed in accordance with the principles of the present invention.

FIG. 8 is a "rolled out" view of a further example of a supporting scaffold 110 having adjacently linked radially expandable circumferential supporting rings 112 having differing widths and differently configured supporting elements 114 constructed in accordance with the principles of the present invention. As with previous examples, the supporting rings 112 are constructed with pairs of struts 115 joined by crowns 116. Supporting elements 114a are linear beams similar to supporting elements 52 described with reference to FIGS. 2A-2D. Supporting elements 114b have a single bend and are similar to supporting elements 104m shown in FIG. 7M but lacking a middle contact pad between adjacent linear segments and attached to a strut 115 rather than a crown 116. Supporting elements 114c are short, straight beams having a distal contact pad. Supporting elements 114d have a single bend are similar to supporting elements 104h in FIG. 7H. The scaffold rings as shown can have differing number of crowns on adjacent rings, differing cells periods on adjacent rings, supporting elements having differing shapes, number, and frequency on adjacent rings, differing gaps between rings, and/or differing rings amplitudes.

Figure 9A:
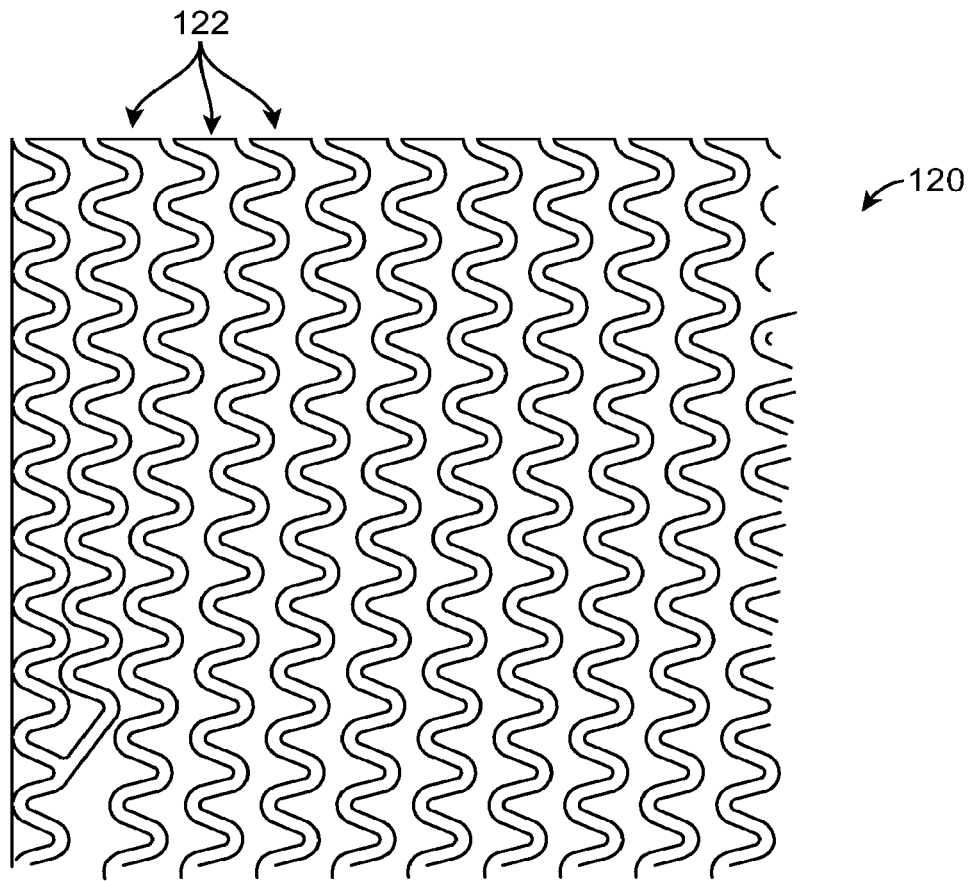
FIG. 9A is a "rolled out" view of an alternative example of a supporting scaffold having helically arranged circumferential supporting rings free from supporting elements constructed in accordance with the principles of the present invention.
Figure 9B:
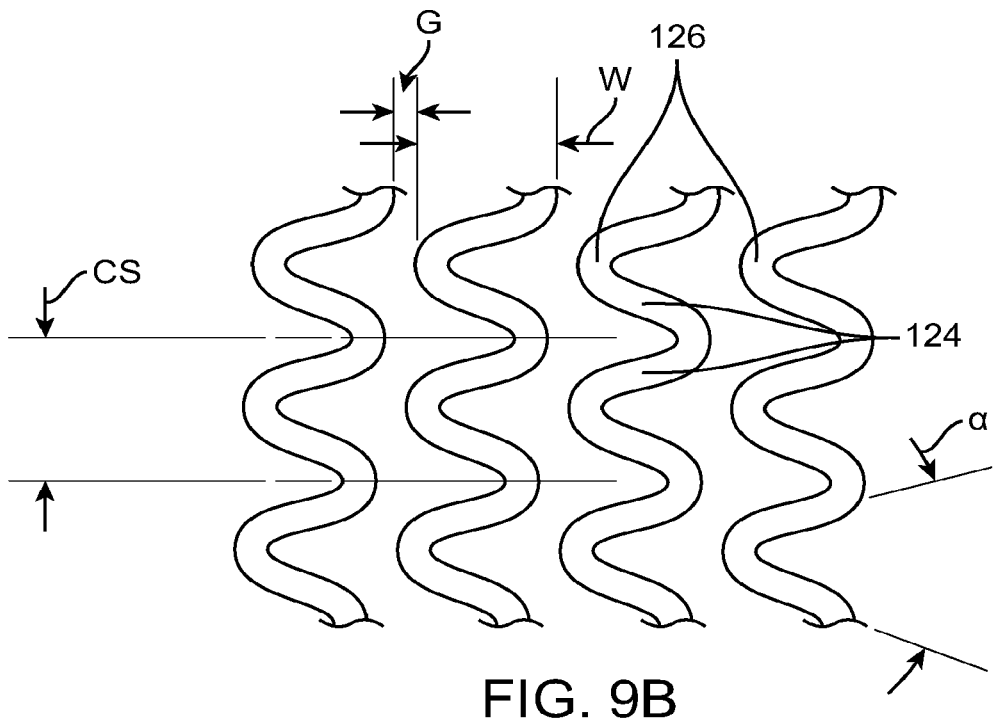
FIG. 9B is a detailed view of adjacent circumferential supporting rings of the expandable distal tip of the supporting scaffold of FIG. 9A.

As shown in FIGS. 9A and 9B, a supporting scaffold 120 comprises a plurality of radially expandable circumferential supporting rings 122 comprising struts 124 and crowns 126. Unlike previous examples, there are no supporting elements attached to the supporting rings 122. Instead, the supporting rings 122 have a pattern which inherently provides enhanced support to an attached expandable membrane when used in an expandable distal tip of an aspiration catheter. More specifically, the supporting rings comprise serpentine or zig-zag rings having a width W in a range from 0.1 mm to 1 mm, preferably from 0.3 mm to 0.4 mm; a gap G between adjacent rings in a range from 0 mm to 1 mm, preferably from 0.05 mm to 0.4 mm; crowns arranged along axial lines separated by a spacing CS in a range from 0.1 mm to 1 mm, preferably from 0.25 mm to 0.4 mm; and struts diverging from the crowns at an angle α in a range from 0° to 90°, preferably from 20° to 40°, prior to expansion.

Figure 9C:
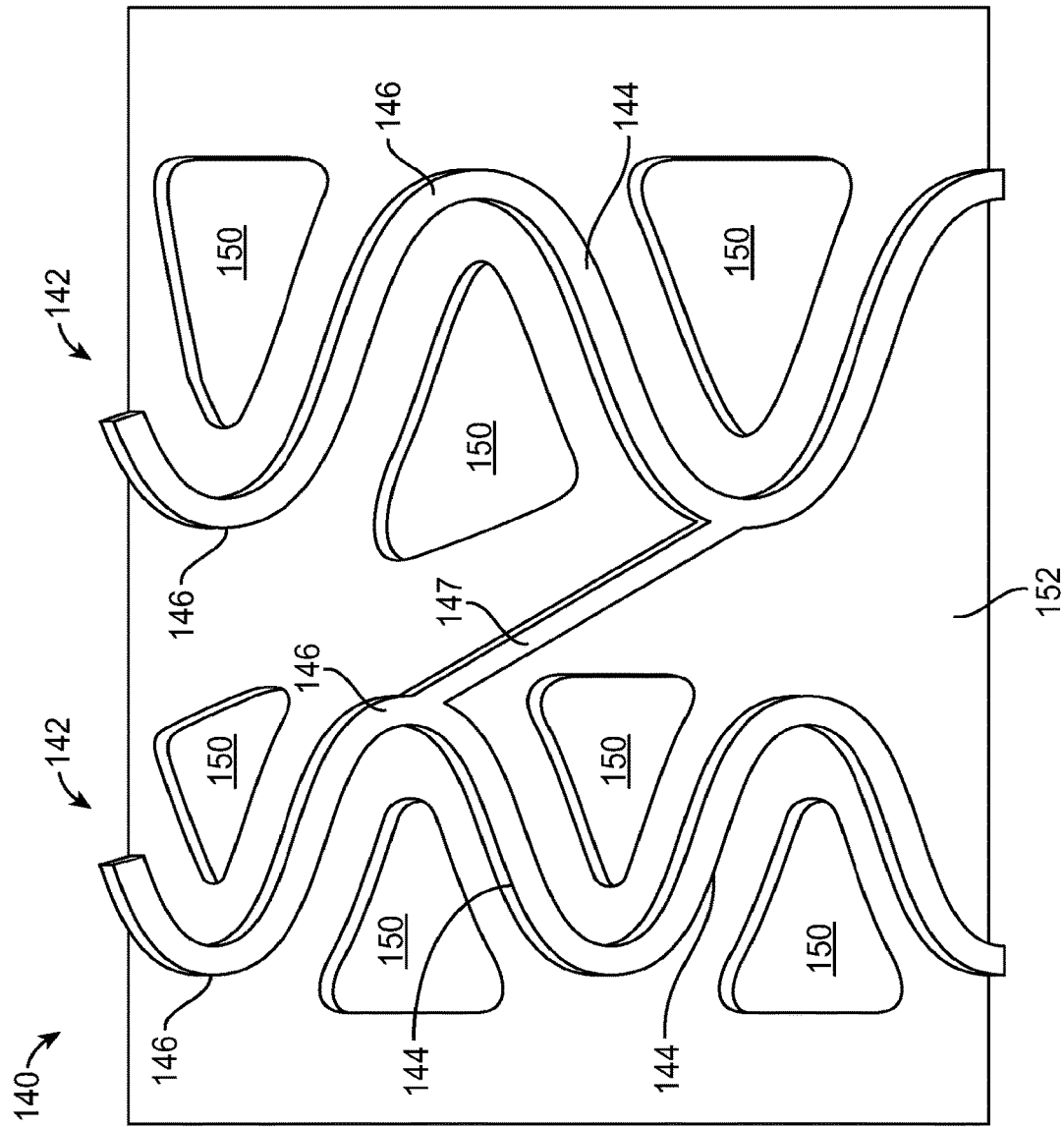
FIG. 9C illustrates an alternative example of the supporting scaffold of the present invention having discrete supporting pads (or islands) located between struts of a serpentine supporting ring.

FIG. 9C illustrates a further alternative embodiment of the supporting scaffold 140 of the present invention having discrete supporting pads 150 located between struts 144 of a serpentine radially expandable supporting ring 142. The struts 144 are joined by crowns 146 in a conventional manner, and adjacent supporting rings 142 are joined by links 147. The supporting pads 150 are attached to the supporting the membrane 152 in V-shaped regions between adjacent struts 144 but are otherwise not attached to the remaining components of the expandable supporting structure 140. Preferably though not necessarily the supporting pads 150 may have a triangular shape corresponding to the V-shaped region in which they are attached. They may also have other shapes such as circular, oval, or other rounded shapes.

Figure 10A:
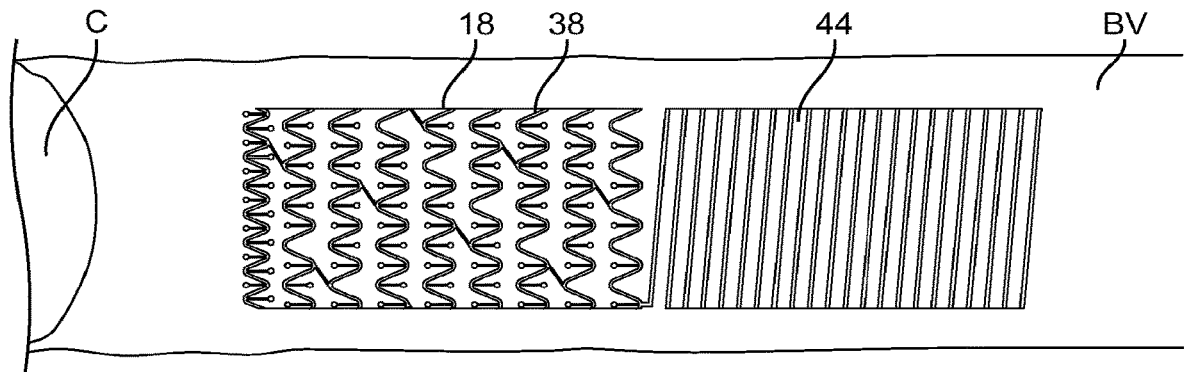
FIGS. 10A-10G illustrate an exemplary use of the system of FIG. 1 for advancing and expanding (deploying) an aspiration catheter in a patient's vasculature accordance with the principles of the present invention.
Figure 10B:
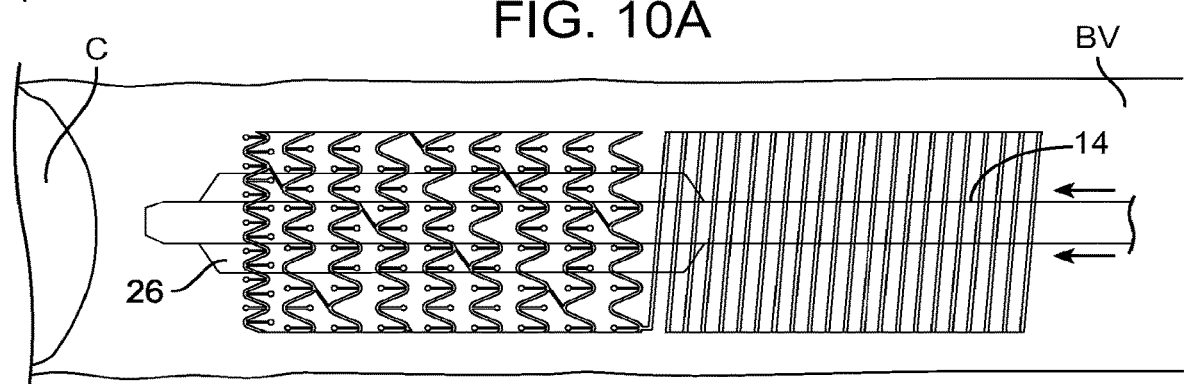
Figure 10C:
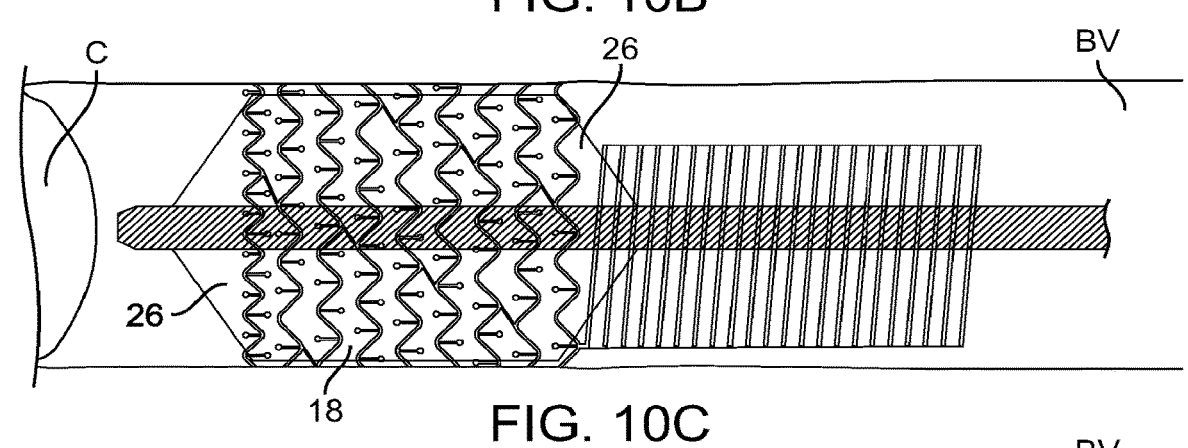
Figure 10D:
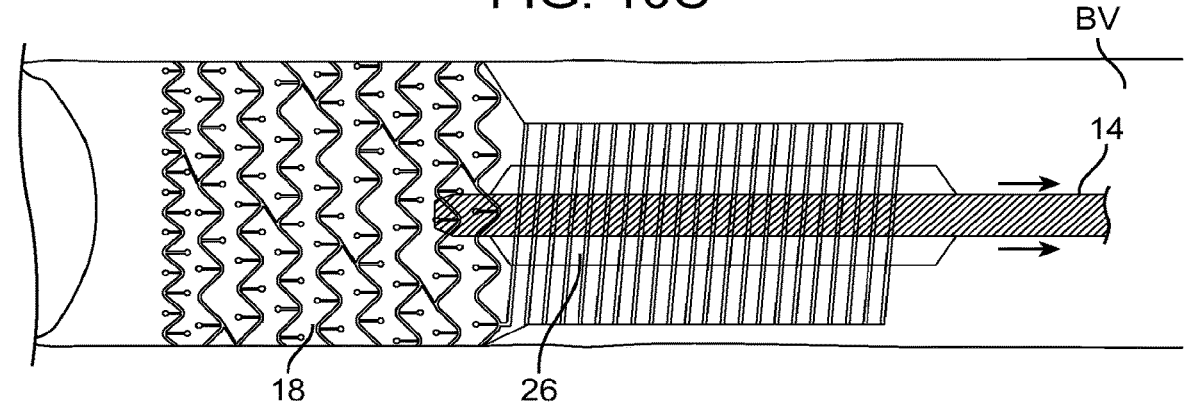
Figure 10E:
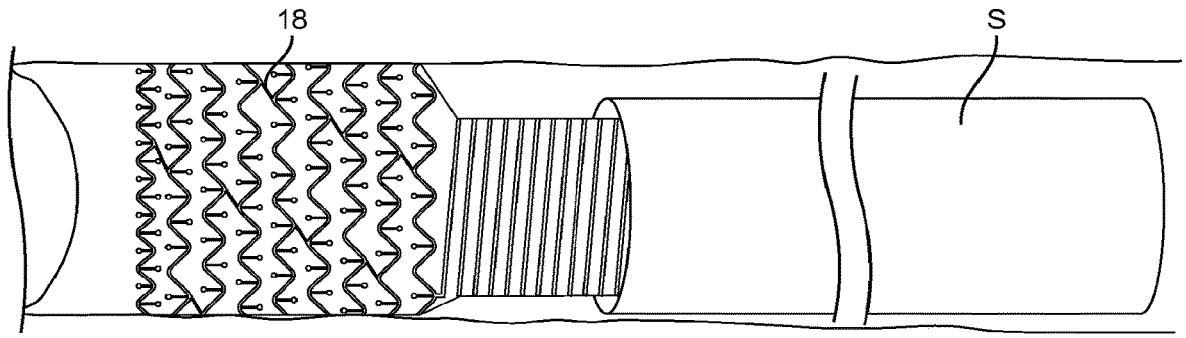
Figure 10F:
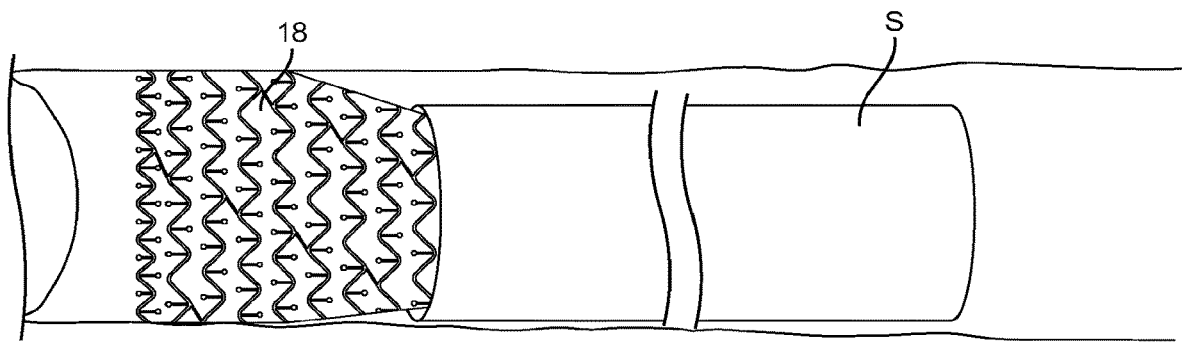
Figure 10G:
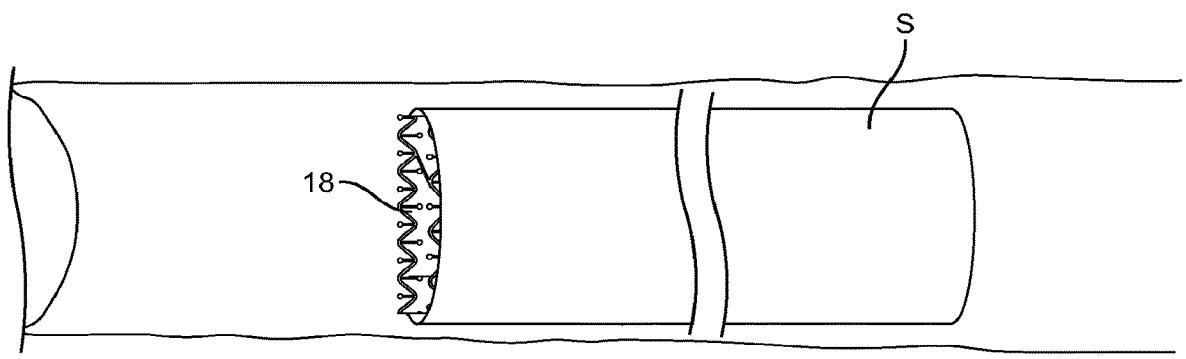

Referring now to FIGS. 10A to 10G, delivery of an aspiration catheter to a patient's vasculature in accordance with the principles of the present invention will be described. An aspiration catheter, such as aspiration catheter 12 shown in FIG. 1, is advanced to a region of clot C in the patient's blood vessel BV, typically a cerebral blood vessel, as shown in FIG. 10A. For convenience, only the expandable distal tip 18 of aspiration catheter 12 is illustrated. As shown in FIGS. 10B and 10C, the balloon 26 of the distal expansion catheter 14 is inflated to expand the expandable distal tip 18 of the catheter against the blood vessel wall. In some instances, the aspiration catheter 12 is first introduced to the blood vessel BV over a guidewire, and a distal tip expansion catheter 14 introduced after the aspiration catheter has been positioned. In other instances, the aspiration catheter 12 and the distal tip expansion catheter 14 together or in tandem. After the distal tip 18 of the aspiration catheter 12 has been expanded, the distal tip expansion catheter 14 will be withdrawn, as shown in FIG. 10D. After the clot has been aspirated, the aspiration catheter 12 be withdrawn through a sheath S (or a guiding catheter), as shown in FIG. 10E, causing the expanded distal tip 18 to be constricted (contracted) for removal as shown in FIGS. 10F and 10G. Alternatively (not shown), the aspiration catheter may be withdrawn until the expandable tip proximal end reaches the distal end of the sheath, and then both the sheath and aspiration catheter are removed together as one unit.

Referring now to FIGS. 11A to 11D, an alternative construction of expandable distal tip 18 of the aspiration catheter 12 will be described. The alternative expandable distal tip 218 of aspiration catheter 12 includes both a supporting scaffold 238 and an expandable membrane 240. As described previously, the expandable membrane 240 will typically comprise an elastic or inelastic (stretchable) polymeric membrane having the supporting scaffold 238 embedded or laminated therein. The supporting scaffold 238 will comprise a metal or metal alloy scaffold configured for balloon expansion, typically comprising a malleable metal as described elsewhere herein.

The supporting scaffold 238 includes a plurality of radially expandable circumferential supporting rings 242. The rings 242 comprise U-shaped or other shaped bend structures or cells structures including struts 248 joined by crowns 250 where adjacent rings 242 are connected in an end-to-end in a helical pattern.

The supporting elements 252 are each located between adjacent pairs of struts 248 and have a base end 256 attached to an inner radius of the crown 250. Unattached ends 258 (free ends) of each supporting element 252 are recessed in the space between adjacent struts 248 but otherwise occupy most or all of the space between adjacent struts prior to ring expansion.

Figure 11D:
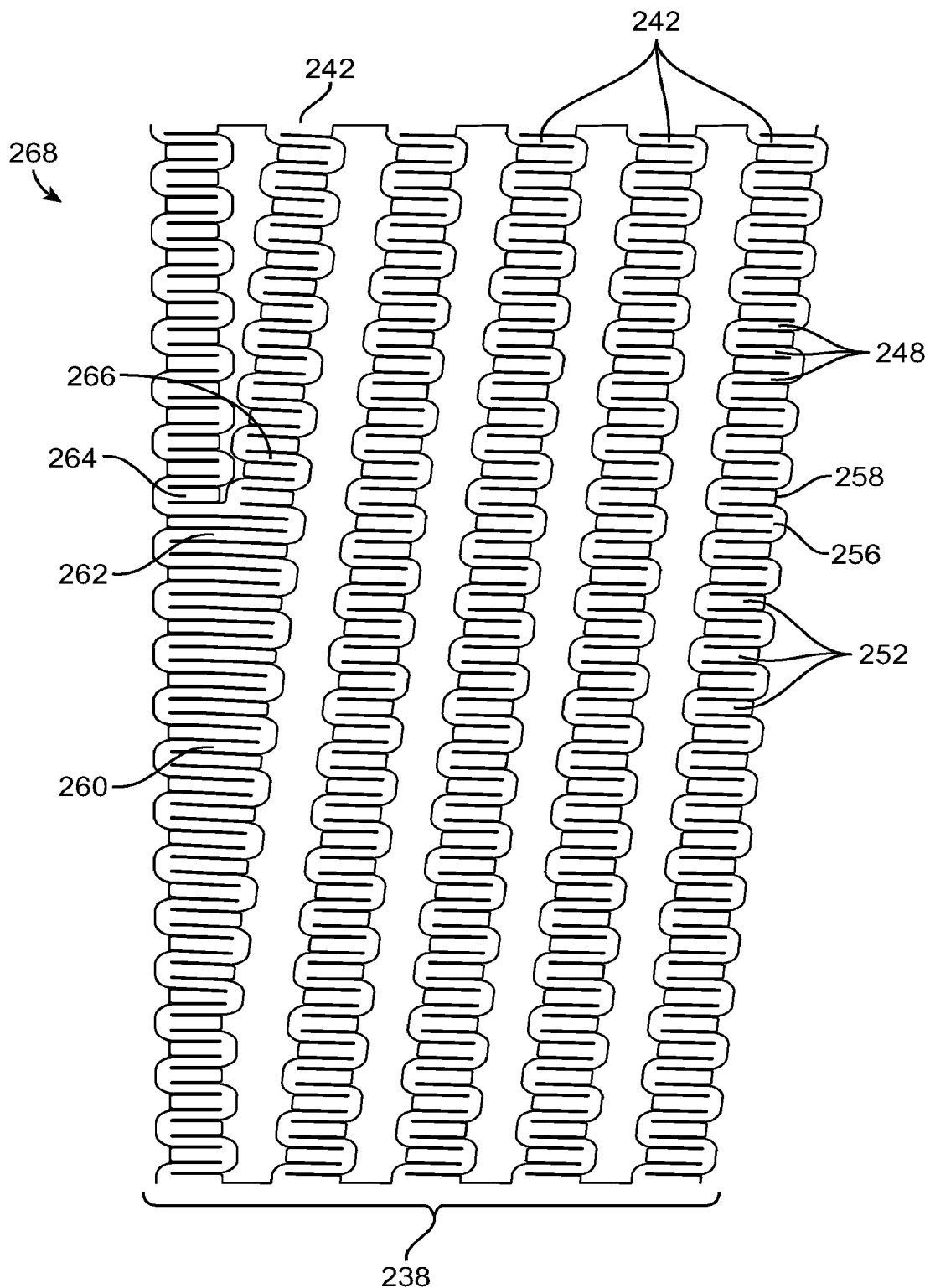
FIG. 11D is an enlarged "rolled out" view of the supporting scaffold of the expandable distal tip of the aspiration catheter of the system of FIG. 11A showing details of a flush distal termination ring.

Typically, but not necessarily, the supporting scaffolds 238 will be laser cut from metal alloy tubes, for example, in the "rolled out" pattern shown in FIGS. 11B and 11D. That pattern includes a coil support (reinforcement) region 244 which is intended to support at least a proximal portion of the tubular body 222, as best seen in FIG. 11A. A short axial link 246 may be provided at the transition between the supporting scaffold 238 and the coil support region 244 to provide stress relief between the highly flexible distal tip and the less flexible catheter shaft. The coil support 244 may have a length sufficient to extend the entire length of the tubular body 222 but will more typically extend over only a shorter transition region at a distal end of the tubular body. Proximal portions of the tubular body 222 may have braided or other forms of reinforcement as shown in FIG. 1A.

As the shown in FIGS. 11A to 11D, the expandable distal tip 218 and the supporting scaffold 238 of the aspiration catheter 212 are in their non-expanded configurations which are suitable for introduction through the patient's vasculature to a target clot location. Once at the target clot location, however, the expandable distal tip 218 and supporting structure 238 will be balloon-expanded to engage a clot or a wall of the blood vessel adjacent to clot, as described in more detail with reference to FIGS. 13A-13G hereinbelow. As shown in FIG. 11B, the proximal end of the expandable scaffold comprises both expandable segments and non-expandable segments on the proximal end ring and is attached in at least one location to adjacent coil (as shown). Alternatively, the terminal end may be attached to an adjacent expandable ring and/or adjacent non expandable coil in one or more locations by a link and/or attaching pointes on adjacent rings or turns. Alternatively, the proximal end ring of the expandable scaffold may be configured to be substantially non expandable, a segment expandable and a segment that is non expandable on the same ring or is configured to be expandable fully and is separately attached to a structure proximally that is not expandable.

As best seen in FIG. 11D, a distal end of supporting scaffold 238 includes a terminal ring 260 having an enlarged end 262 (enlarged amplitude) and a tapered end 264. The enlarged end 262 is attached to a distal terminus 266 of a final helical turn of these scaffold 238. The enlarged end 262 is also attached to the tapered end 264 of the terminal ring 260. In this way, a transition is made between the helical orientation of the rings 242 and a "squared" distal face 268 of the supporting scaffold 238. This "squared" construction eliminates having a free distal end of a ring exposed to the vascular lumen as the aspiration catheter is advanced through the vasculature.

Figure 11E:
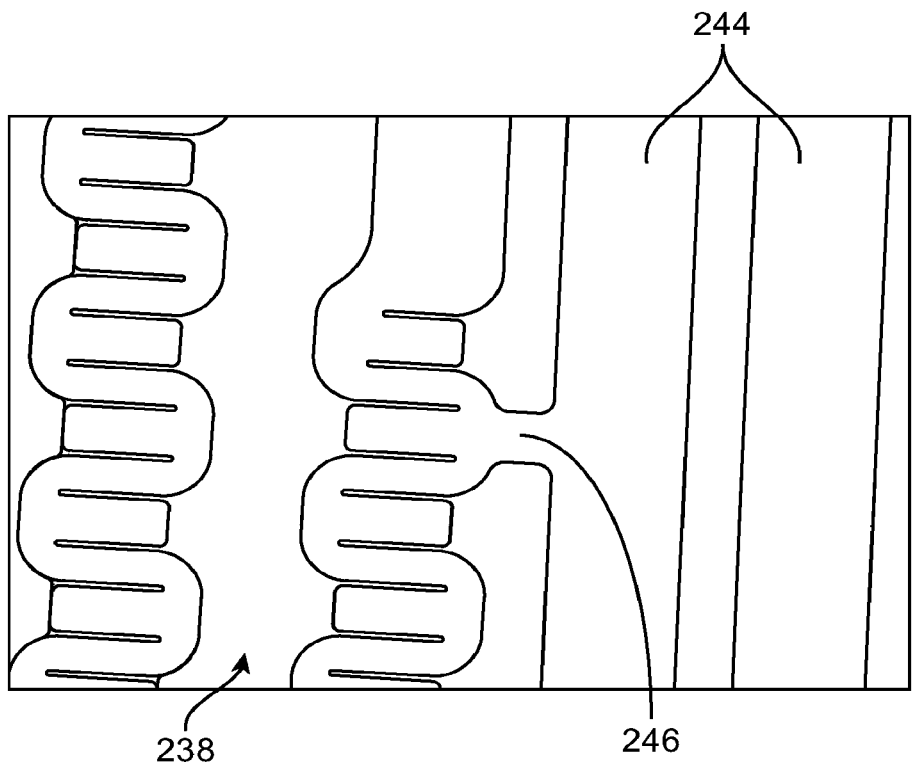
FIGS. 11E and 11F are alternative detailed views examples of a transition region between an expandable scaffold supporting the distal tip of an aspiration catheter of the present invention and a fixed diameter reinforcement structure shaft region the aspiration catheter of the present invention.
Figure 11F:
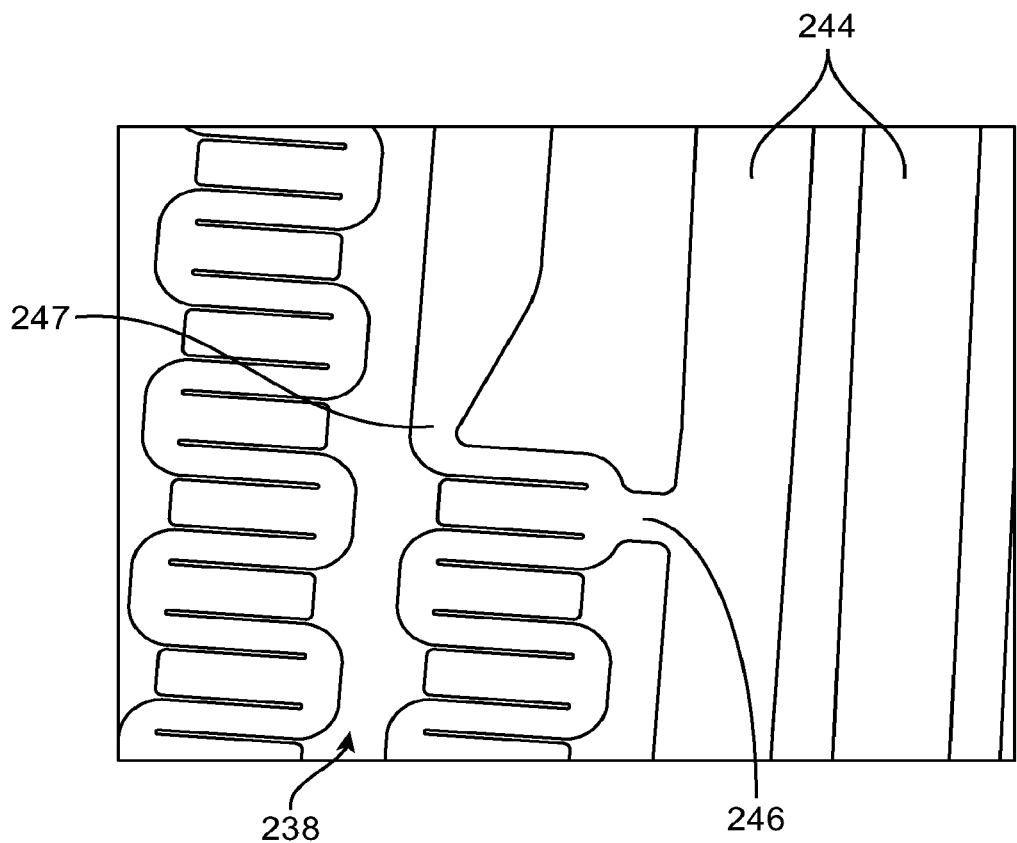

FIGS. 11E and 11F are alternative detailed views of the transition region between the expandable scaffold 238 and the fixed diameter coil support region 244 of the aspiration catheter of the present invention. In both cases, the short axial link 246 provides stress relief between at the transition between the supporting scaffold 238 and the coil support region 244. In FIG. 11F, the connection 247 between the supporting scaffold 238 and the coil support region 244 is thinned to create an inflection point to enhance bending.

Figure 11G:
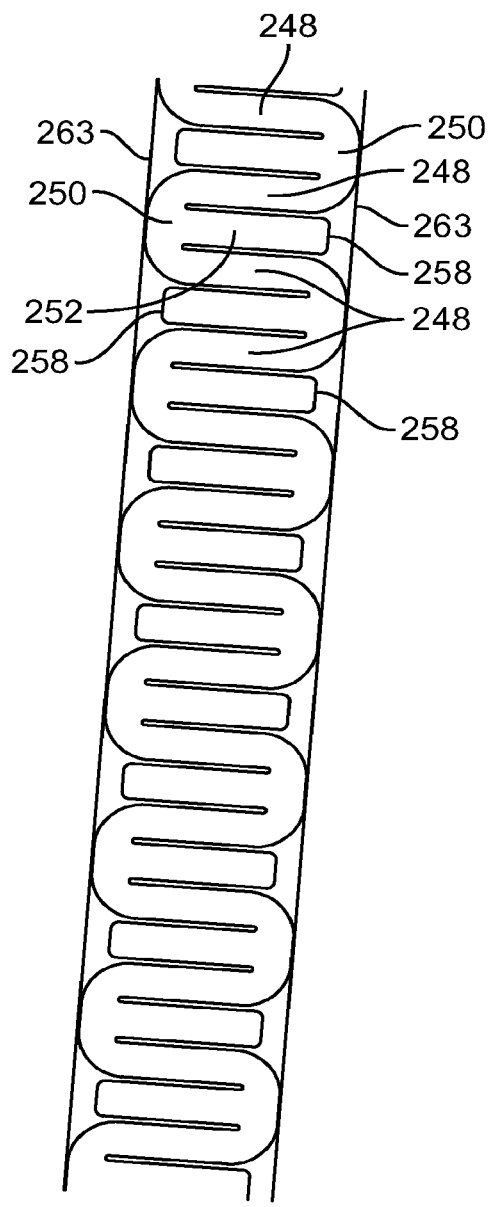
FIGS. 11G and 11H illustrate recessed and protruding cantilevered supporting elements of the present invention.
Figure 11H:
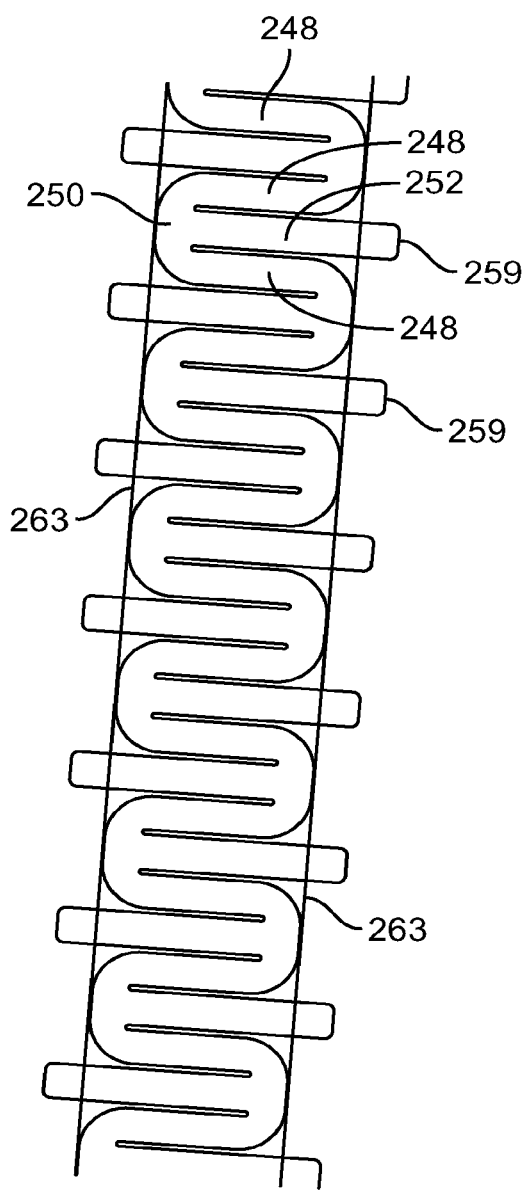

FIG. 11G illustrates a preferred embodiment of the present invention where most or all of the supporting structures 252 remain recessed within an axial width of the ring prior to ring expansion and will emerge further into the gaps after radial expansion of the distal tip. The axial width is defined by the distance between crowns 250 (as shown by lines 263) where the distal tip 258 of each tab-like supporting structure remains between adjacent struts 248 until distal tip expansion, While it is preferred that the supporting elements 252 remain recessed, as shown in FIG. 11H, the distal tips 259 of the cantilevered supporting elements of the present invention may also protrude into the gap regions outside of lines 263, as shown in FIG. 11H. although such construction will generally be less flexible than otherwise similar recessed constructions.

Figure 11I:
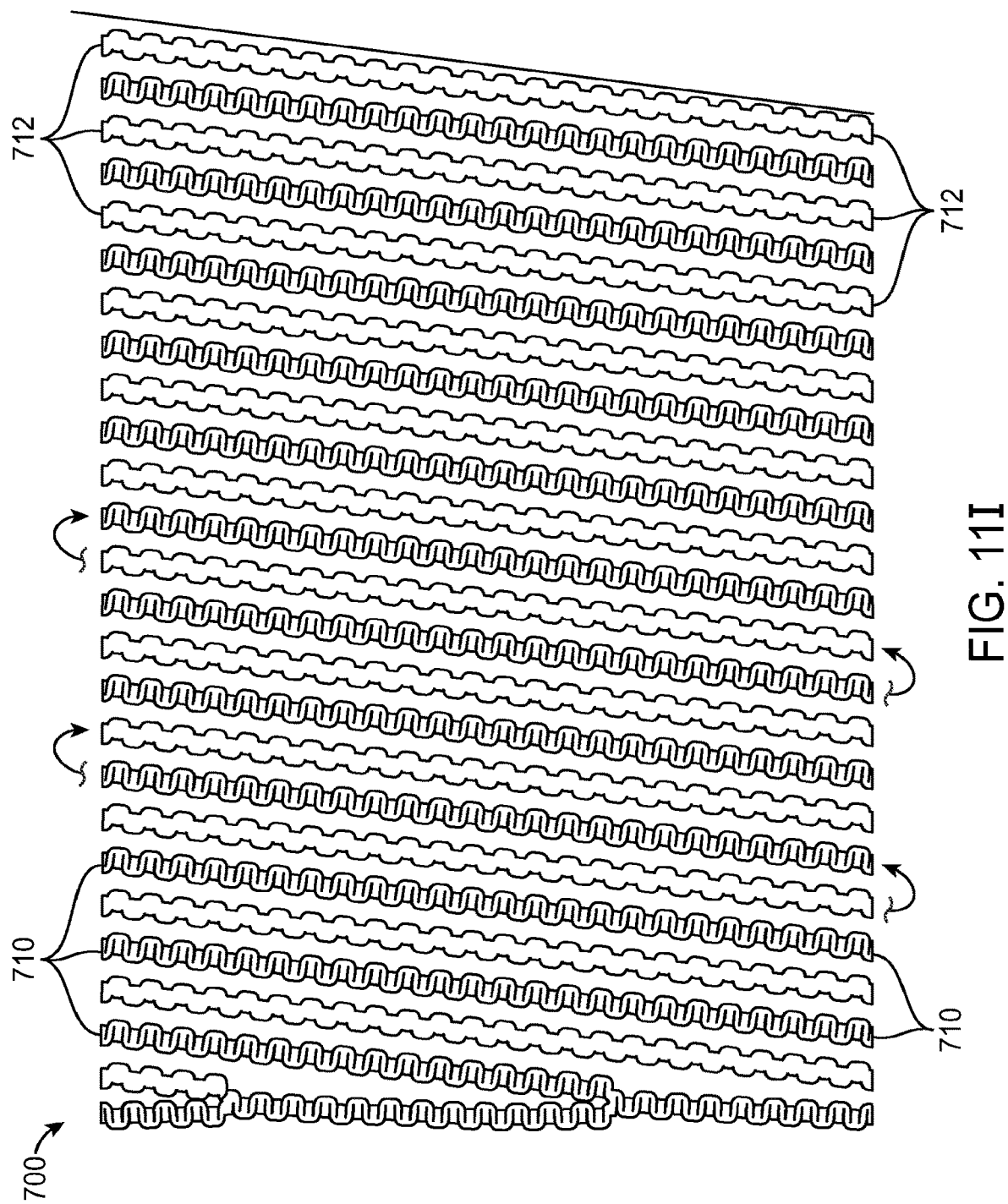
FIGS. 11I and 11J illustrate exemplary helical supporting structures comprising two and three nested continuous helical rings, respectively.
Figure 11J:
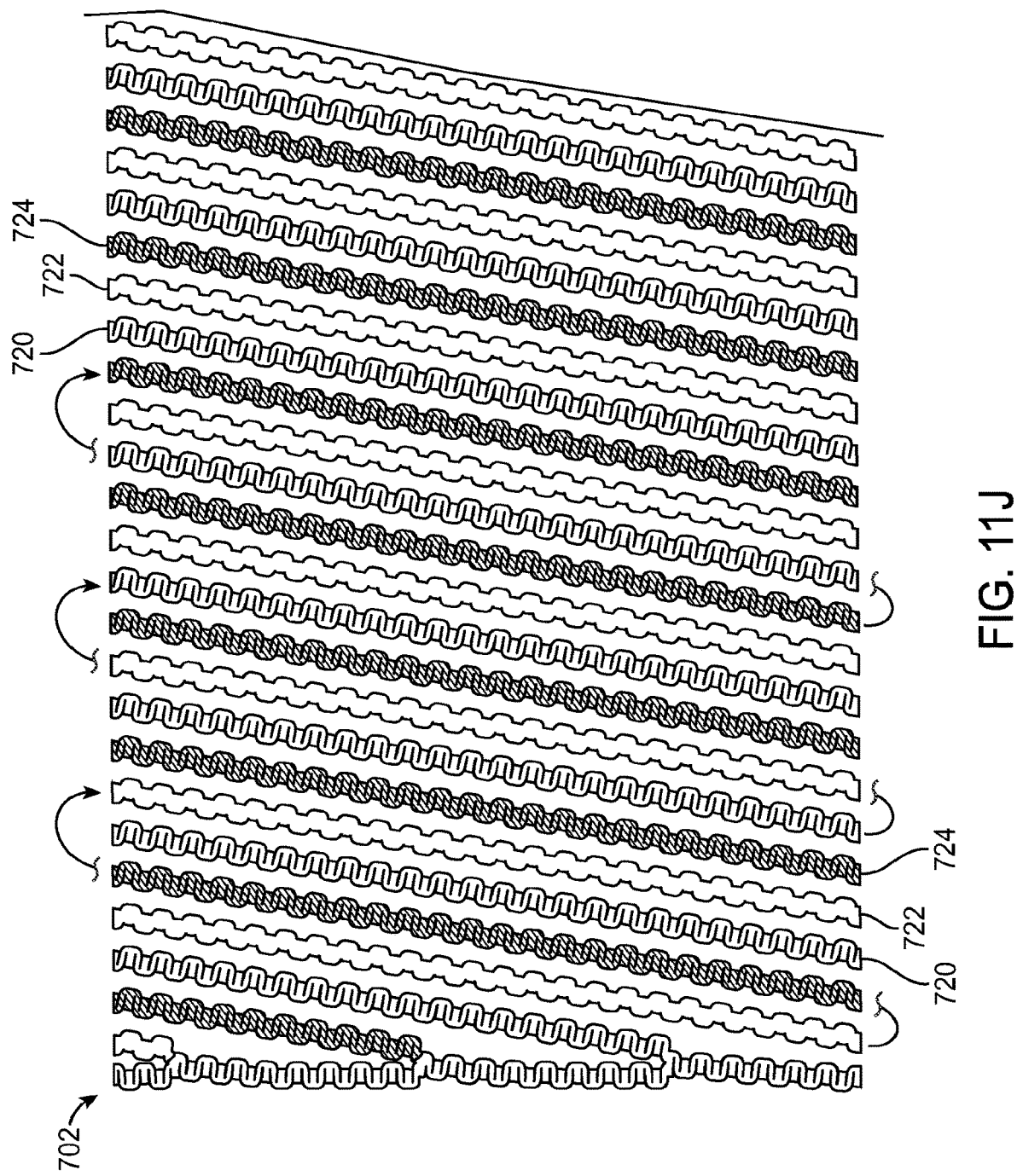

As illustrated thus far in this application, the exemplary helical supporting structures have usually consisted of a single helically wound serpentine, zig-zag or other ribbon having bends that allow for elongation upon radial expansion of the associated ring. In other instances, as illustrated in FIGS. 11I and 11J, supporting structures 700 and 702 may have two, three, four, or more helically nested helical rings. As shown specifically in FIG. 11I, the supporting structure 700 includes first and second helically nested rings 710 and 712, respectively. As shown specifically in FIG. 11J, the supporting structure 702 includes first, second, and third helically nested rings 720, 722, and 724, respectively.

FIGS. 12A to 12D illustrate the supporting scaffold of the expandable distal tip of the aspiration catheter of FIGS. 11A to 11C shown in alternative expanded (deployed) configurations. Expanded distal tip scaffold can have a bell shape 238a (FIG. 12A), a conical shape 238b (FIG. 12B), a pear shape 238c (FIG. 12C), a rounded or arcuate conical shape 238d (FIG. 12D), and many other variations and combinations of shapes that are tapered radially outwardly in a distal direction.

Figure 12A:
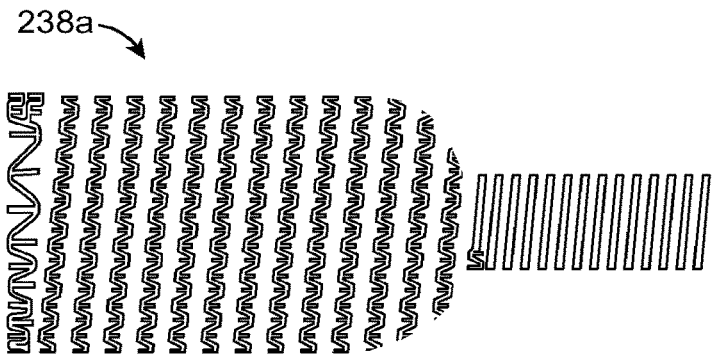
FIGS. 12A to 12D illustrate the supporting scaffold of the expandable distal tip of the aspiration catheter of FIGS. 11A to 11C shown in alternative expanded configurations (deployed).
Figure 12B:
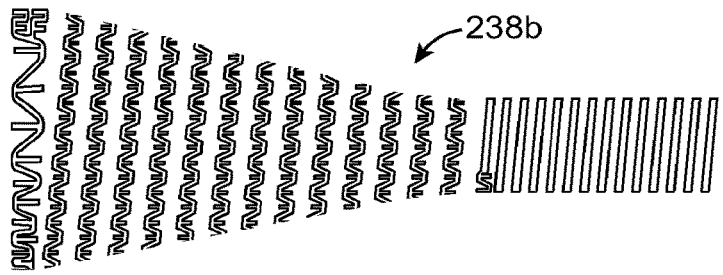
Figure 12C:
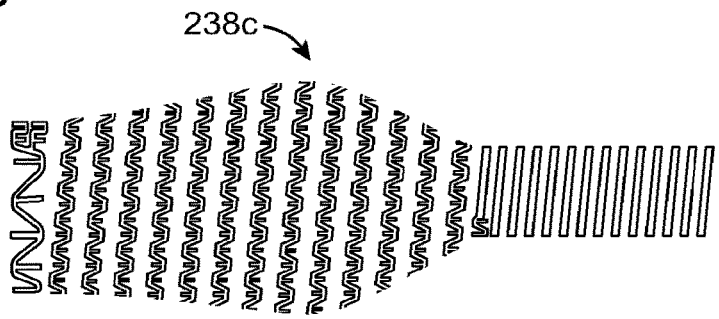
Figure 12D:
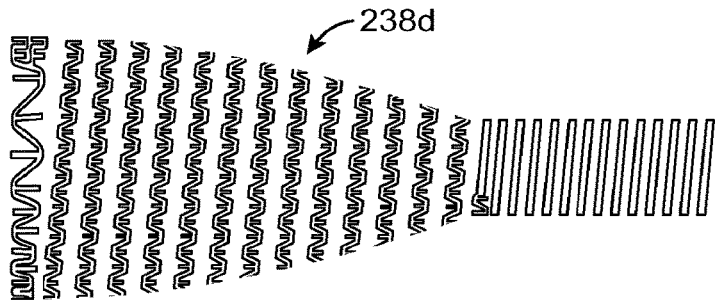
Figure 12E:
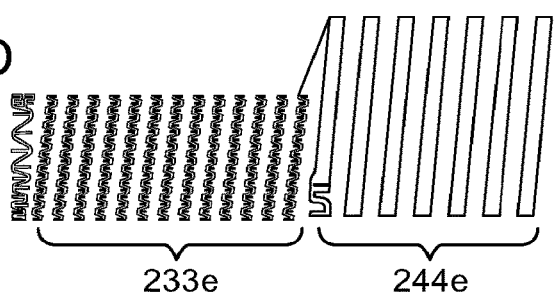
FIG. 12E illustrates a supporting scaffold similar to that shown in FIG. 12A shown in a non-expanded configuration with a reduced diameter tip to facilitate introduction over a guidewire with enhanced deliverability into the vasculature.

FIG. 12E illustrates a supporting scaffold similar to that shown in FIG. 12A shown in a non-expanded configuration with a reduced diameter tip 238e connected to a larger diameter distal shaft end 244e to facilitate introduction over a guidewire.

Figure 13A:
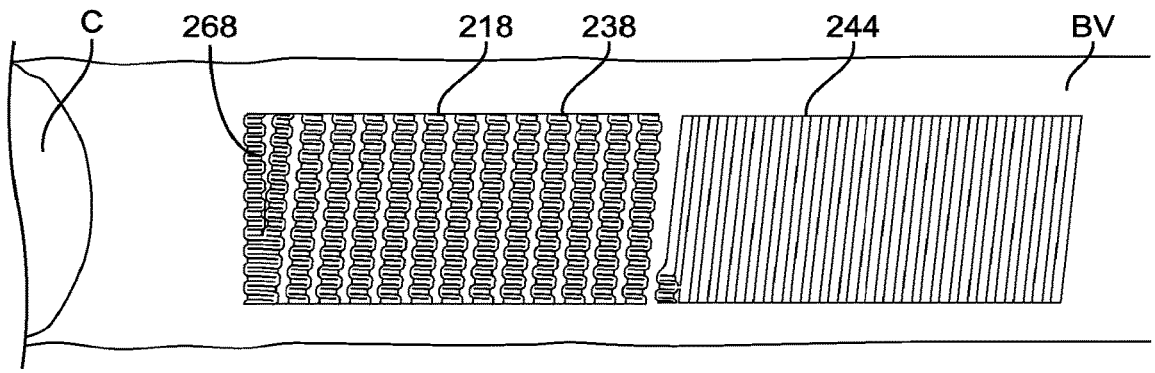
FIGS. 13A-13G illustrate use of the system of FIG. 1A for advancing and deploying the aspiration catheter of FIGS. 11A-11D in a patient's vasculature accordance with the principles of the present invention.
Figure 13B:
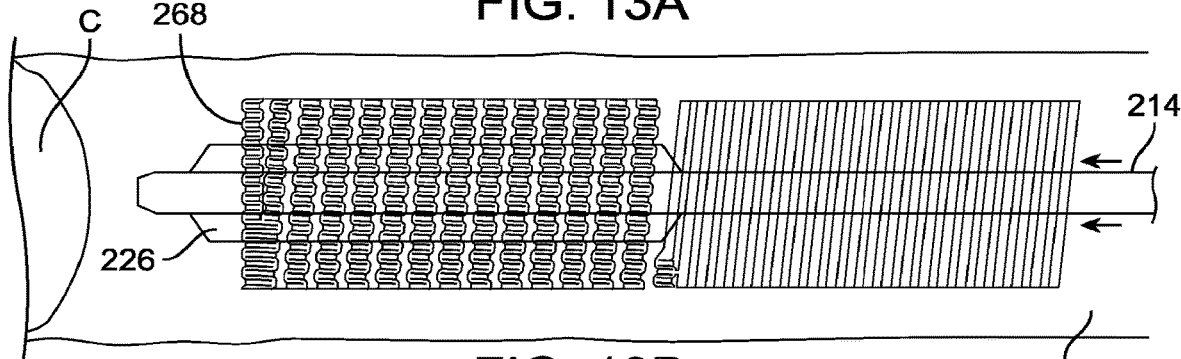
Figure 13C:
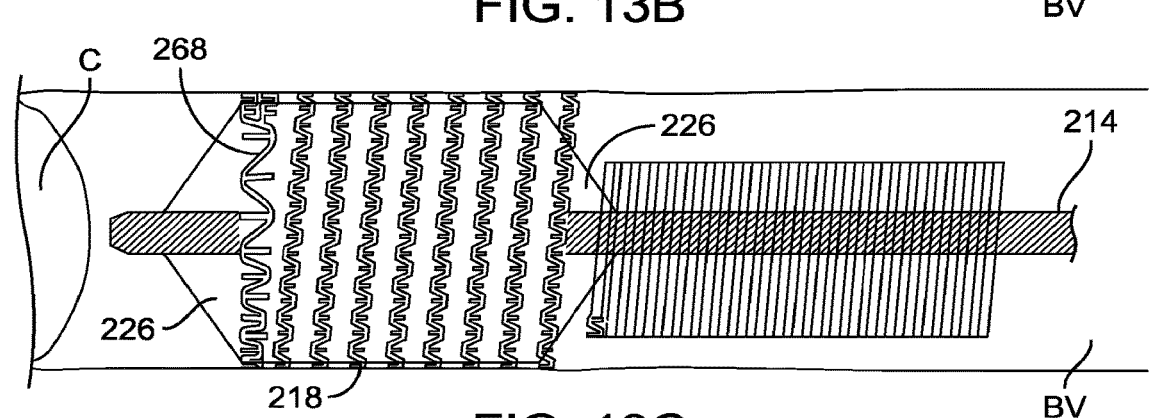
Figure 13D:
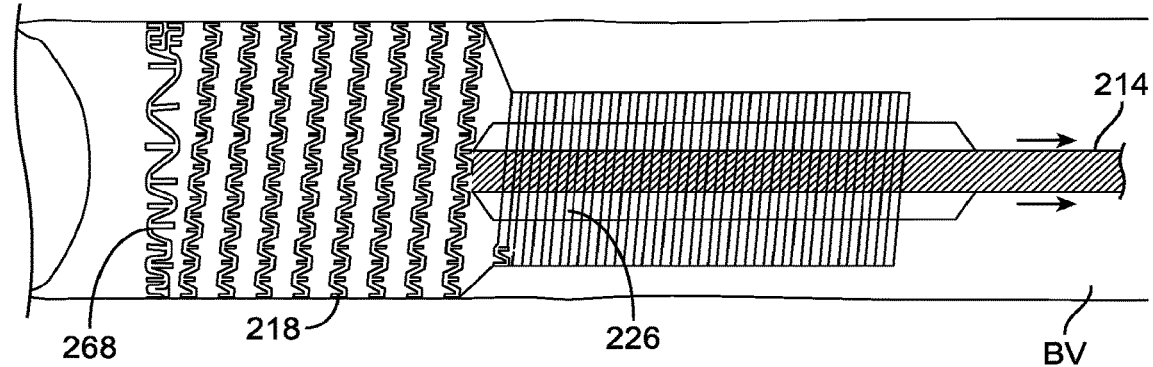
Figure 13E:
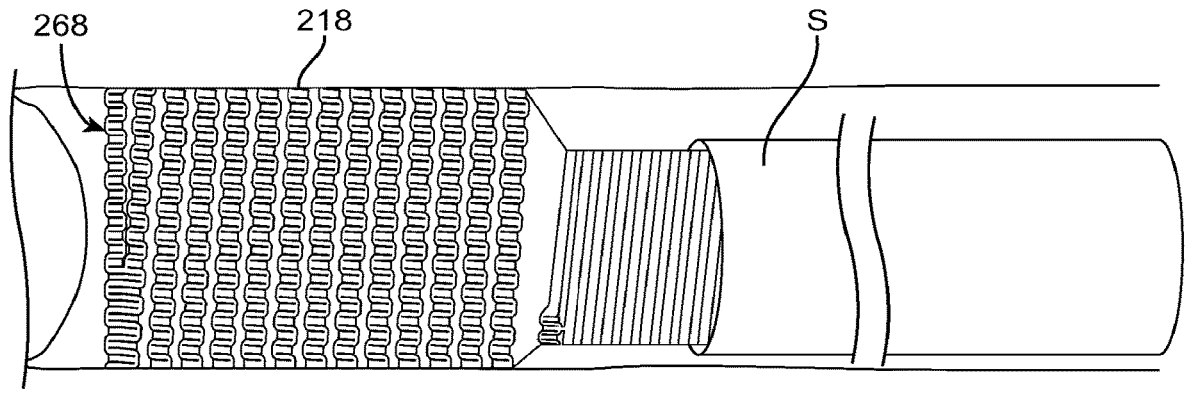
Figure 13F:
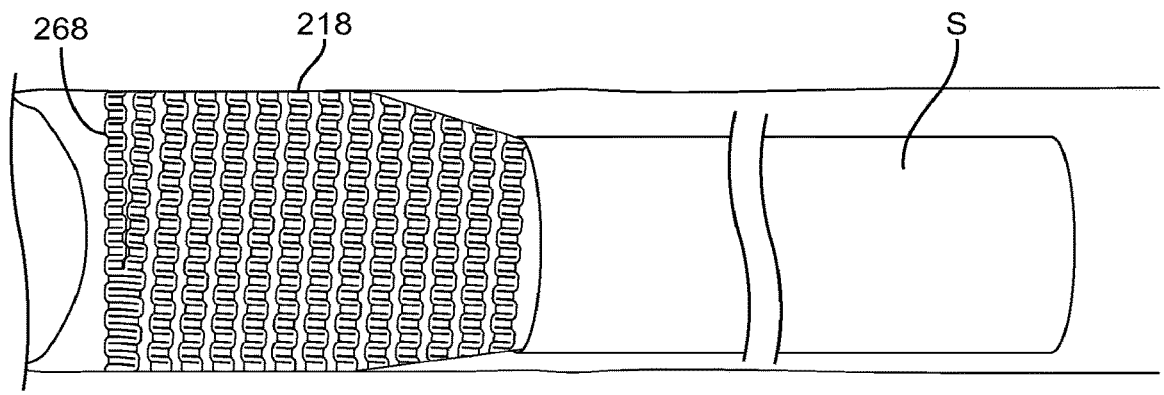
Figure 13G:
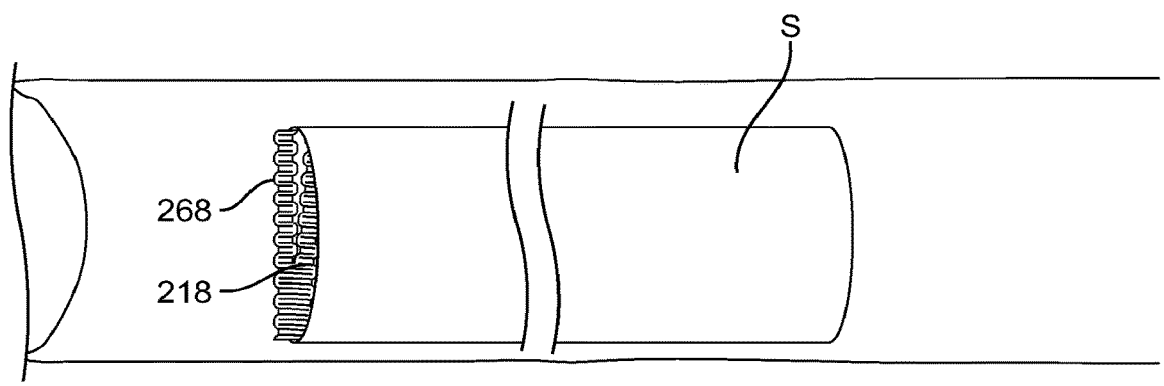

FIGS. 13A-13G illustrates advancing and deploying the expandable distal tip 218 of the aspiration catheter of FIGS. 11A-11D in a patient's vasculature accordance with the principles of the present invention. Distal tip 218 is advanced to a region of clot C in the patient's blood vessel BV, typically a cerebral blood vessel, as shown in FIG. 13A. For convenience, only the supporting scaffold 238 of distal tip 218 of aspiration catheter (without the expandable membrane 240) is illustrated. As shown in FIGS. 13B and 13C, a balloon 226 of a distal expansion catheter 214 is inflated to expand the expandable distal tip 218 of the catheter against the blood vessel wall. The aspiration catheter is typically first introduced to the blood vessel BV over a guidewire, and the distal tip expansion catheter 214 introduced after the aspiration catheter has been positioned. In other instances, the aspiration catheter and the distal tip expansion catheter 214 may be introduced together or in tandem. After the distal tip 218 of the aspiration catheter has been expanded, the distal tip expansion catheter 214 will be withdrawn, as shown in FIG. 13D. After the clot has been aspirated, the aspiration catheter be withdrawn through a sheath S, as shown in FIG. 13E, causing the expanded distal tip 218 to be constricted for removal as shown in FIGS. 13F and 13G.

FIGS. 14A and 14B illustrate how the "pitch angle" of a helical scaffold can be measured. FIG. 14A illustrates a "rolled-out" pattern of an exemplary helical scaffold 300 in its crimped or pre-expanded configuration, while FIG. 14B illustrates a "rolled-out" pattern of the same helical scaffold 300' in its radially expanded configuration. The pitch angle of the pre-expanded scaffold 300 is measured between a line L1 along the longitudinal axis of the scaffold and a line L2 drawn parallel to the rings 302 in the scaffold. The pitch angle $\alpha_1$ of the scaffold 300 in the pre-expanded or in the as delivered configuration is typically from 70° to 89.9° or more typically from 80° to 89.9, preferably from 84° to 89.9°, and more preferably from 85° to 89° degrees, and most preferably from 86° to 88°. The pitch angle $\alpha_2$ will greater than the pitch angle $\alpha_1$ for any given scaffold since the pitch angle increases as the scaffold radially expands, approaching 90° as the scaffold fully expands.

Figure 14C:
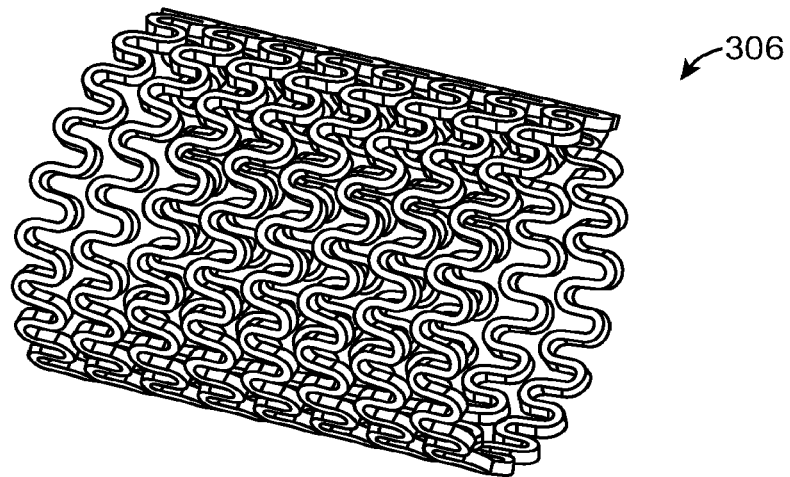
FIGS. 14C-14E illustrate distal tip supporting scaffolds having varying pitch angles and varying gap lengths between rings.
Figure 14D:
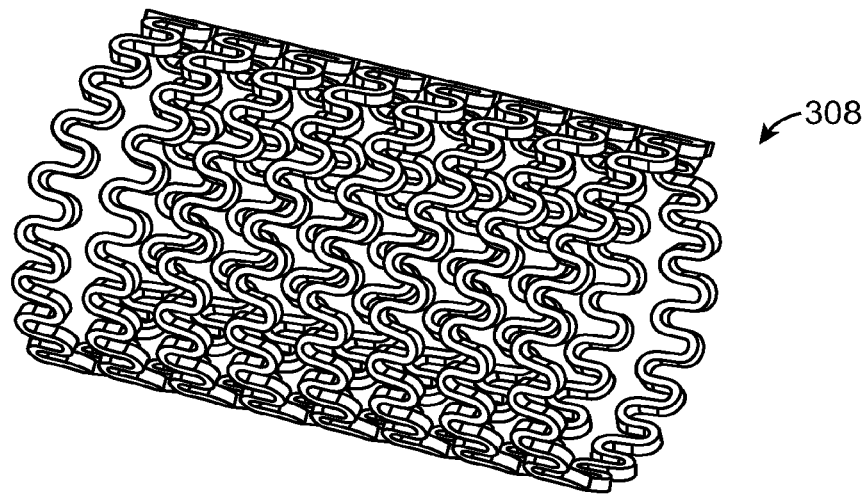
Figure 14E:
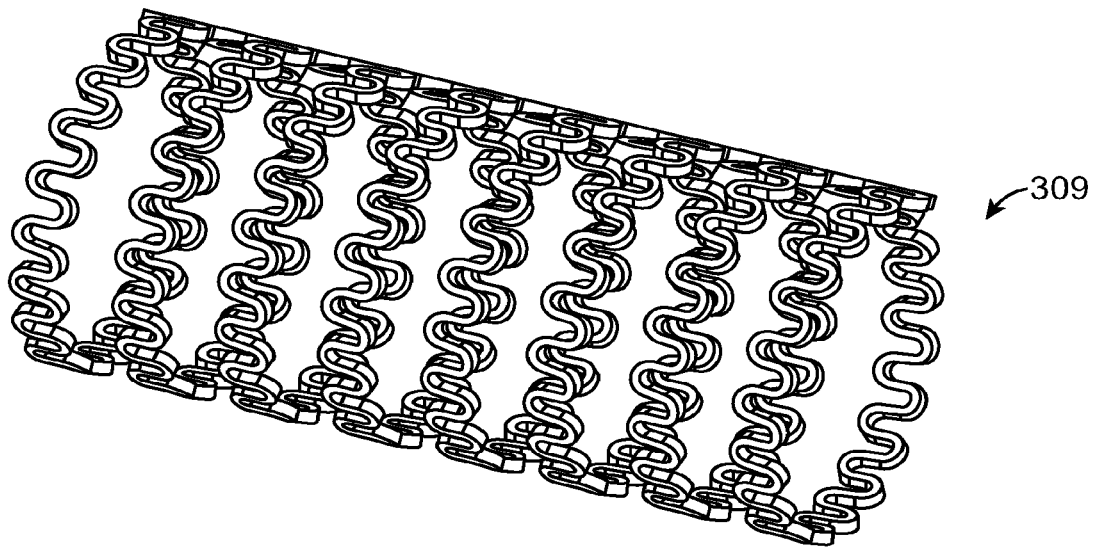

FIGS. 14C-14E illustrate distal tip supporting scaffolds having varying pitch angles. Supporting scaffold 306 shown in its pre-expanded configuration has a pitch angle of 87°. Supporting scaffold 308 shown in its pre-expanded configuration has a pitch angle of 86. Supporting scaffold 309 shown in its pre-expanded configuration has a pitch angle of 85°

FIGS. 15A-15C are detailed views illustrating different bending patterns that can be utilized in the radially expandable distal tip rings of the present invention. Supporting rings 320 having serpentine bending patterns are shown in FIG. 15A. Supporting rings 322 having zig-zag bending patterns are shown in FIG. 15B. Supporting rings 324 having box box-shaped (square-shaped) bending patterns are shown in FIG. 15C.

Figure 15D:
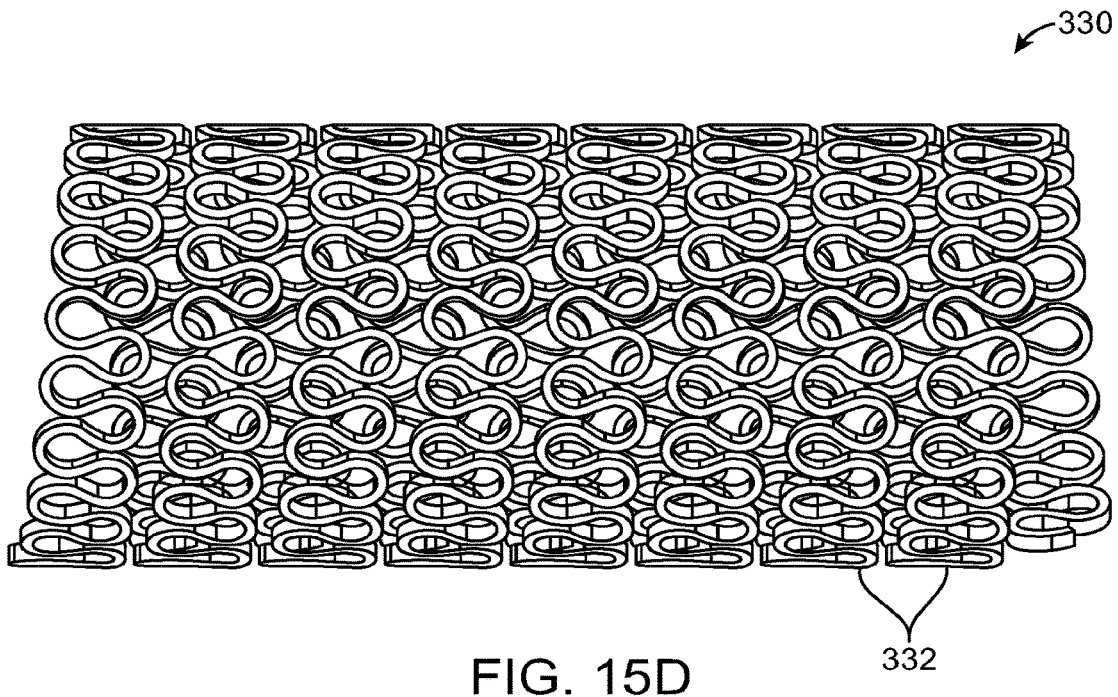
FIGS. 15D and 15E are side and perspective views of radially expandable distal tip rings of the present invention having a repeating omega-shaped cell pattern.
Figure 15E:
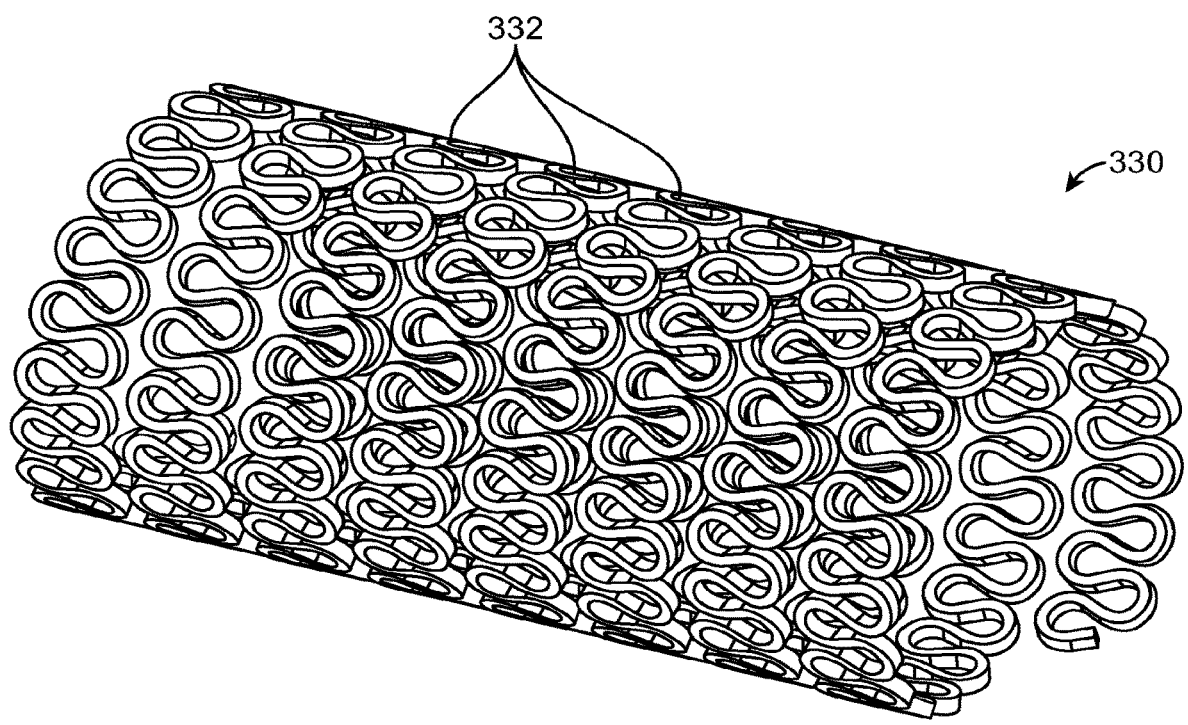

FIGS. 15D and 15E are side and perspective views of a scaffold 330 having helically arranged radially expandable rings 332 with a repeating omega-shaped cell pattern.

Figure 16:
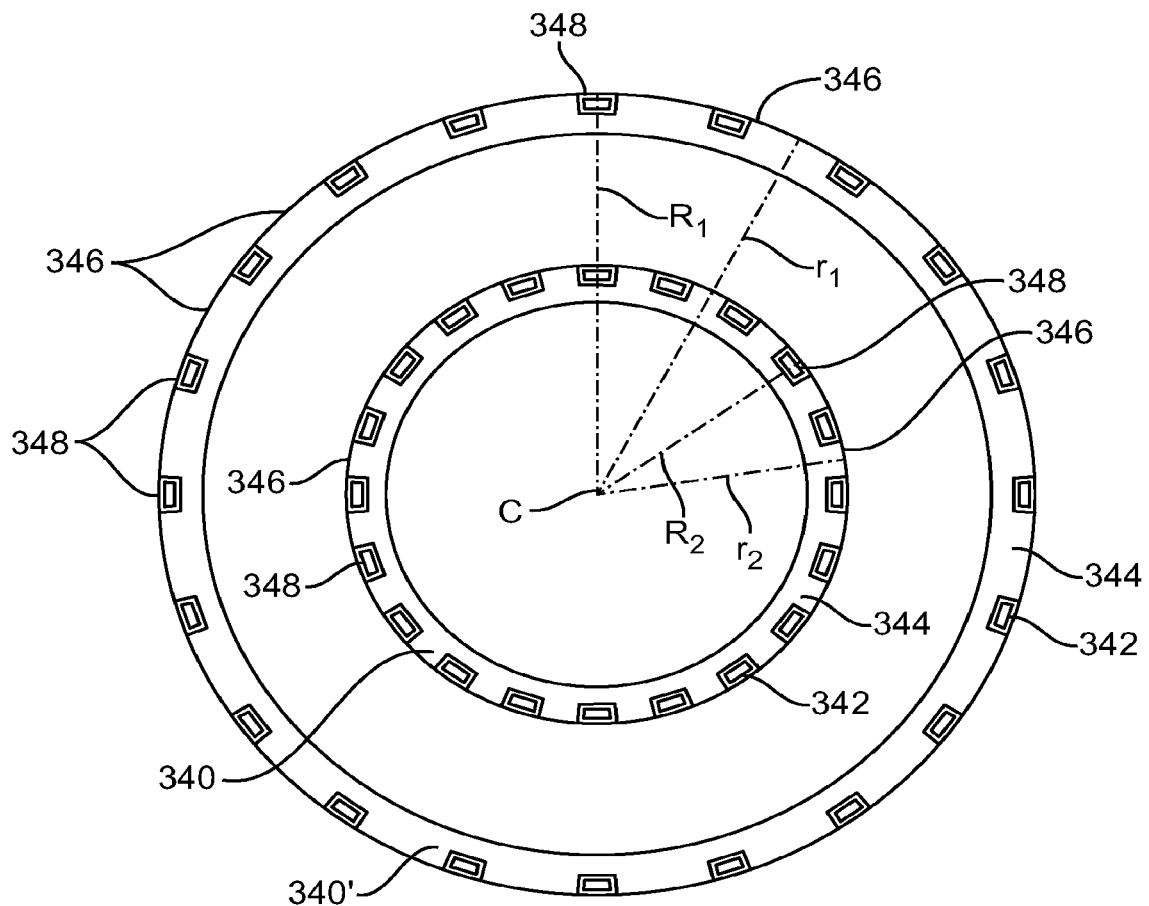
FIG. 16 illustrates the how the faceted outer surface of the radially expandable distal tip rings of the present invention approaches a circular perimeter as a measure of circularity.

FIG. 16 illustrates the how a faceted outer surface of the radially expandable distal tip region of the aspiration catheter of the present invention approaches a circular perimeter (achieves enhanced "circularity"). Cross-sectional views of an exemplary radially expandable distal tip region 340 are shown in a pre-expanded configuration (340) and a radially expanded configuration (340'). A circumferentially expanding ring 342 is embedded in a polymer membrane 344, so that the outer surface of the radially expandable distal tip region forms a number of relatively flat facets 346 between struts 348 of the scaffold 342.

In its pre-expanded configuration 340, the radially expandable distal tip region has a first radius $r_2$ from an axial center line C of the ring to the circumferential center of each facet 346 and a second radius $R_2$ from the axial center line C of the ring to the a circumferential edge of each facet 346, and wherein the length of the first radius $r_2$ is from 80% to 99.9% of the length of the second radius $R_2$, preferably being from 95% to 99.5%, more preferably being from 97.5% to 98.5%, and most preferably being from 98.5% to 99.5.

Figure 17:
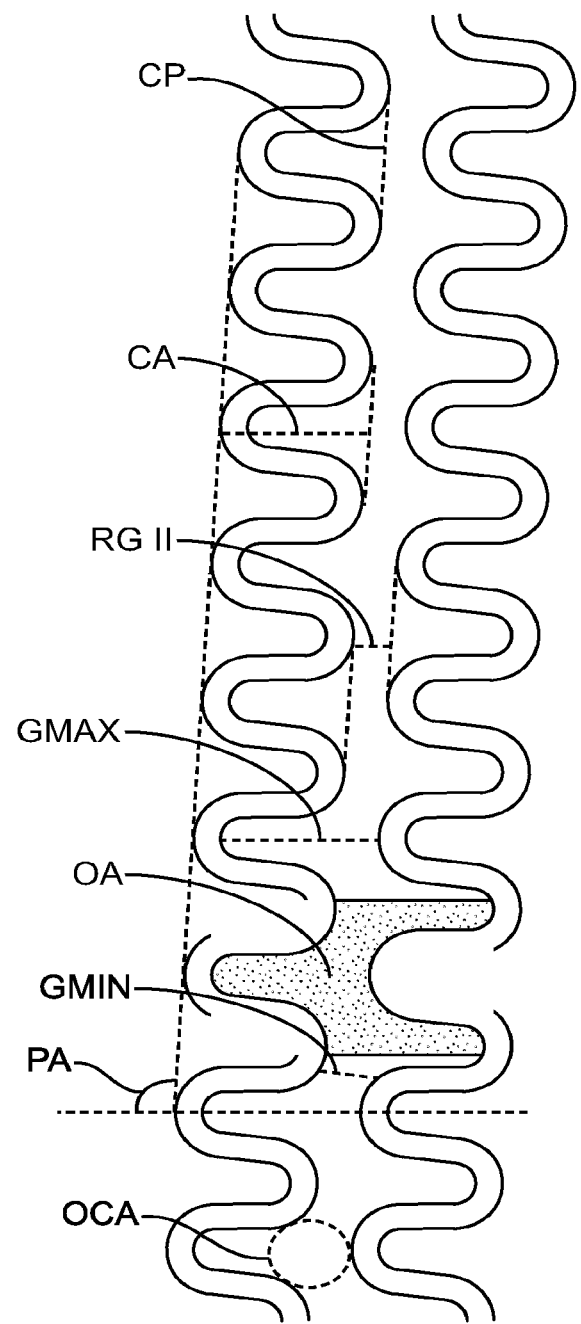
FIG. 17 identifies various characteristics that can be used to define the rings of a scaffold or structure of a helical, radially expandable distal tip of the present invention.

In its expanded configuration 340' (e.g. a radial expansion of 50% or less, usually of 100% or less, and sometimes of 200% or less), the radially expandable distal tip region has a first radius $R_1$ from the axial center line C of the ring to the circumferential center of each strut 348 and a second radius $r_1$ from the axial center line C of the ring to a circumferential edge of each facet 346, and wherein the length of the first radius is from 75% to 99% of the length of the second radius, preferably being from 97% to 99%, often being from 98% to 99%, more typically being 98.5%. A circularity in the expanded configuration greater than 97% is preferred, greater than 98% is more preferred, and greater than 98.5% is most preferred, FIG. 17 identifies various characteristics that can be used to configure the structure of a helical radially expandable distal tip rings of the present invention, with values as shown in Table 1 below.

TABLE 1

Characteristics of a Helical Ring Pattern

| Characteristic | Broad Range | Medium Range | Specific Range |
|---|---|---|---|
| CP: Cell Period (Distance between like points on circumferentially adjacent cells in a ring) | 0.1 mm to 1.2 mm | 0.15 mm to 0.4 mm | 0.2 mm to 0.35 mm |
| CA/RA: Cell Amplitude or Ring Amplitude (distance from peak to peak of cells in a ring) | 0.05 mm to 0.3 mm | 0.1 mm to 0.25 mm | 0.1 mm to 0.2 mm |
| RG: Ring Gap (distance between circumferential edges of adjacent rings) | 0 mm to 0.35 mm | 0.025 mm to 0.2 mm | 0.05 mm to 0.15 mm |
| GMAX: Maximum Gap (Length of maximum unsupported gap between adjacent rings) | 0.1 mm to 1.2 mm | 0.2 mm to 0.6 mm | 0.3 mm to 0.4 mm |
| OA: Open Cell Area (Unsupported area between adjacent cells on adjacent rings) | 0.01 $mm^2$ to 0.1 $mm^2$ | 0.01 $mm^2$ to 0.06 $mm^2$ | 0.01 $mm^2$ to 0.055 $mm^2$ |
| GMIN: Minimum Gap (Length of minimum unsupported gap between adjacent rings) | 0 mm to 0.4 mm | 0.05 mm to 0.1 mm | 0.06 mm to 0.08 mm |
| PA: Pitch Angle (Ring inclination relative to longitudinal axis of scaffold measured as an acute angle when the distal tip is in its delivery configuration) | 70 to 89.9 degree | 80 to 89 degrees | 85 to 88 degrees |
| OCA: Open circle area (Largest unsupported circular area between adjacent cells on adjacent rings) | 0.01 $mm^2$ to 0.1 $mm^2$ | 0.01 $mm^2$ to 0.05 $mm^2$ | 0.015 $mm^2$ to 0.035 $mm^2$ |

Figure 18A:
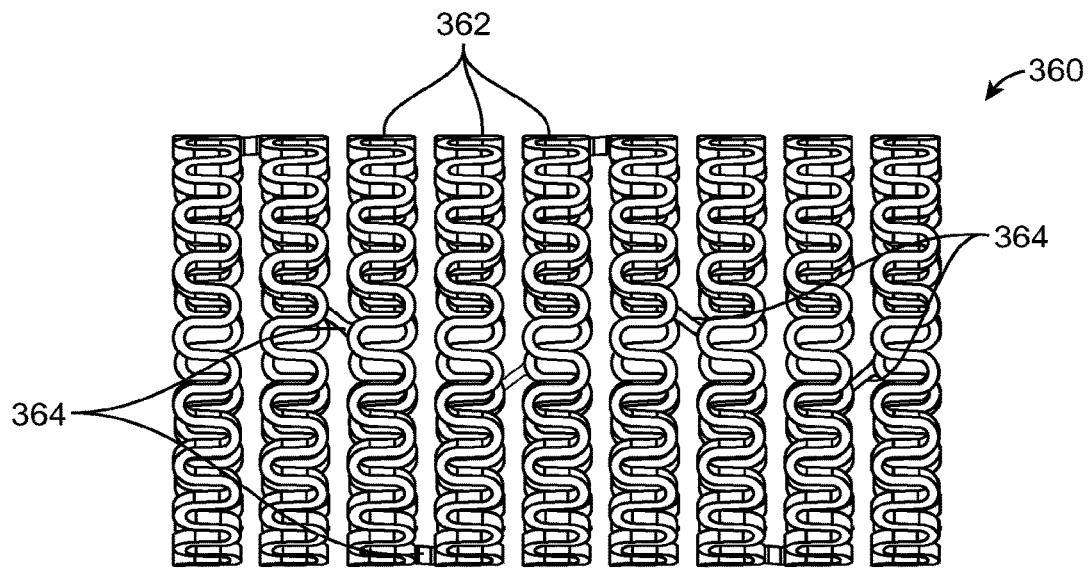
FIGS. 18A to 18C are side, perspective, and "rolled-out" views of an expandable scaffold comprising a plurality of transversely oriented, axially linked (or joined) expandable rings.
Figure 18B:
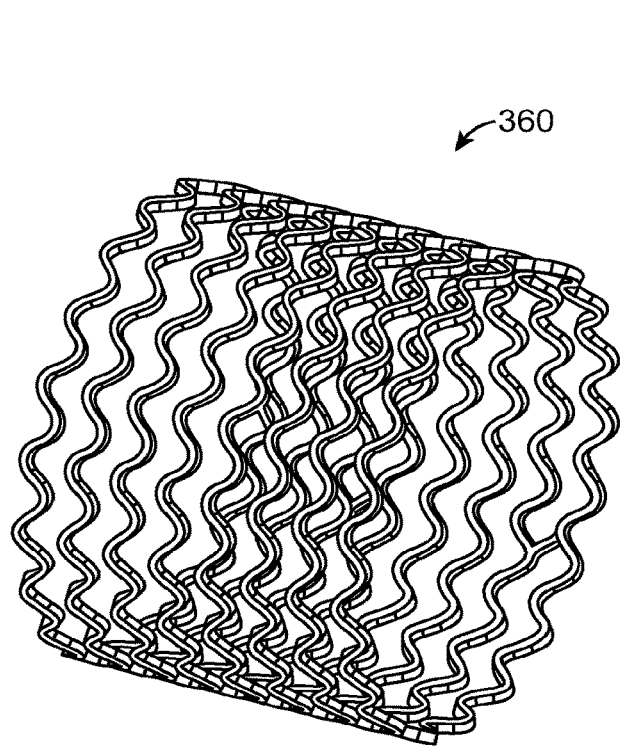
Figure 18C:
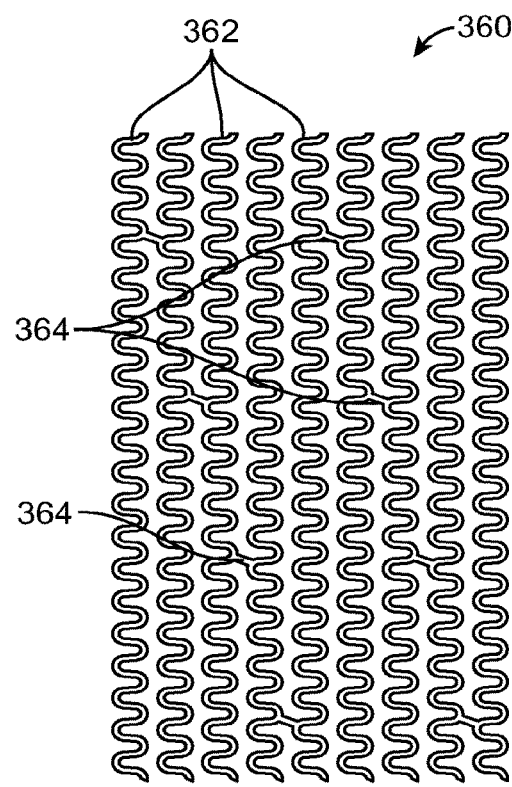

FIGS. 18A to 18C are side, perspective, and "rolled-out" views of an expandable scaffold 360 comprising a plurality of transversely oriented, axially linked expandable rings 362 joined by axial links 364.

Figure 19:
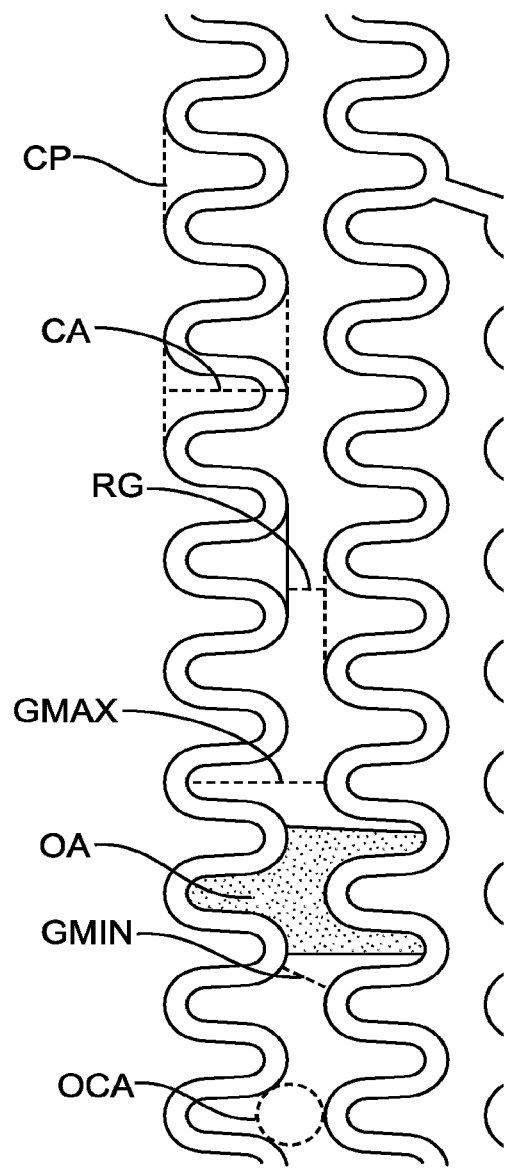
FIG. 19 identifies various characteristics that can be used to define the structure of an expandable scaffold comprising a plurality of transversely oriented, axially linked (or joined) expandable rings, such as that shown in FIGS. 18A-18C.

FIG. 19 identifies various characteristics that can be used to configure the structure of an expandable scaffold comprising a plurality of transversely oriented, axially linked expandable rings, such as that shown in FIGS. 18A-18C, with values as shown in Table 2 below.

TABLE 2

Characteristics of an Axially Linked Ring Pattern

| Characteristic | Broad Range | Medium Range | Specific Range |
|---|---|---|---|
| CP: Cell Period (Distance between like points on circumferentially adjacent cells in a ring) | 0.1 mm to 1.2 mm | 0.15 mm to 0.4 mm | 0.2 mm to 0.35 mm |
| CA/RA: Cell Amplitude or Ring Amplitude (distance from peak to peak of cells in a ring) | 0.05 mm to 0.3 mm | 0.1 mm to 0.25 mm | 0.1 mm to 0.2 mm |
| RG: Ring Gap (distance between circumferential edges of adjacent rings) | 0 mm to 0.3 mm | 0.025 mm to 0.2 mm | 0.05 mm to 0.15 mm |
| GMAX: Maximum Gap (Length of maximum unsupported gap between adjacent rings) | 0.1 mm to 1.2 mm | 0.2 mm to 0.6 mm | 0.3 mm to 0.4 mm |
| OA: Open Cell Area (Unsupported area between adjacent cells on adjacent rings) | 0.01 $mm^2$ to 0.1 $mm^2$ | 0.01 $mm^2$ to 0.06 $mm^2$ | 0.01 $mm^2$ to 0.055 $mm^2$ |
| GMIN: Minimum Gap (Length of minimum unsupported gap between adjacent rings) | 0 mm to 0.4 mm | 0.05 mm to 0.1 mm | 0.06 mm to 0.08 mm |

TABLE 2-continued

Characteristics of an Axially Linked Ring Pattern

| Characteristic | Broad Range | Medium Range | Specific Range |
| --- | --- | --- | --- |
| OCA: Open circle area (Largest unsupported circular area between adjacent cells on adjacent rings) | 0.01 $mm^2$ to 0.1 $mm^2$ | 0.01 $mm^2$ to 0.5 $mm^2$ | 0.015 $mm^2$ to 0.035 $mm^2$ |

Figure 20A:
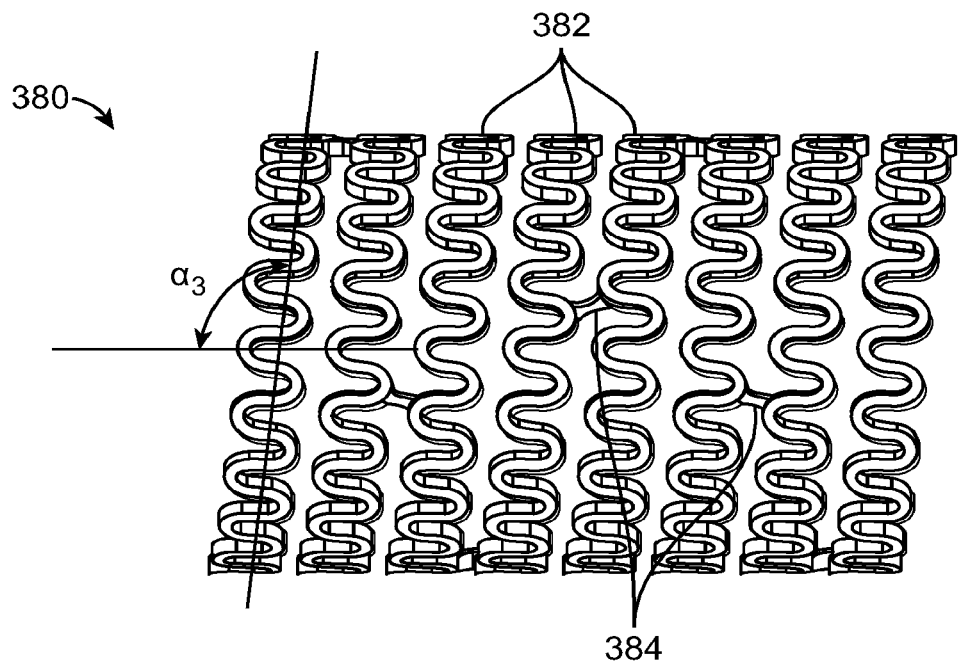
FIGS. 20A and 20B are side and "rolled-out" views of an expandable scaffold comprising a plurality of parallel, axially linked (or joined) expandable rings which are inclined relative to a longitudinal axis of the scaffold.
Figure 20B:
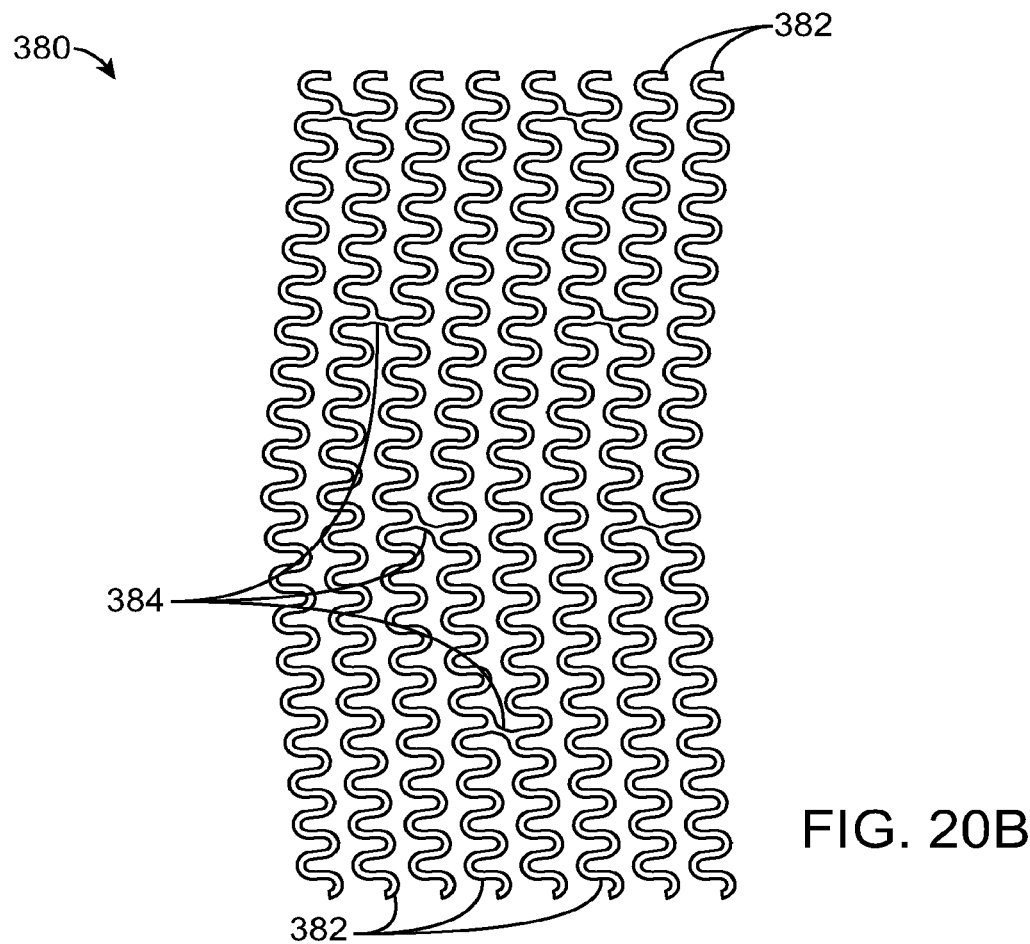

FIGS. 20A and 20B are side and "rolled-out" views of an expandable scaffold 380 comprising a plurality of parallel, axially linked expandable rings 382 which are joined by axially links 384 inclined relative to a longitudinal axis of the scaffold at an acute pitch angle $α_3$.

Figure 21:
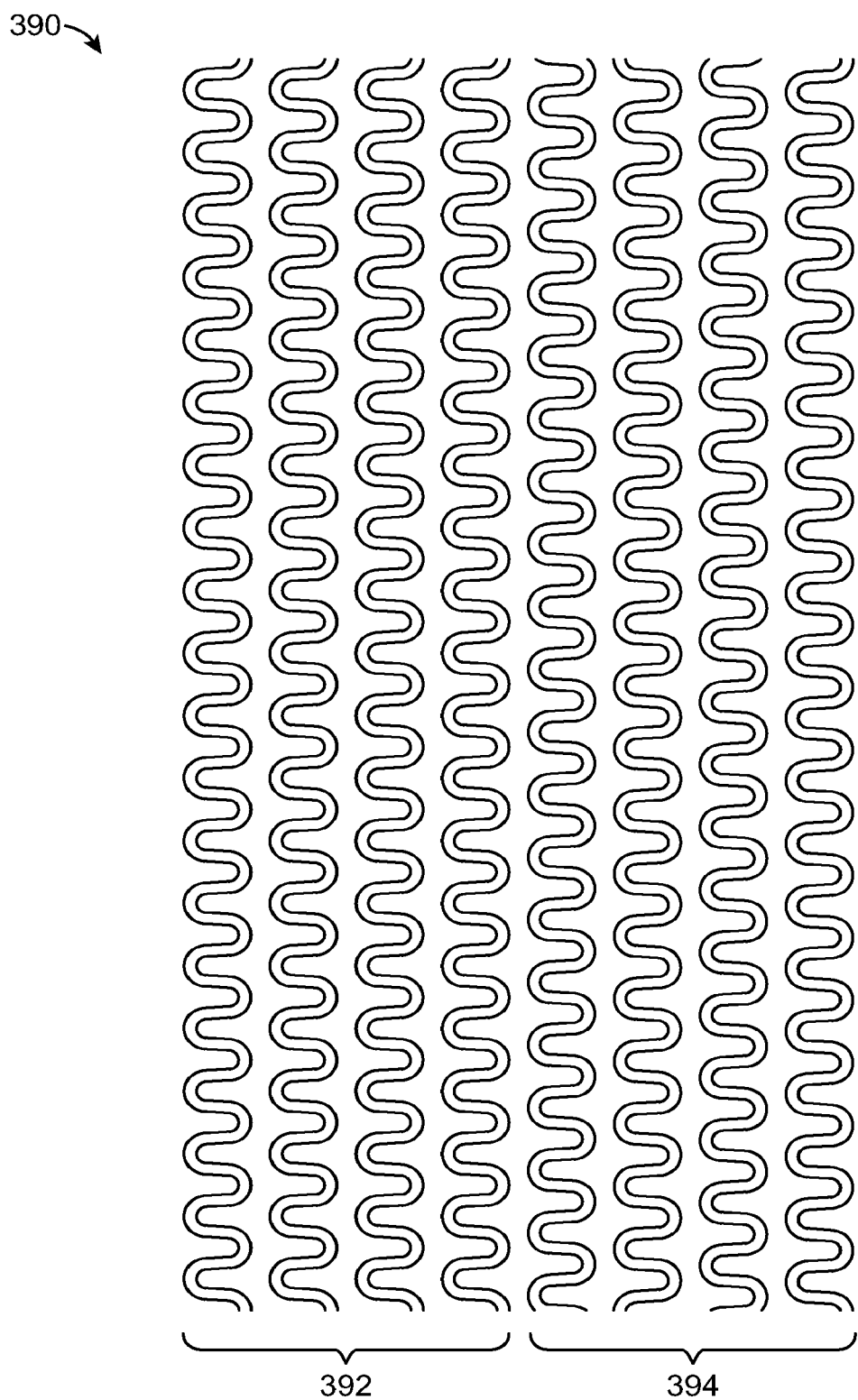
FIG. 21 is a "rolled-out" view of an expandable scaffold having segment with cells aligned in phase and out-of-phase.

FIG. 21 is a "rolled-out" view of an expandable scaffold 390 having segments 392 and 394 with cells aligned in-phase and out-of-phase, respectively.

Figure 22:
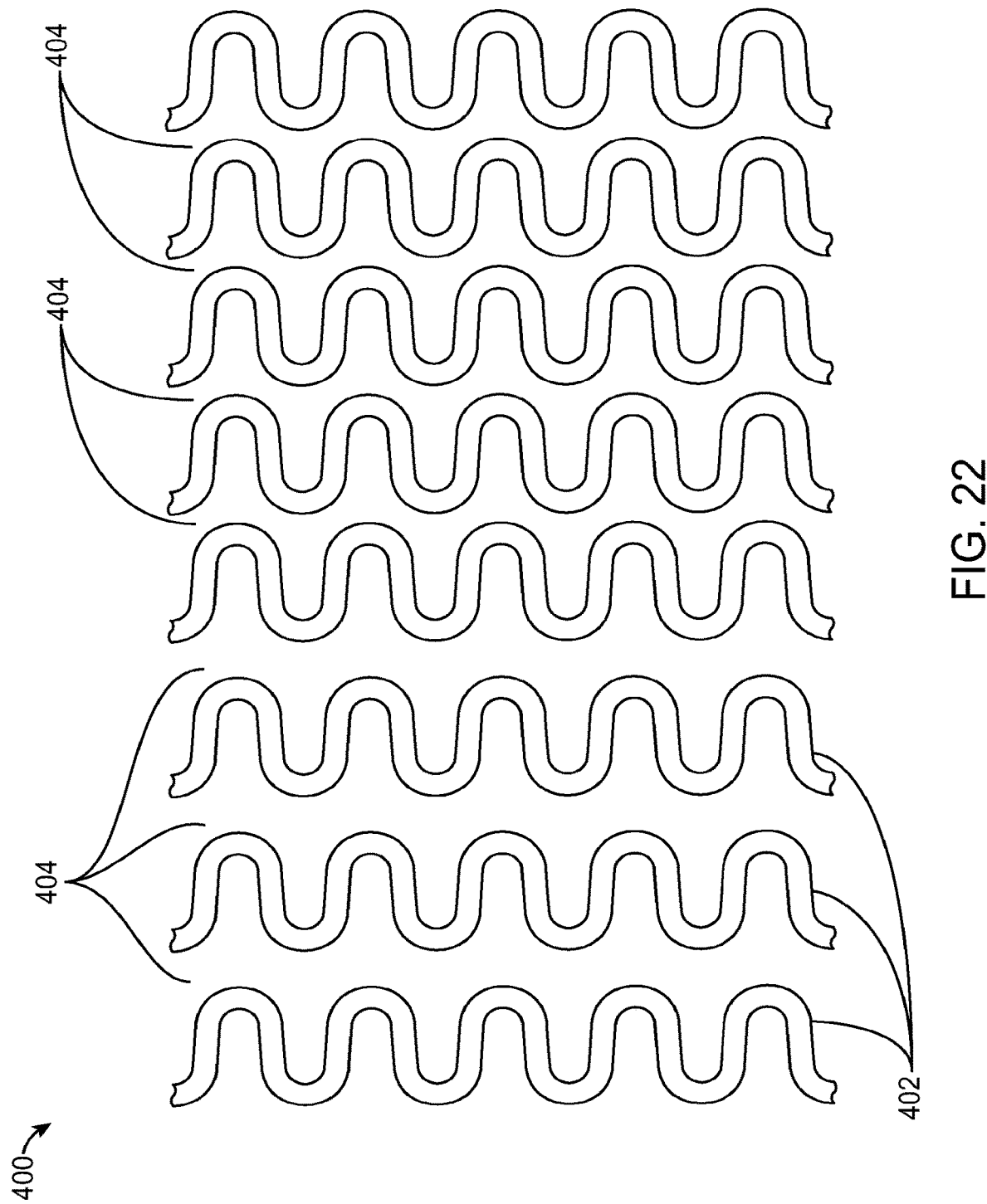
FIG. 22 is a "rolled-out" view of an expandable scaffold comprising a plurality of rings with gaps therebetween having varying lengths.

FIG. 22 is a "rolled-out" view of an expandable scaffold 400 comprising a plurality of rings 402 with gaps 404 therebetween having varying lengths.

Figure 23A:
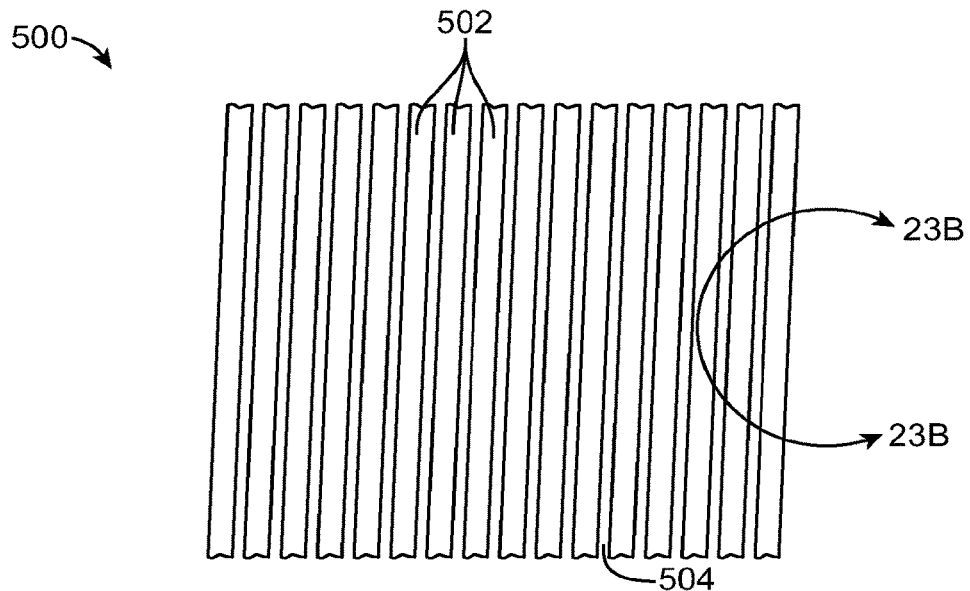
FIG. 23A is a "rolled-out" view of an expandable scaffold comprising a plurality of rings with gaps therebetween arranged in a helical pattern.
Figure 23B:
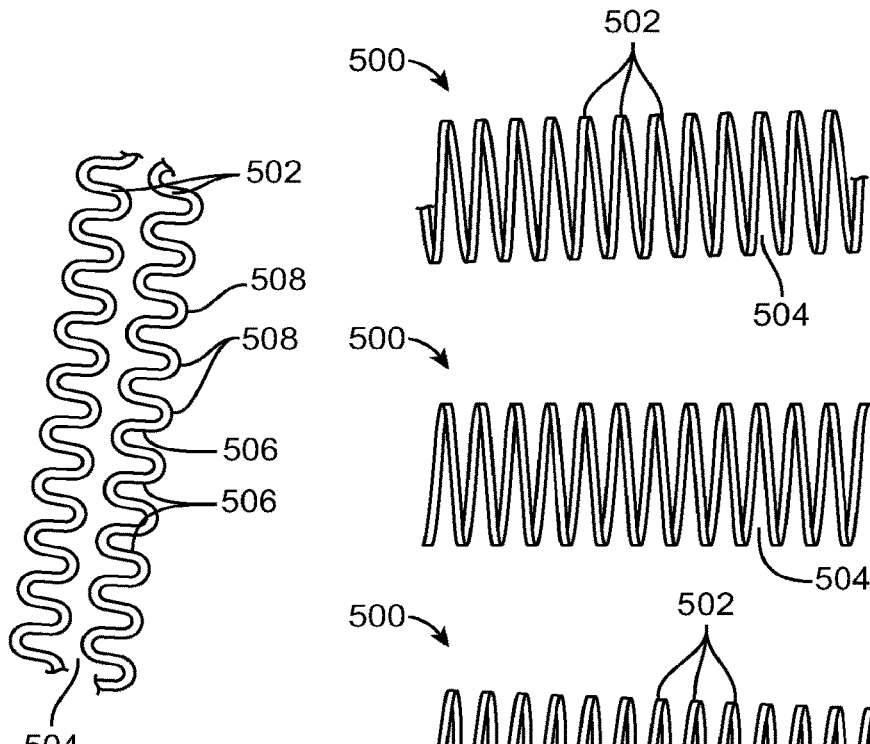
FIG. 23B is a detailed exemplary view of the rings of FIG. 23A showing that each ring has a serpentine pattern.

FIG. 23A is a "rolled-out" view of an expandable scaffold 500 comprising a plurality of rings 502 with gaps 504 therebetween arranged in a helical pattern. The rings 502 are "smooth," i.e., linear and free from bends and curves in the rolled-out pattern. As shown in detailed view FIG. 23B, the rings 502 will each a serpentine pattern. Although a simple serpentine pattern comprising struts 506 joined by crowns 508 is illustrated in FIG. 23B, the rings 502 may comprise any cell patterns described herein or otherwise known in the art.

Figure 23C:
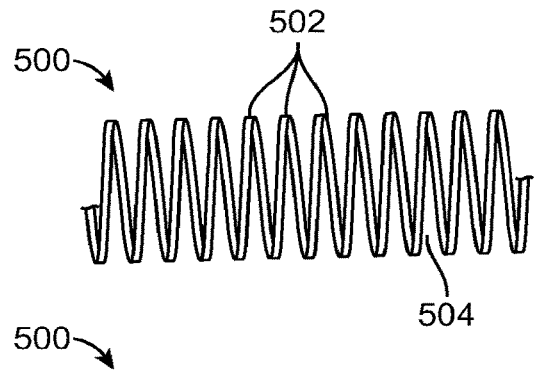
FIGS. 23C to 23E are rotated side views of the expandable scaffold of FIG. 23A.
Figure 23D:
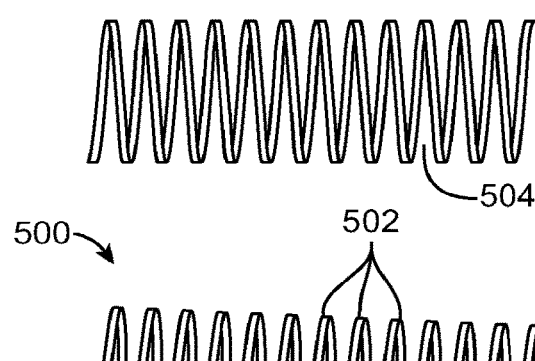
Figure 23E:
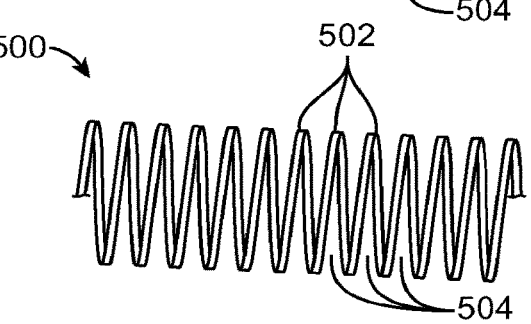

FIGS. 23C to 23E are rotated side views of the expandable scaffold 500 of FIG. 23A. The view of the scaffold 500 as shown in FIG. 23D is rotated 90° in a first rotational direction relative to the view in FIG. 23C while view shown in FIG. 23E is rotated 90° in the opposite rotational direction. As the rings 502 of scaffold 500 are "smooth," i.e., free from bends, the side view does not vary as the scaffold is rotated about is longitudinal axis.

Figure 24A:
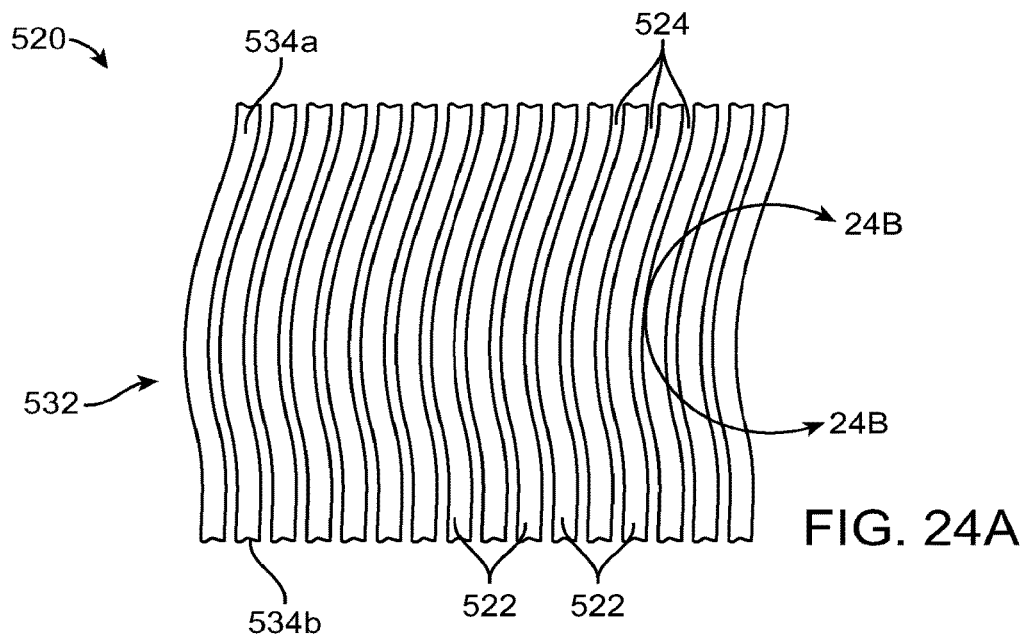
FIG. 24A is a "rolled-out" view of an expandable scaffold comprising a plurality of rings with gaps therebetween arranged in a helical pattern where individual rings have a first curved shape in the rolled-out pattern.
Figure 24B:
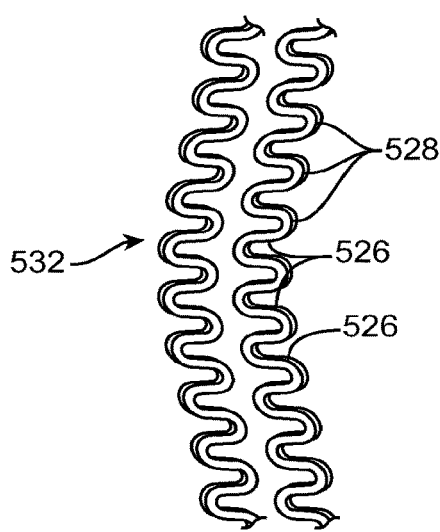
FIG. 24B is a detailed view of the rings of FIG. 24A showing that each ring has a serpentine pattern.

FIG. 24A is a "rolled-out" view of an expandable scaffold 520 comprising a plurality of rings 522 with gaps 524 therebetween arranged in a helical pattern where individual rings have a first curved shape in the rolled-out pattern. The individual rings 522 are non-linear, including two curved or bent regions 532, one of which spans the joined ends, e.g., 534a and 534b when the scaffold is rolled. As shown in detailed view FIG. 24B, the rings 522 will each a serpentine pattern. Although a simple serpentine pattern comprising struts 526 joined by crowns 528 is illustrated in FIG. 24B, the rings 522 may comprise any cell patterns described herein or otherwise known in the art.

Figure 24C:
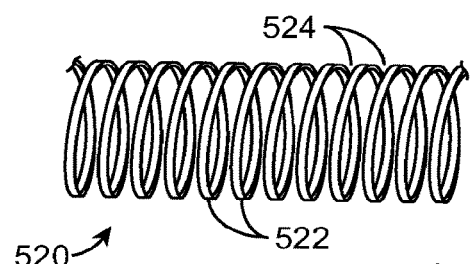
FIGS. 24C to 24E are rotated side views of the expandable scaffold of FIG. 24A.
Figure 24D:
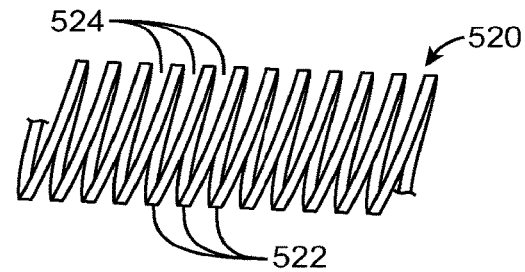
Figure 24E:
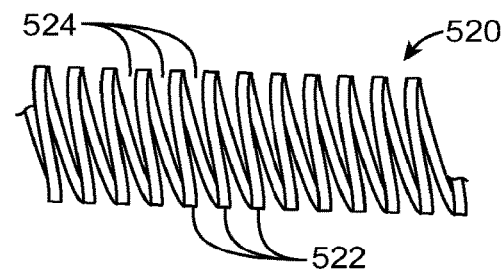

FIGS. 24C to 24E are rotated side views of the expandable scaffold 520 of FIG. 24A. The view of the scaffold 520 as shown in FIG. 24D is rotated 90° in a first rotational direction relative to the view in FIG. 24C while view shown in FIG. 24E is rotated 90° in the opposite rotational direction. The curves 532 in rings 522 of scaffold 520 cause the observed inclination of each ring 522 to shift from a rightward tilt, as shown in FIG. 24D, to a leftward tilt, as shown in FIG. 24E.

Figure 25A:
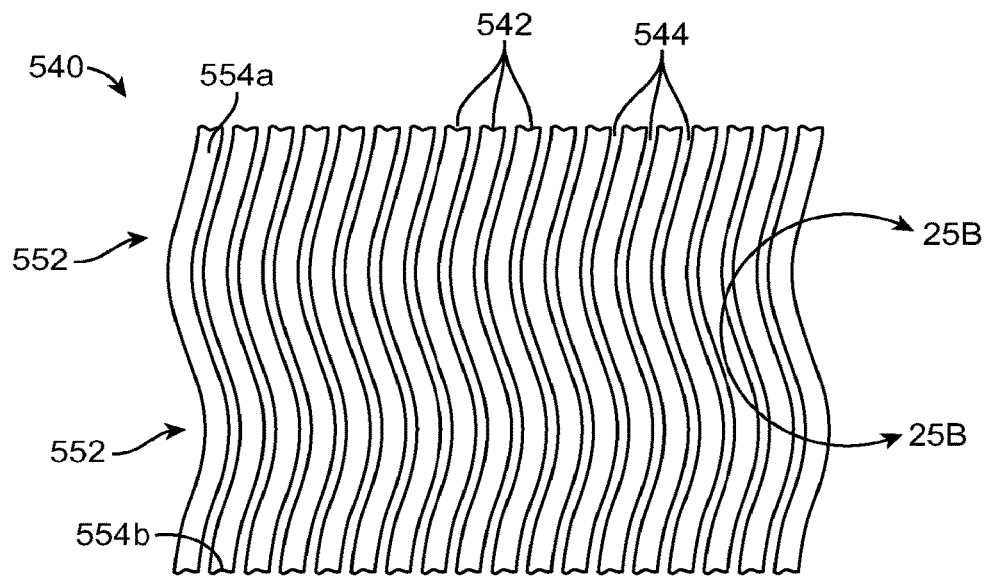
FIG. 25A is a "rolled-out" view of an expandable scaffold comprising a plurality of rings with gaps therebetween arranged in a helical pattern where individual rings have a second curved shape in the rolled-out pattern.

FIG. 25A is a "rolled-out" view of an expandable scaffold 540 comprising a plurality of rings 542 with gaps 544 therebetween arranged in a helical pattern where individual rings have a second curved shape in the rolled-out pattern. The individual rings 542 are non-linear, including three curved or bent regions 552 (one of which spans the joined ends 554a and 554b when the scaffold is rolled). As shown in detailed view FIG. 25B, the rings 542 will each a serpentine pattern. Although a simple serpentine pattern comprising struts 546 joined by crowns 548 is illustrated in FIG. 25B, the rings 542 may comprise any cell patterns described herein or otherwise known in the art.

Figure 25C:
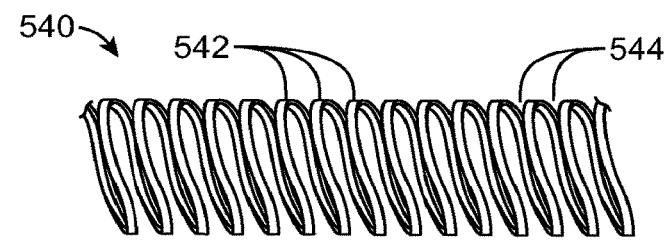
FIGS. 25C to 25E are rotated side views of the expandable scaffold of FIG. 25A.
Figure 25B:
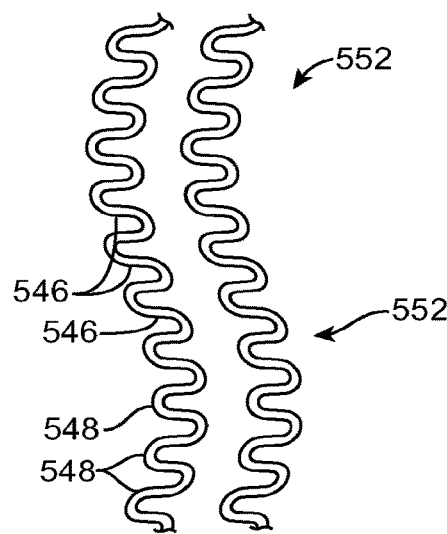
FIG. 25B is a detailed exemplary view of the rings of FIG. 25A showing that each ring has a serpentine pattern.
Figure 25D:
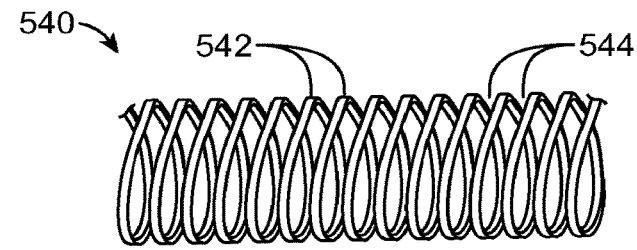
Figure 25E:
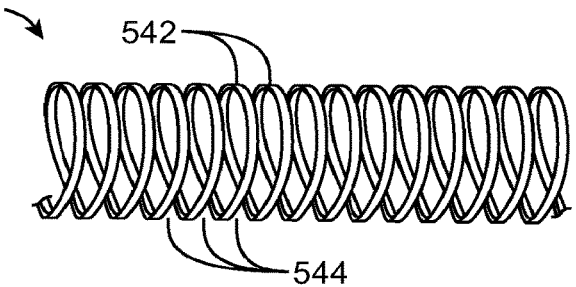

FIGS. 25C to 25E are rotated side views of the expandable scaffold 540 of FIG. 25A. The view of the scaffold 540 as shown in FIG. 25D is rotated 90° in a first rotational direction relative to the view in FIG. 25C while view shown in FIG. 25E is rotated 90° in the opposite rotational direction. The curves 552 in rings 542 of scaffold 540 cause the observed inclination of each ring 542 to shift back-and-forth as the scaffold is rotated relative its longitudinal axis, as can be seen by comparing the imaged in FIGS. 25C, 25D, and 25E.

Figure 26:
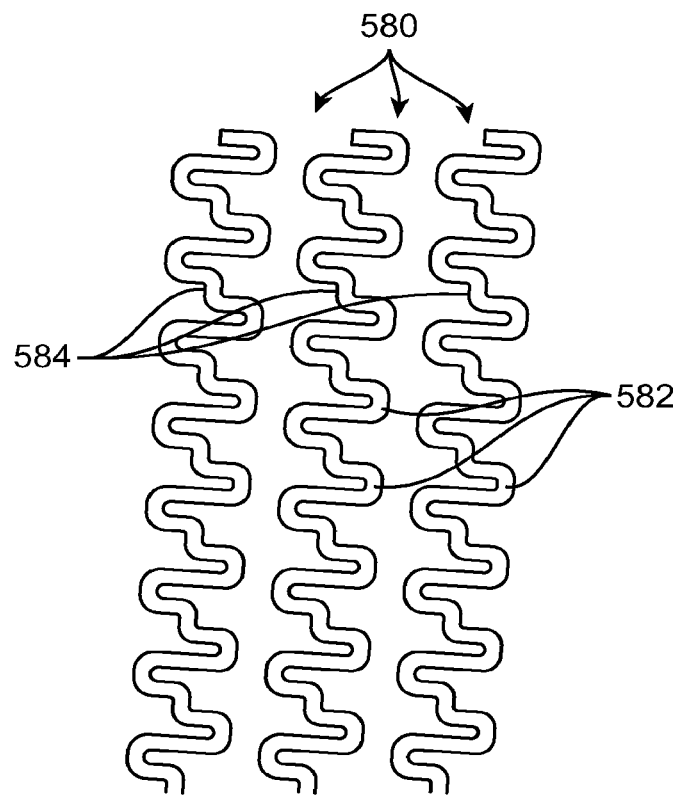
FIG. 26 is "rolled-out" view of a ring pattern comprising S-shaped expandable elements joined by non-extendable circumferential links shown prior to expansion.

FIG. 26 is "rolled-out" view of a ring pattern comprising rings 580 having S-shaped expandable elements 582 joined by non-extendable circumferential links 584 shown prior to expansion.

Figure 27:
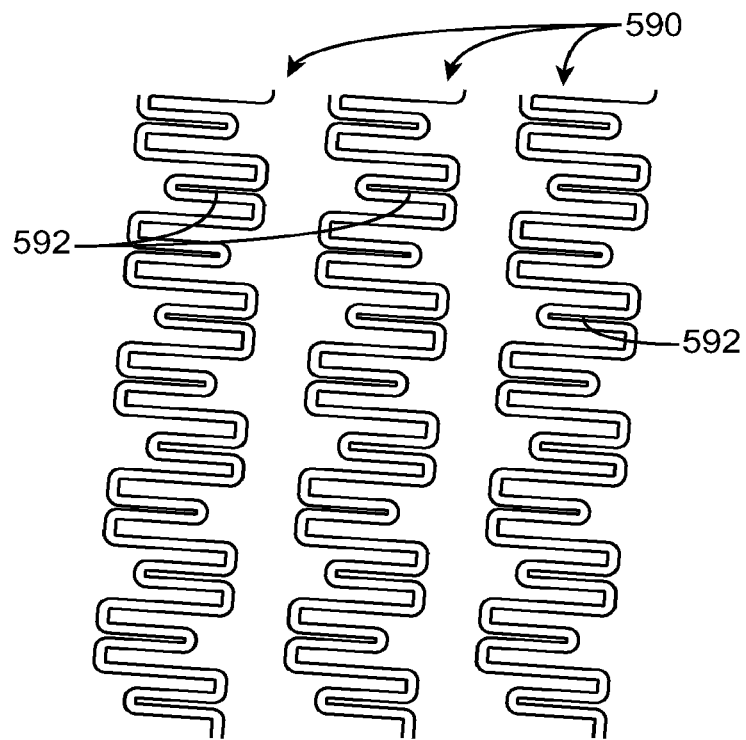
FIG. 27 is "rolled-out" view of a ring pattern comprising a bent wire having integrated cantilevered supporting elements.

FIG. 27 is "rolled-out" view of a ring pattern comprising rings 590 formed from a wire bent into a serpentine pattern having integrated cantilevered supporting elements 592 formed by tight U-shaped turns that are glued, soldered, welded or otherwise bonded together to prevent separation.

Figure 28A:
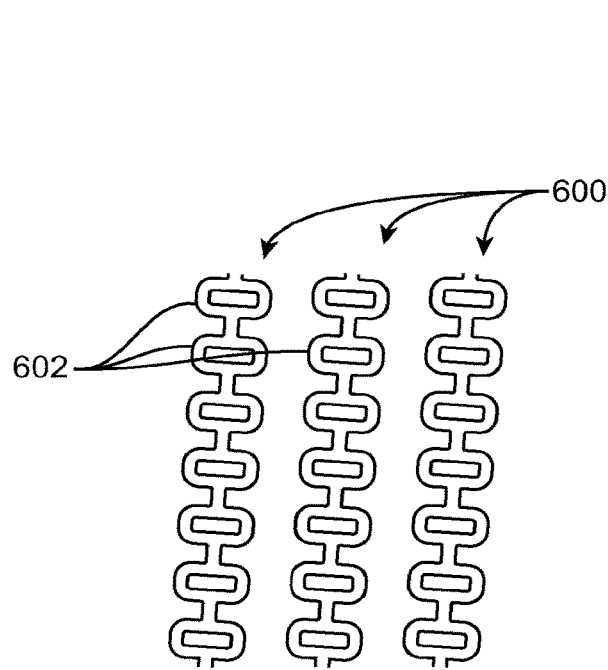
FIGS. 28A and 28B are "rolled-out" views of a closed-cell box ring pattern shown in its non-expanded and expanded configurations, respectively.
Figure 28B:
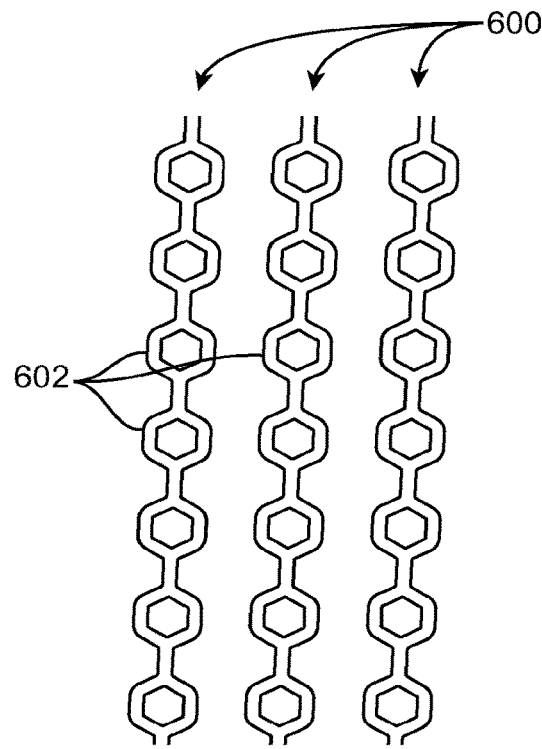

FIGS. 28A and 28B are "rolled-out" views of a ring pattern comprising closed-cell box rings 600 shown in its non-expanded and expanded configurations, respectively. Boxes 602 in each ring circumferentially elongate from a rectangular, non-expanded shape as shown in FIG. 28A to a generally hexagonal, elongated shape, as shown in FIG. 28B. Such elongation allows each ring to radially expand in response to an opening force provided by a balloon or other deployment tool.

Figure 29A:
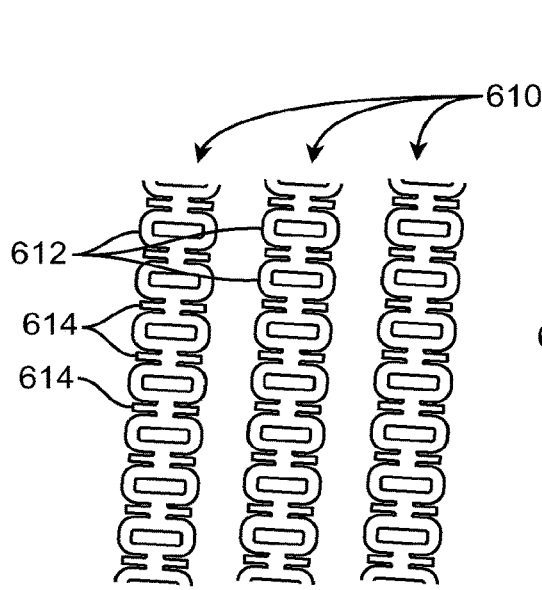
FIGS. 29A and 29B are "rolled-out" views of a closed-cell box ring pattern shown in its non-expanded and expanded configurations, respectively, further comprising cantilevered supporting elements recessed between circumferentially adjacent box elements in the non-expanded configuration.
Figure 29B:
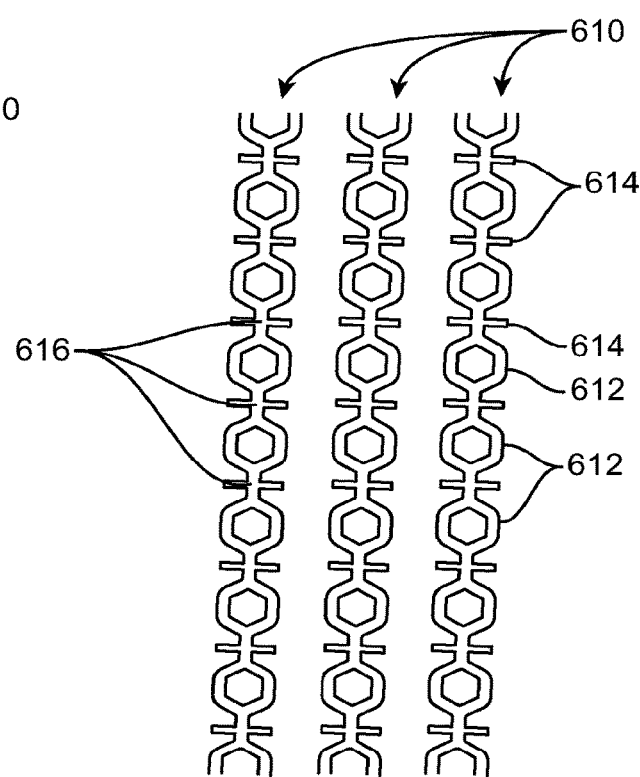

FIGS. 29A and 29B are "rolled-out" views of a rings 610 comprising closed-cell boxes 612, shown in its non-expanded and expanded configurations, respectively. The rings 610 are similar to the rings 600 illustrated in FIGS. 28A and 28B. rings 610, except that they further comprise cantilevered supporting elements 614 recessed between attached to circumferential links 616 circumferentially adjacent box elements 612 in the non-expanded configuration (FIG. 29A). The cantilevered supporting elements 614 remain in spaces between adjacent expanded boxes to provide further support for the surrounding membrane (not shown) after the rings are radially expanded, as shown in FIG. 29B.

Figure 30A:
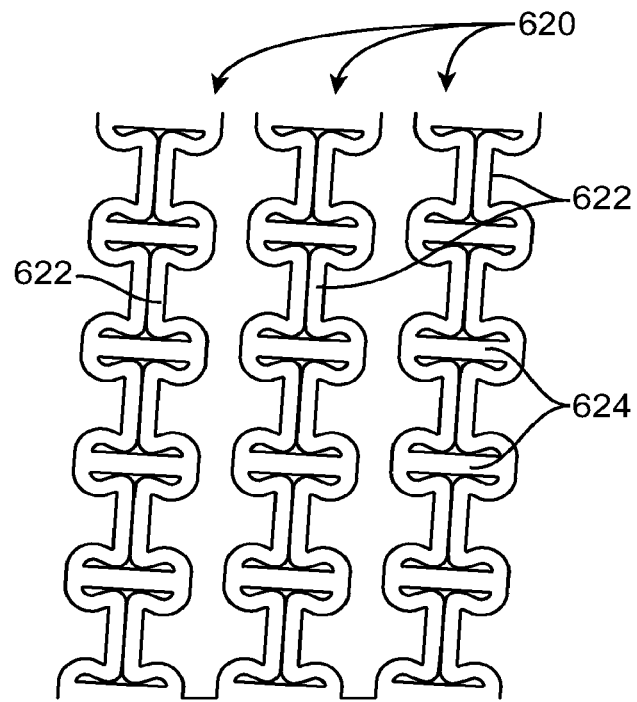
FIGS. 30A and 30B are "rolled-out" views of an alternative closed-cell box ring pattern shown in its non-expanded and expanded configurations, respectively, further comprising cantilevered supporting elements recessed between circumferentially adjacent box elements in the non-expanded configuration.
Figure 30B:
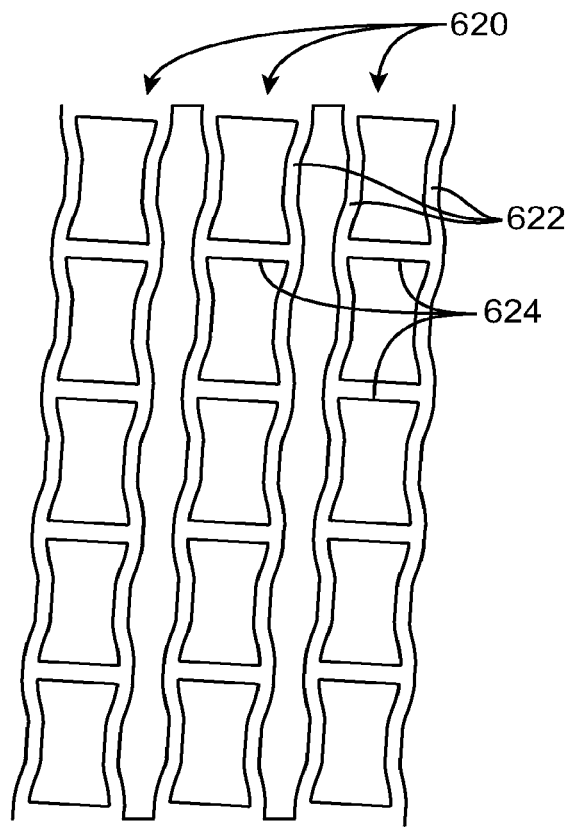

FIGS. 30A and 30B are "rolled-out" views of rings 620 comprising alternative closed-cell boxes formed from side members 622 and cross members 624. The side members are initially formed in a U-shape when the rings are in a non-expanded configuration, as shown in FIG. 30A. The U-shape elongates as the rings are radially expanded, as shown in FIG. 30B.

Figure 31A:
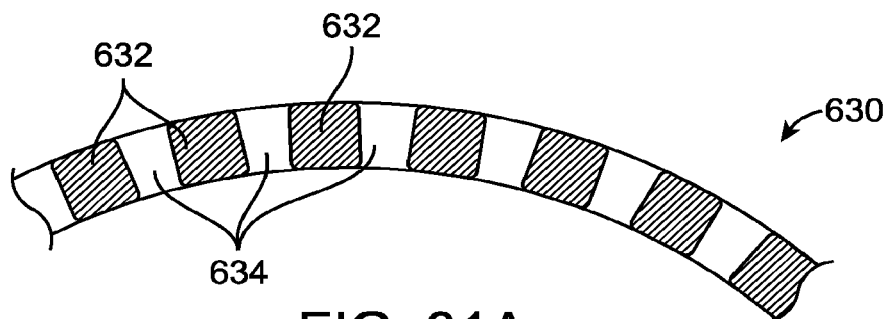
FIGS. 31A to 31C illustrate an exemplary method for embedding a radially expandable supporting scaffold or other structure in a polymer membrane.
Figure 31B:
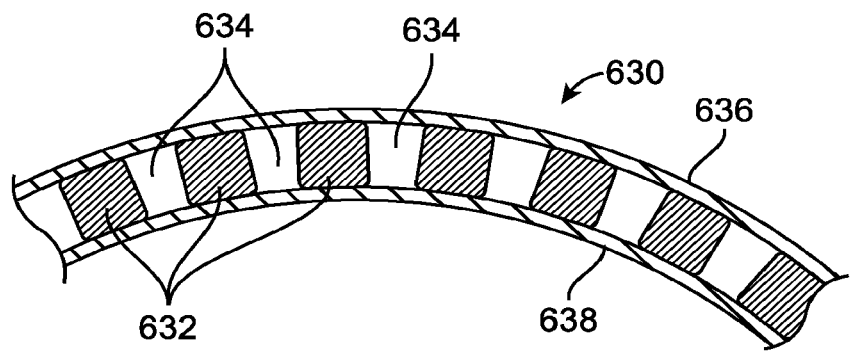
Figure 31C:
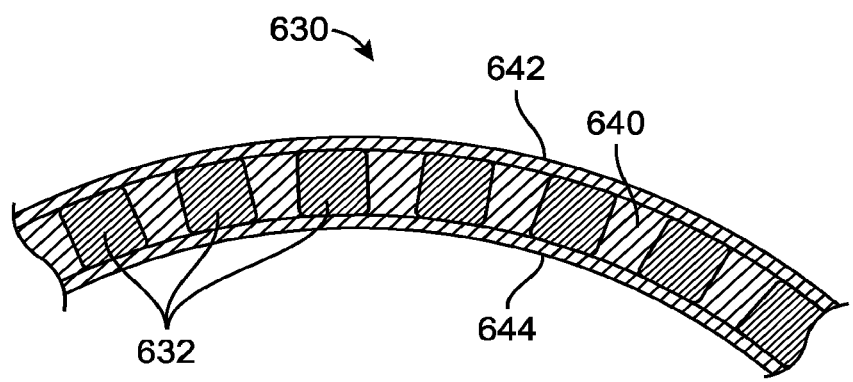

FIGS. 31A to 31C illustrate an exemplary method for embedding a radially expandable supporting scaffold 630 in a polymer membrane 640 (one or more membranes formed from the same or different material). The supporting scaffold 630 has a serpentine pattern with struts 632 having gaps 634 therebetween, as shown in FIG. 31A. The supporting scaffold 630 may be embedded in the polymer membrane 640 by first placing sheets 636 and 638 of the desired polymer or polymers over exterior and interior surfaces of the rings 630, as shown in FIG. 31B. By applying heated and pressure to the polymer sheets, the polymer will flow into the gaps 634, forming a continuous polymer membrane matrix 640 having exterior and interior surfaces 642 and 644, respectively, as shown in FIG. 31C.

Figure 32:
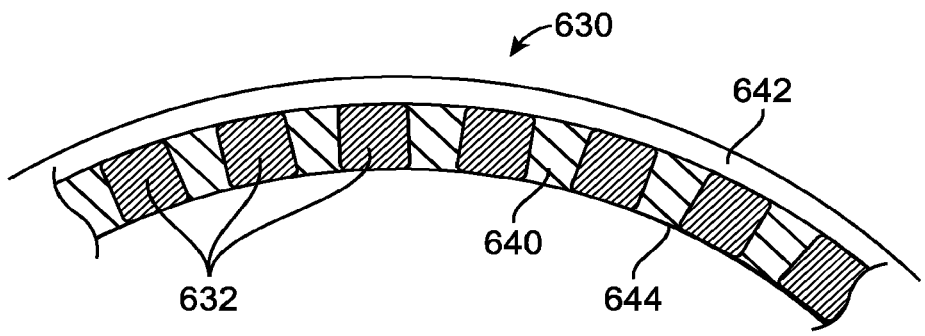
FIG. 32 is a cross-sectional view of a distal tip region fabricated by the method of FIGS. 31A to 31C, shown in a radially expanded configuration.

A distal tip comprising the scaffold 630 and the polymer membrane matrix 640 is shown in its radially expanded configuration in FIG. 32. The polymer matrix 640 is elastic, allowing it to stretch and thin as the distal tip is expanded. While the polymer membrane will usually exert a radially closing force, the expanded supporting scaffold 630 will have sufficient hoop strength (crush resistance) to hold the distal tip open against both the elastic force of the polymer membrane and the vacuum applied during clot aspiration.

Although certain aspects, or examples of the disclosure have been described in detail, variations and modifications and combinations of all or in part of these aspects and examples are within the scope of the present invention and will be apparent to those skilled in the art, including aspects, embodiments or examples that may not provide all the features and benefits described herein. It will be understood by those skilled in the art that the present disclosure extends beyond the specifically disclosed aspects, embodiments, or examples to other alternative or additional examples or embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the aspects, embodiments and/or examples may be made and still fall within the scope of the present disclosure. Accordingly, it should be understood that various features and aspects of the disclosed embodiments can be combined with or substituted for one another in order to form varying modes or examples of the present disclosure. Thus, it is intended that the scope of the present disclosure herein disclosed should not be limited by the disclosed embodiments or examples described above. For all of the embodiments and examples described above, the steps of any methods for example need not be performed sequentially.

What is claimed is:

1. A catheter comprising:
 a tubular catheter body having a proximal end, a distal end, and a lumen extending therebetween; and
 a radially expandable distal tip at the distal end of the tubular catheter body, the radially expandable distal tip having a central passage contiguous with the lumen of the tubular catheter body, wherein the radially expandable distal tip comprises a supporting structure coupled to a membrane, wherein the supporting structure comprises:
 (a) a plurality of radially expandable circumferential rings arranged along a longitudinal axis with circumferential gaps therebetween; and
 (b) a multiplicity of supporting elements, each supporting element having a base end and a free end, wherein the base end is attached to one of the radially expandable circumferential rings and the free end extends axially and/or circumferentially away from the one of the radially expandable circumferential rings;
 wherein at least some of the free ends of the supporting elements are recessed within the radially expandable circumferential rings and do not protrude into the circumferential gaps prior to radial expansion of the radially expandable distal tip; and
 wherein at least some of the free ends of the supporting elements protrude into the circumferential gaps after expansion of the radially expandable distal tip.

2. The catheter of claim 1, wherein the supporting elements are configured to lie within a cylindrical envelope defined by the supporting structure prior to expansion.

3. The catheter of claim 1, wherein at least some of the radially expandable circumferential rings comprise serpentine, zig-zag, square, rectangular, or omega patterned structures including struts joined by crowns, wherein the base ends of the supporting elements are attached to an inner side of the crowns and the free ends are disposed between adjacent struts joined by the crown.

4. The catheter of claim 1, wherein some the free ends of the supporting elements protrude into the circumferential gaps prior to expansion of the radially expandable distal tip.

5. The catheter of claim 1, wherein at least some adjacent rings of the radially expandable circumferential rings are joined by an axial link and/or an attachment point therebetween.

6. The catheter of claim 1, wherein at least some of the plurality of radially expandable circumferential rings comprise helical turns, wherein at least some axially adjacent helical turns are joined continuously end-to-end in a helical pattern.

7. The catheter of claim 6, wherein at least some of the adjacent helical turns are free from axial links or attachment points therebetween.

8. The catheter of claim 7, wherein the supporting elements are configured to lie within the cylindrical envelope defined by the supporting structure prior to expansion.

9. The catheter of claim 1, wherein the radially expandable circumferential rings are arranged cylindrically in a cylindrical envelope prior to expansion.

10. The catheter of claim 1, wherein the radially expandable distal tip has a diameter equal to or smaller than that of the tubular catheter body prior to expansion.

11. The catheter of claim 1, wherein the expandable supporting structure is configured to expand into a cylinder, a cone, or a combination thereof after expansion.

12. The catheter of claim 1, wherein at least a portion of the expandable supporting structure is configured to expand in response to expansion of a balloon catheter within the expandable structure.

13. The catheter of claim 1, wherein at least some of the radially expandable circumferential rings comprise expandable open cells which circumferentially elongate to accommodate radial expansion, wherein the open cells are selected from the group consisting of U-shaped segments, V-shaped segments, O-shaped elements, square, rectangular, or omega patterned.

14. The catheter of claim 1, wherein at least some of the supporting elements on at least some adjacent expandable rings extend in an axial and/or circumferential direction, wherein the at least some of the supporting elements are each contained within one cell space on the radially expandable circumferential rings.

15. The catheter of claim 1, wherein at least some of the supporting elements have a width equal to or larger than a width of an adjacent strut or an adjacent crown on the radially expandable circumferential rings.

16. The catheter of claim 1, wherein at least some of the supporting elements have the same shape, dimensions, and/or configuration as others of the supporting elements.

17. The catheter of claim 1, wherein at least some of the supporting elements comprise linear segments.

18. The catheter of claim 1, wherein at least some of the supporting elements comprise non-linear segments, comprise expanded tips at the free end, and/or branch into two or more segments in a direction toward the free end.

19. The catheter of claim 1, wherein the membrane comprises an elastic membrane.

20. The catheter of claim 19, wherein the elastic membrane comprises one or more materials selected from a group consisting of NeuSoft UR862A, NeuSoft UR852A, NeuSoft UR842A, NeuSoft NEU 455-50A, NeuSoft 596-50A, NeuSoft NEU 455-55A, NeuSoft NEU 455-60A NeuSoft NEU 455-65A, Tecothane AR-62A, Tecoflex EG 80A, Tecoflex EG 85A, Tecoflex EG-93A, Tecoflex TT-1074A, Tecoflex TT-1085A Tecoflex TT-18095A, Elastollan S 50 A 15SPF Elastollan S 60 A 100W Elastollan S 60 A 10WH, Pellethane 2103-70A, Pellethane 70A, Pellethane 2363-80A, Estane 2103-70A, ReZithane Rx50A, Texin RXT 70A, Chronoflex C 80A-Q, Chronoflex AL 75A-Q, Chronoflex C 80A-Q, Polyblend 1100-75A, ResMart Ultra TPU 60A, ResMart Ultra TPU 70A, ResMart Ultra TPU 85A, ResMart Ultra TPU 90A, ResMart Ultra TPU 95A, Ecoflex 00-30, Ecoflex 00-20, Ecoflex SA, Dragon Skin 20, Pebax 2533, Pebax 3033, chronoprene, chronothane, chronosil, combination thereof, or the like.

21. The catheter of claim 1, wherein the membrane comprises an inelastic but stretchable membrane.

22. The catheter of claim 21, wherein the inelastic but stretchable membrane comprises one or more materials selected from the group consisting of one or more polymers such as polyethylene such as LDPE, HDPE, Ultra HMWPE, or the like, Pebax such as Pebax 3533, Pebax 4033, Pebax 4533, Pebax 5533, Pebax 7233 or the like, Nylon such as Nylon 12, Nylon 6/6 or Nylon 6, Polyurethanes such as Pellethane 2363-55D, Pellethane 2363-65D, ResMart Ultra TPU 64D, ResMart Ultra TPU 72D, Fluoropolymers such as PTFE, Poly(vinylidene fluoride-co-hexafluoropropylene), Poly(vinylidene fluoride-co-hexafluoropropylene), Fluorinated ethylene propylene, Polychlorotrifluoroethylene, or the like, or other polymers.

23. The catheter of claim 1, wherein the membrane comprises an elastic material and an inelastic, stretchable material.

24. The catheter of claim 1, wherein the membrane has isotropic properties.

25. The catheter of claim 1, wherein the membrane has anisotropic properties with a higher elasticity in a circumferential or radial direction than in an axial direction.

26. The catheter of claim 1, wherein the membrane covers at least an outer surface and an inner surface of the expandable supporting structure.

27. The catheter of claim 1, wherein the membrane is formed by laminating the expandable scaffold between two layers of the same or different material.

28. The catheter of claim 1, wherein the supporting structure comprises a proximal helical ribbon coupled to a proximal end of helically joined turns, wherein the proximal helical ribbon is configured to resist radial expansion in response to expansion of a balloon catheter within the expandable structure.

29. The catheter of claim 28, wherein the helical ribbon is formed continuously with the helically joined turns.

30. The catheter of claim 29, wherein a distal turn of the helically joined turns is attached to the proximally adjacent helical turn of the helical expandable structure.

31. The catheter of claim 1, wherein outer surface regions of the membrane which are supported by the radially expandable circumferential rings have a radius R measured from a longitudinal axis of the expandable supporting structure;
wherein flat facets in the outer surface of the membrane spanning the circumferential gaps between circumferentially adjacent radially expandable circumferential rings have a radius r measured from a longitudinal axis of the expandable supporting structure; and
wherein the outer surface of the membrane maintains a circularity of at least 97% measured as r/R×100 after the expandable supporting structure is radially expanded by up to 200% from the delivery radius.

32. The catheter of claim 31, wherein the outer surface of the membrane maintains a circularity of at least 97% measured as r/R×100 after the expandable supporting structure is radially expanded by up to 100% from the delivery radius.

33. The catheter of claim 31, wherein the outer surface of the membrane maintains a circularity of at least 97% measured as r/R×100 after the expandable supporting structure is radially expanded by up to 50% from the delivery radius.

34. The catheter of claim 31, wherein the outer surface of the membrane maintains a circularity of at least 98% measured as r/R×100 after the expandable supporting structure is radially expanded from the delivery radius.

35. The catheter of claim 31, wherein the outer surface of the membrane maintains a circularity of at least 98.5% measured as r/R×100 after the expandable supporting structure is radially expanded from the delivery radius.

* * * * *